(12) United States Patent
Ueno et al.

(10) Patent No.: US 9,960,372 B2
(45) Date of Patent: May 1, 2018

(54) MONOAMINE DERIVATIVE AND ORGANIC ELECTROLUMINESCENT DEVICE INCLUDING THE SAME

(71) Applicant: SAMSUNG DISPLAY CO., LTD., Yongin-si, Gyeonggi-do (KR)

(72) Inventors: Masatsugu Ueno, Yokohama (JP); Naoya Sakamoto, Yokohama (JP)

(73) Assignee: Samsung Display Co., Ltd., Yongin-si (KR)

(*) Notice: Subject to any disclaimer, the term of this patent is extended or adjusted under 35 U.S.C. 154(b) by 88 days.

(21) Appl. No.: 14/949,838

(22) Filed: Nov. 23, 2015

(65) Prior Publication Data

US 2016/0155961 A1   Jun. 2, 2016

(30) Foreign Application Priority Data

Nov. 27, 2014 (JP) ................. 2014-239931
Nov. 27, 2014 (JP) ................. 2014-239947

(51) Int. Cl.
*H01L 51/50* (2006.01)
*H01L 51/00* (2006.01)
*C07F 7/08* (2006.01)

(52) U.S. Cl.
CPC ........ *H01L 51/0094* (2013.01); *C07F 7/0816* (2013.01); *H01L 51/006* (2013.01);
(Continued)

(58) Field of Classification Search
None
See application file for complete search history.

(56) References Cited

U.S. PATENT DOCUMENTS

| 8,188,315 B2 | 5/2012 | Hwang et al. |
| 2007/0224448 A1* | 9/2007 | Ikeda ............ C09K 11/06 428/690 |

(Continued)

FOREIGN PATENT DOCUMENTS

| EP | 2 562 229 A1 | 2/2013 | |
| JP | 2011-173973 | * 9/2011 | ............ H01L 51/50 |

(Continued)

OTHER PUBLICATIONS

European Patent Office Abstract Publication No. JP 2007-169187 A, dated Jul. 5, 2007, for JP 4978003 B2, 1 page.

(Continued)

*Primary Examiner* — Gregory D Clark
(74) *Attorney, Agent, or Firm* — Lewis Roca Rothgerber Christie LLP

(57) ABSTRACT

Provided are a monoamine derivative represented by the following Formula 1, and an organic electroluminescent device including the same. When the monoamine derivative represented by Formula 1 is used as a hole transport or hole injection material in the device, the operating voltage may be lowered and the emission efficiency may be improved.

(Continued)

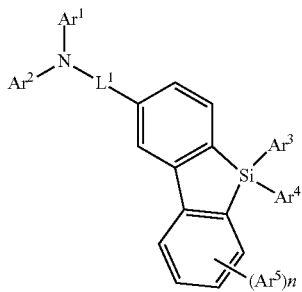

Formula 1

2 Claims, 1 Drawing Sheet

(52) U.S. Cl.
CPC ...... *H01L 51/0061* (2013.01); *H01L 51/5056* (2013.01); *H01L 51/0058* (2013.01); *H01L 51/0071* (2013.01); *H01L 51/0072* (2013.01); *H01L 51/0074* (2013.01); *H01L 51/504* (2013.01); *H01L 51/5004* (2013.01); *H01L 51/5012* (2013.01); *H01L 2251/552* (2013.01)

(56) References Cited

U.S. PATENT DOCUMENTS

2014/0042411 A1 2/2014 Fukuzaki
2014/0138633 A1* 5/2014 Jung ............... H01L 51/0054
    257/40
2016/0248019 A1* 8/2016 Choi ............... H01L 51/0059

FOREIGN PATENT DOCUMENTS

| JP | 4978003 B2 | 7/2012 | | |
|----|---|---|---|---|
| JP | 5261887 B2 | 5/2013 | | |
| JP | 5369020 B2 | 12/2013 | | |
| JP | 5505315 B2 | 3/2014 | | |
| JP | 5691192 B2 | 2/2015 | | |
| KR | 10-2012-0116881 A | 10/2012 | | |
| KR | 10-2013-0093195 A | 8/2013 | | |
| KR | 10-2013-0102669 A | 9/2013 | | |
| KR | 10-2014-0033301 A | 3/2014 | | |
| WO | WO 03/090502 A2 | 10/2003 | | |
| WO | WO 2010/110553 A2 | 9/2010 | | |
| WO | WO 2011/055912 A1 | 5/2011 | | |
| WO | WO 2012/091471 | * | 7/2012 | ............. H01L 51/50 |
| WO | WO 2012/091471 A2 | 7/2012 | | |
| WO | WO 2013/122364 | * | 8/2013 | ............. H01L 51/50 |
| WO | WO 2014/017844 A1 | 1/2014 | | |

OTHER PUBLICATIONS

European Patent Office Abstract Publication No. JP 2011-173937 A, dated Sep. 8, 2011, for JP 5369020 B2, 1 page.
Japanese Patent Abstract for JP 2006-352088 A, which corresponds to JP Publication No. 5261887 B2, published May 10, 2013, 1 page.
Japanese Patent Abstract for JP 2012-142479 A, which corresponds to JP Publication No. 5505315 B2, published Mar. 28, 2014, 1 page.
Japanese Patent Abstract for JP 2011-173973 A, which corresponds to JP Publication No. 5691192 B2, published Feb. 13, 2015, 1 page.

* cited by examiner

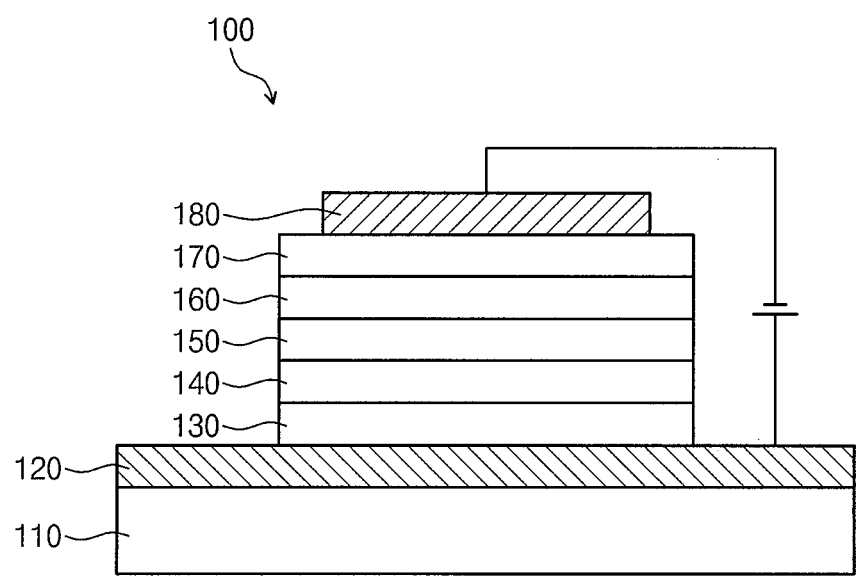

MONOAMINE DERIVATIVE AND ORGANIC ELECTROLUMINESCENT DEVICE INCLUDING THE SAME

CROSS-REFERENCE TO RELATED APPLICATIONS

This patent application claims priority to and the benefit of Japanese Patent Application Nos. 2014-239931, filed on Nov. 27, 2014, and 2014-239947, filed on Nov. 27, 2014, the entire contents of each of which is hereby incorporated by reference.

BACKGROUND

1. Field

One of more aspects of embodiments of the present disclosure relates to a monoamine derivative, and an organic electroluminescent device including the same.

2. Description of the Related Art

Organic electroluminescent (EL) displays are currently being actively developed. In addition, self-emitting organic electroluminescent devices, used in organic electroluminescent displays, are also being actively developed.

In an example structure of an organic electroluminescent device, an anode, a hole injection layer, a hole transport layer, an emission layer, an electron transport layer, an electron injection layer, and a cathode are successively laminated. In such an organic electroluminescent device, holes and electrons are respectively injected from the anode and the cathode and are recombined in the emission layer to generate excitons. Light is emitted when the excitons transition to the ground state.

To improve the emission efficiencies and emission lifetimes of organic electroluminescent devices, various materials are being investigated for use in each layer. For example, aromatic amine derivatives, etc., are being investigated as hole transport materials and/or hole injection materials. In particular, amine derivatives having a carbazolyl group have been investigated as hole transport materials and/or hole injection materials in organic electroluminescent devices.

However, some organic electroluminescent devices that use amine derivatives have high operating voltages and low emission efficiencies. Therefore, there is a demand for materials that can lower the operating voltage and improve the emission efficiency of an organic electroluminescent device when incorporated in the organic layers.

SUMMARY

One or more aspects of embodiments of the present disclosure provide a novel monoamine derivative which may lower the operating voltage and improve the emission efficiency of an organic electroluminescent device, and an organic electroluminescent device that includes the monoamine derivative.

One or more embodiments of the present disclosure provide a monoamine derivative represented by Formula 1:

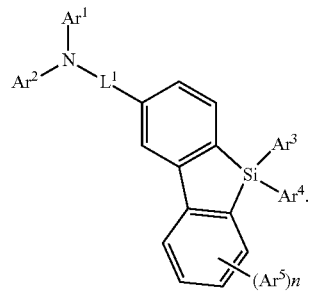

Formula 1

In Formula 1, $Ar^1$ and $Ar^2$ may each independently be selected from a substituted or unsubstituted aryl group having 6 to 50 carbon atoms for forming a ring, and a substituted or unsubstituted heteroaryl group having 5 to 50 carbon atoms for forming a ring; $Ar^3$ to $Ar^5$ may each independently be selected from hydrogen, deuterium, a halogen atom, a substituted or unsubstituted alkyl group having 1 to 20 carbon atoms, a substituted or unsubstituted aryl group having 6 to 50 carbon atoms for forming a ring, a substituted or unsubstituted heteroaryl group having 5 to 50 carbon atoms for forming a ring, and an aryl or heteroaryl group obtained through ring condensation with any adjacent substituent; n may be an integer from 0 to 4; and $L^1$ may be selected from a single bond, a substituted or unsubstituted arylene group having 6 to 18 carbon atoms for forming a ring, and a substituted or unsubstituted heteroarylene group having 5 to 15 carbon atoms for forming a ring.

The operating voltage may be lowered and the emission efficiency may be improved when such a first monoamine derivative is included in an organic electroluminescent device.

In one or more embodiments, $Ar^1$ and $Ar^2$ may each independently be selected from a substituted or unsubstituted aryl group having 6 to 18 carbon atoms for forming a ring, and a substituted or unsubstituted heteroaryl group having 5 to 12 carbon atoms for forming a ring.

The operating voltage may be further lowered and the emission efficiency may be further improved when such a first monoamine derivative is included in an organic electroluminescent device.

In one or more embodiments, $Ar^1$ and $Ar^2$ may each independently be selected from a biphenyl group and a terphenyl group.

Accordingly, the operating voltage may be further lowered and the emission efficiency may be further improved when such a first monoamine derivative is included in an organic electroluminescent device.

In one or more embodiments, $Ar^3$ to $Ar^5$ may each independently be selected from a halogen atom, a substituted or unsubstituted alkyl group having 1 to 5 carbon atoms, and a substituted or unsubstituted aryl group having 6 to 12 carbon atoms for forming a ring.

Accordingly, the operating voltage may be further lowered and the emission efficiency may be further improved when such a monoamine derivative is included in an organic electroluminescent device, according to the embodiment represented by Formula 1.

In one or more embodiments, $Ar^3$ and $Ar^4$ may each independently be selected from a methyl group and a phenyl group.

Accordingly, the operating voltage may be further lowered and the emission efficiency may be further improved when such a monoamine derivative is included in an organic electroluminescent device, according to one or more embodiments.

In one or more embodiments, $L^1$ may be selected from a single bond, a phenylene group, and a biphenylene group.

The monoamine derivative represented by the above Formula 1 may be selected from the group of compounds represented by Formula 2:

Formula 2

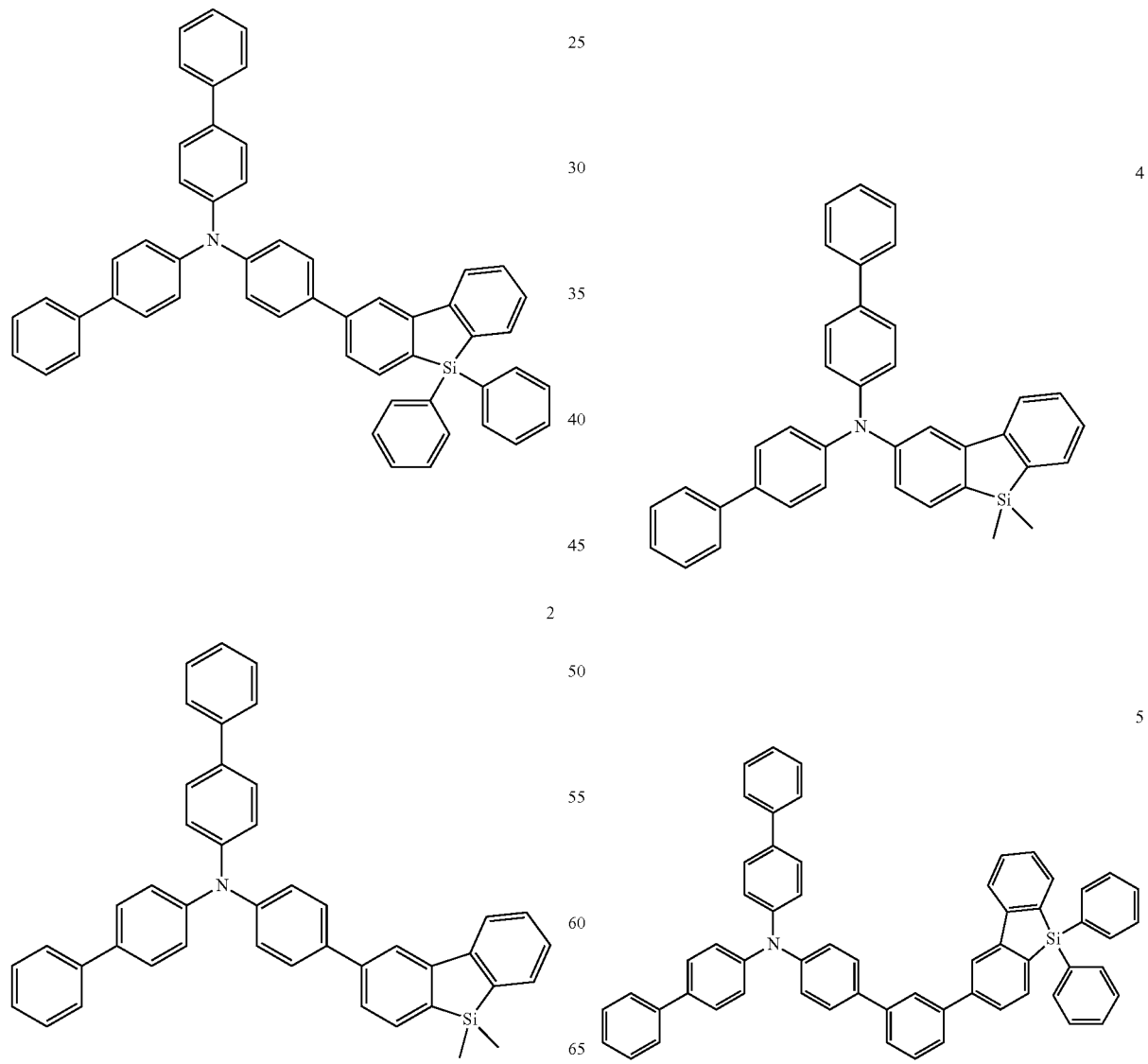

6
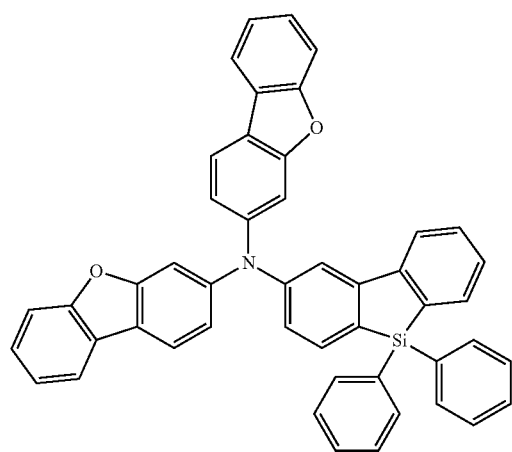
7
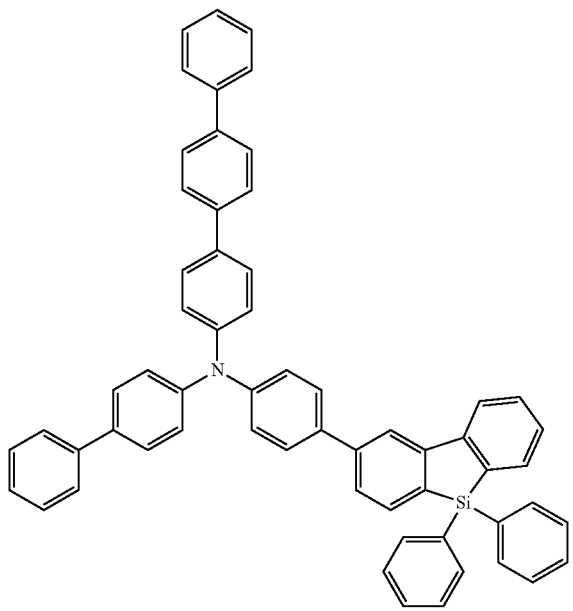
8
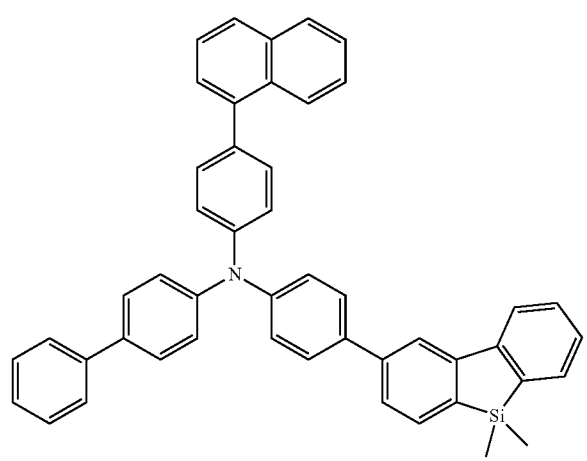
9
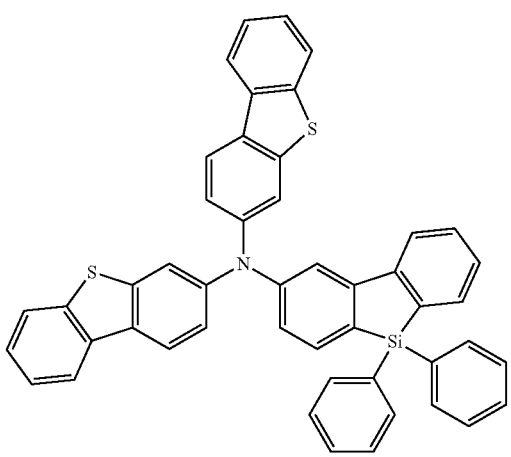
10
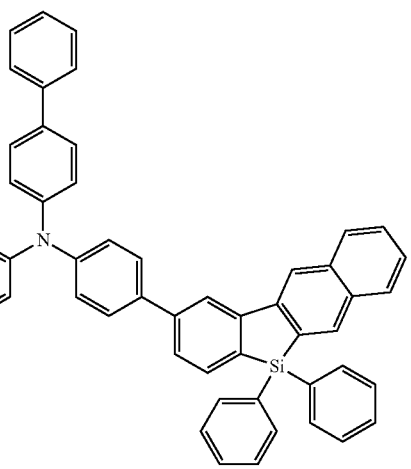
11

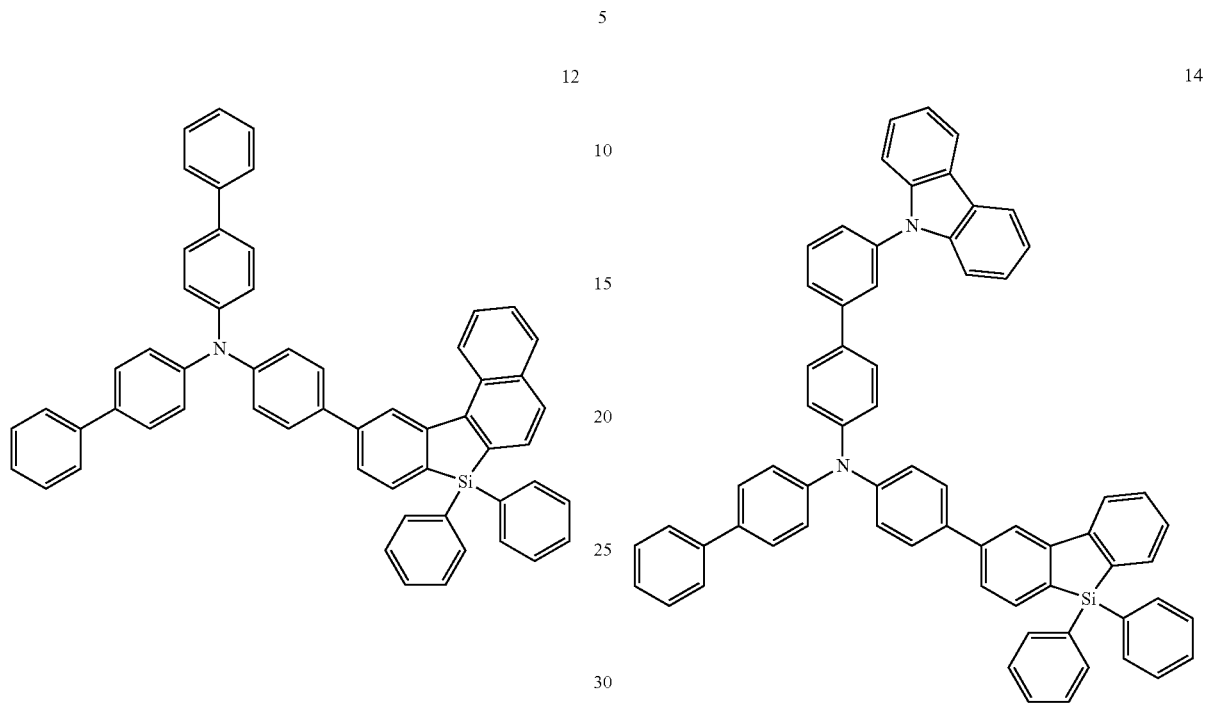
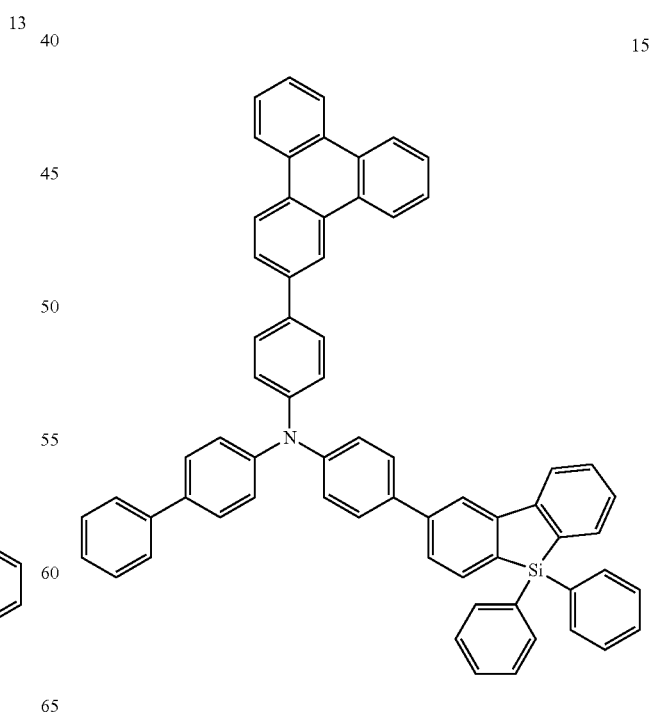

16

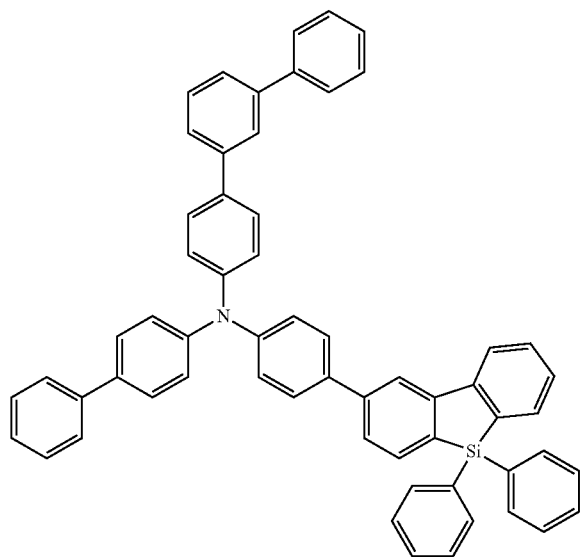

17

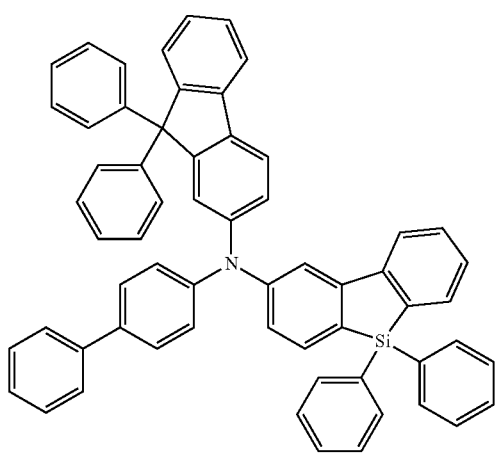

18

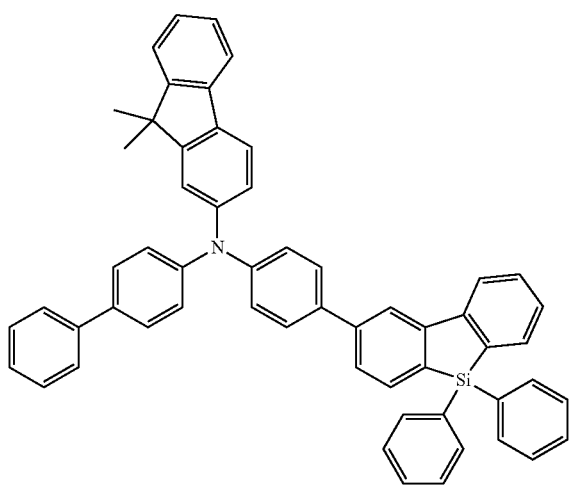

19

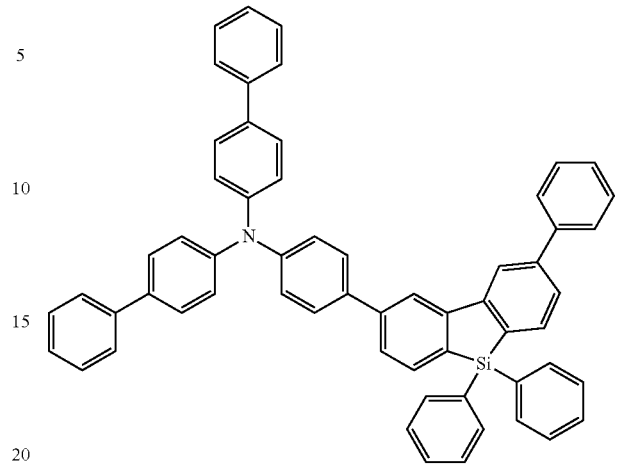

20

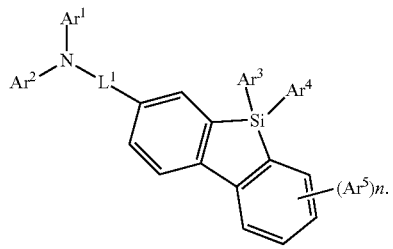

Accordingly, the operating voltage may be further lowered and the emission efficiency may be further improved when such a monoamine derivative is included in an organic electroluminescent device, according to one or more embodiments.

One or more embodiments of the present disclosure provide a second monoamine derivative represented by the following Formula 3:

Formula 3

In Formula 3, $Ar^1$ and $Ar^2$ may each independently be selected from a substituted or unsubstituted aryl group having 6 to 50 carbon atoms for forming a ring, and a substituted or unsubstituted heteroaryl group having 5 to 50 carbon atoms for forming a ring; $Ar^3$ to $Ar^5$ may each independently be selected from hydrogen, deuterium, a halogen atom, a substituted or unsubstituted alkyl group having 1 to 20 carbon atoms, a substituted or unsubstituted aryl group having 6 to 50 carbon atoms for forming a ring, a substituted or unsubstituted heteroaryl group having 5 to 50 carbon atoms for forming a ring, and an aryl or heteroaryl group obtained through ring condensation with any adjacent substituent; n may be an integer from 0 to 4; and $L^1$ may be selected from a single bond, a substituted or unsubstituted arylene group having 6 to 18 carbon atoms for forming a ring, and a substituted or unsubstituted heteroarylene group having 5 to 15 carbon atoms for forming a ring.

In one or more embodiments, $Ar^1$ and $Ar^2$ may each independently be selected from a substituted or unsubstituted aryl group having 6 to 18 carbon atoms for forming a ring, and a substituted or unsubstituted heteroaryl group having 5 to 12 carbon atoms for forming a ring.

In one or more embodiments, $Ar^1$ and $Ar^2$ may each independently be selected from a biphenyl group and a terphenyl group.

In one or more embodiments, $Ar^3$ to $Ar^5$ may each independently be selected from a halogen atom, a substituted or unsubstituted alkyl group having 1 to 5 carbon atoms, and a substituted or unsubstituted aryl group having 6 to 12 carbon atoms for forming a ring.

In one or more embodiments, $Ar^3$ and $Ar^4$ may each independently be selected from a methyl group and a phenyl group.

In one or more embodiments, $L^1$ may be selected from a single bond, a phenylene group, and a biphenylene group.

The monoamine derivative represented by the above Formula 3 may be selected from the group of compounds represented by Formula 4:

Formula 4

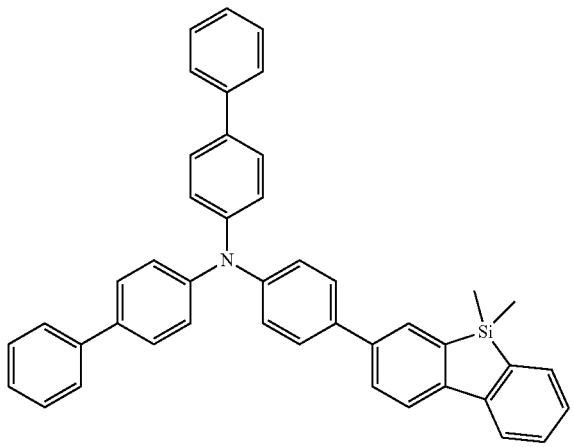

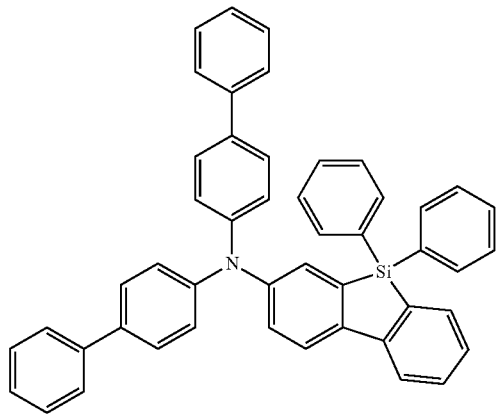

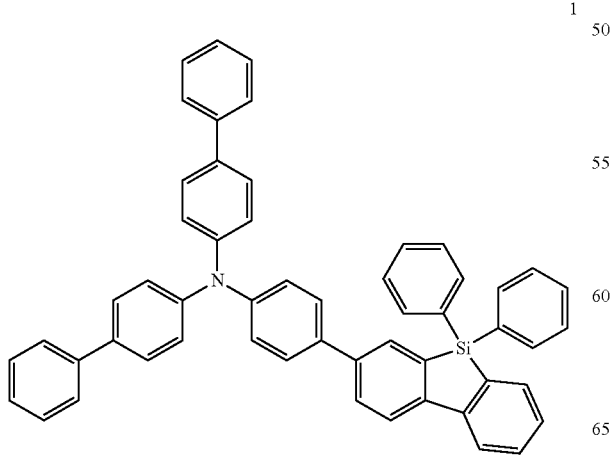

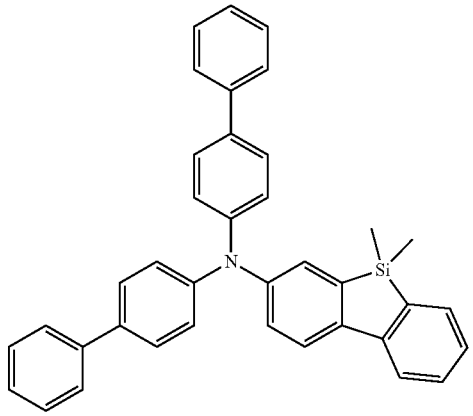

5
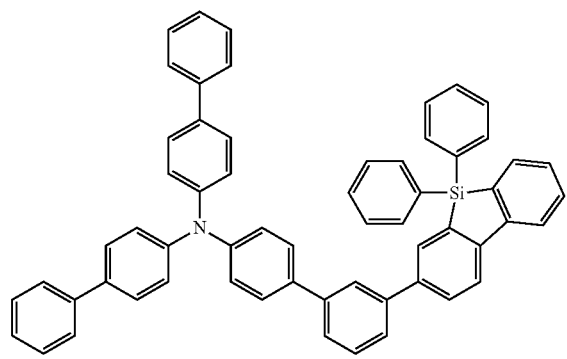
6
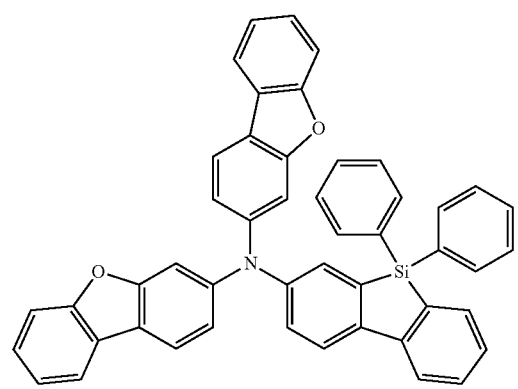
7
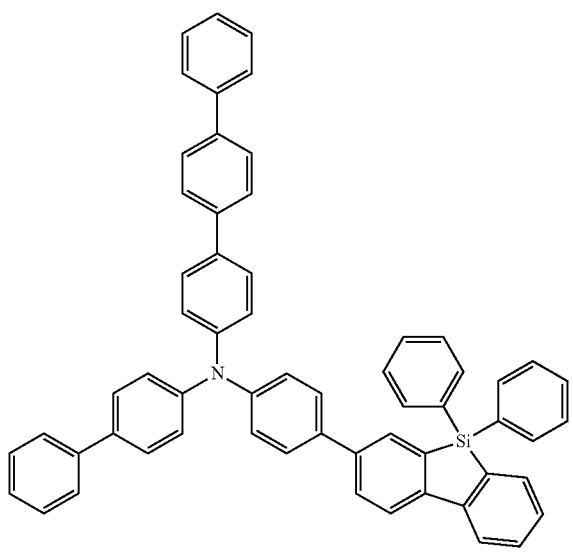
8
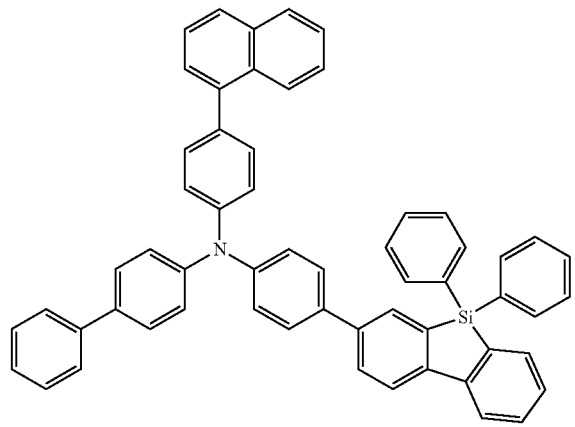
9
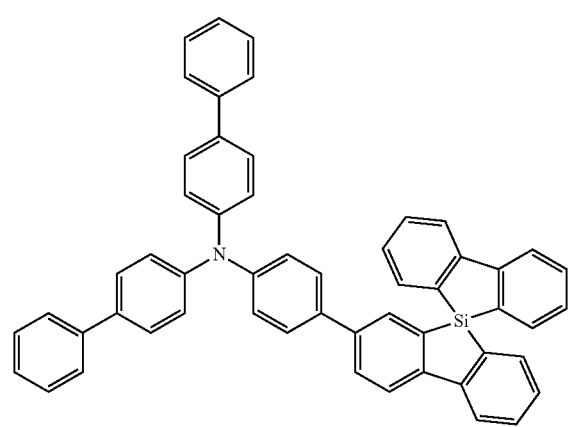
10

11
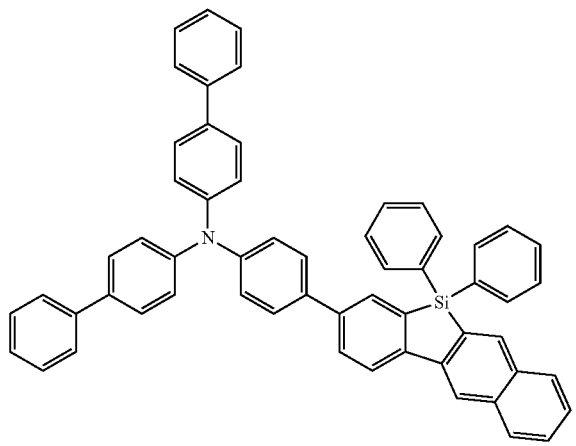
12
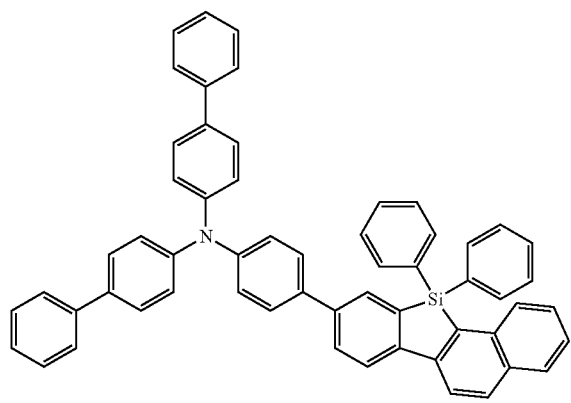
13
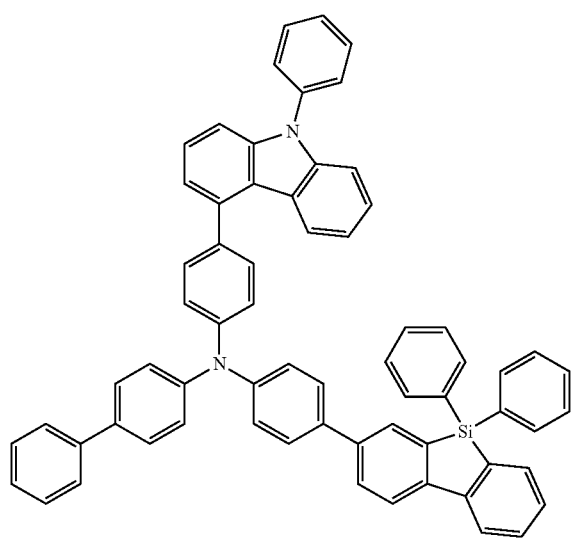
14
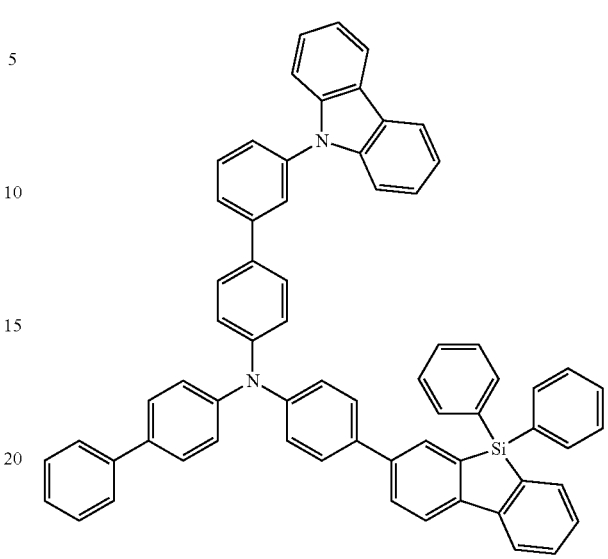
15
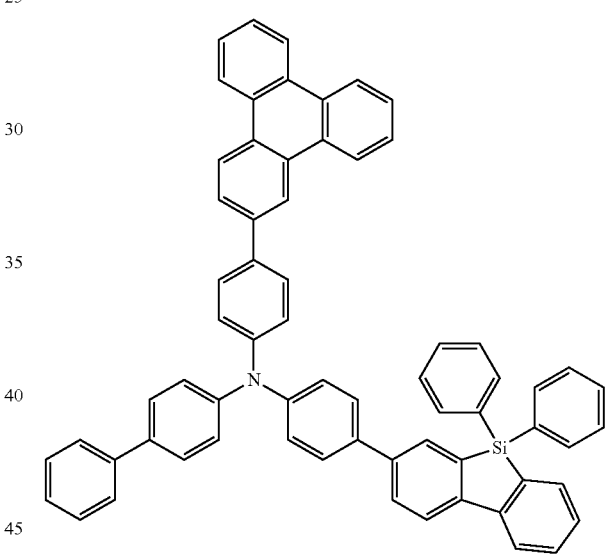
16
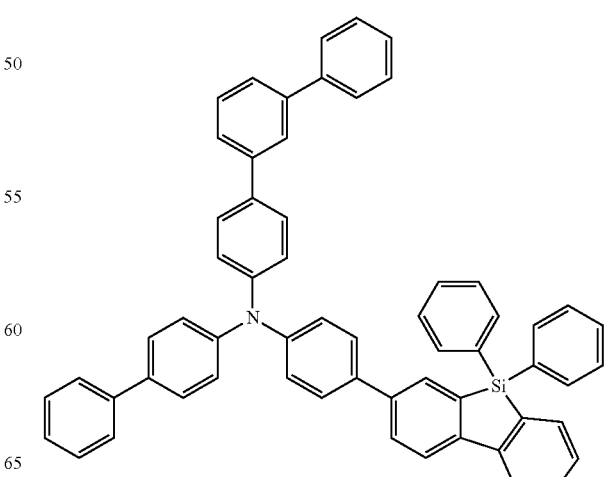

17
-continued

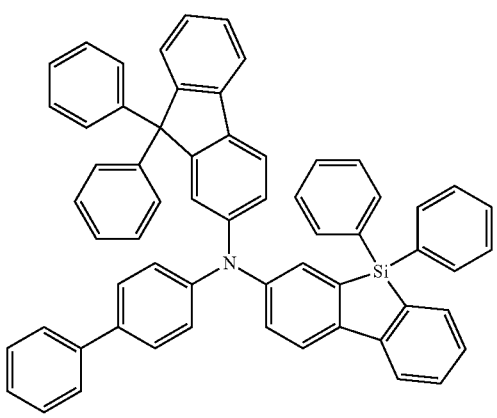

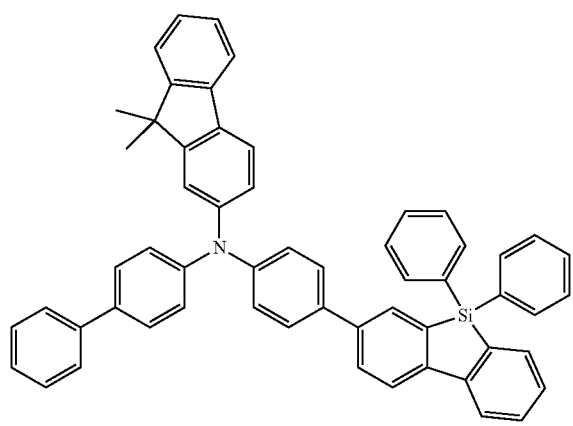

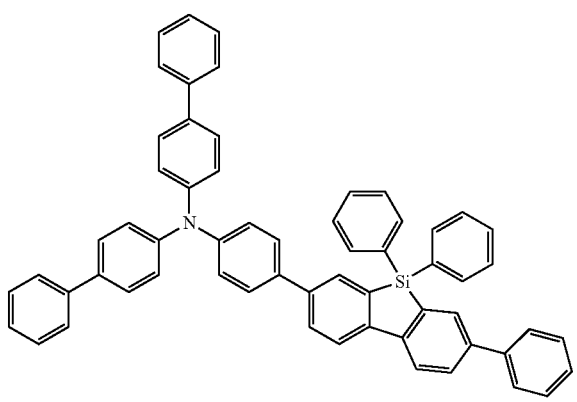

18
-continued

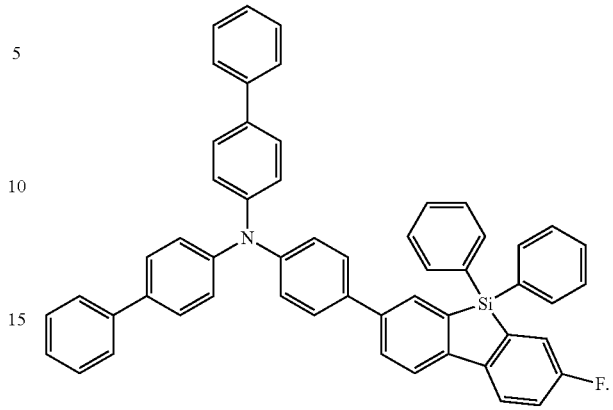

Accordingly, the operating voltage may be further lowered and the emission efficiency may be further improved when such a monoamine derivative is included in an organic electroluminescent device, according to one or more embodiments.

One or more embodiments of the present disclosure provide an organic electroluminescent device, including an anode; a hole injection layer on the anode; a hole transport layer on the hole injection layer; and an emission layer on the hole transport layer; wherein at least one layer selected from the hole injection layer, the hole transport layer, and the emission layer may include the monoamine derivative according to an embodiment described above.

Accordingly, an organic electroluminescent device having a lowered operating voltage and improved emission efficiency is provided.

BRIEF DESCRIPTION OF THE DRAWING

The accompanying drawing is included to enable further understanding of the present disclosure, and is incorporated in and constitutes a part of this specification. The drawing illustrates example embodiments of the present disclosure and, together with the description, serves to explain principles of the present disclosure.

The drawing is a schematic diagram illustrating one example of an organic electroluminescent device according to an embodiment of the present disclosure.

DETAILED DESCRIPTION

Hereinafter, example embodiments of the present disclosure will be described with reference to the accompanying drawing. As those skilled in the art would realize, the described embodiments may be modified in various different ways, all without departing from the spirit or scope of the present disclosure.

In the description and drawing, like reference numerals refer to like elements or elements having like functions throughout, and repeated explanation thereof will not be provided. The thickness of layers, films, panels, regions, etc., may be exaggerated in the drawings for clarity. It will be understood that when an element such as a layer, film, region, or substrate is referred to as being "on" another element, it can be directly on the other element or intervening elements may also be present. In contrast, when an

1-1. Monoamine Derivative Represented by Formula 1

Hereinafter, the monoamine derivative represented by Formula 1 may be described as the first monoamine derivative.

First, a description will be given of the first monoamine derivative according to an embodiment of the present disclosure. In this embodiment, the first monoamine derivative is a compound that may be used as a hole transport and/or hole injection material in an organic electroluminescent device, and is represented by the following Formula 1:

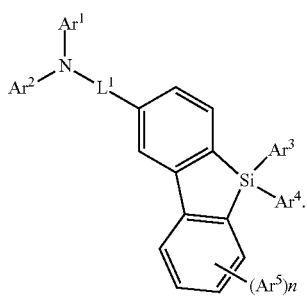

Formula 1

In Formula 1, $Ar^1$ and $Ar^2$ may each independently be selected from a substituted or unsubstituted aryl group having 6 to 50 carbon atoms for forming a ring, and a substituted or unsubstituted heteroaryl group having 5 to 50 carbon atoms for forming a ring; $Ar^3$ to $Ar^5$ may each independently be selected from hydrogen, deuterium, a halogen atom, a substituted or unsubstituted alkyl group having 1 to 20 carbon atoms, a substituted or unsubstituted aryl group having 6 to 50 carbon atoms for forming a ring, a substituted or unsubstituted heteroaryl group having 5 to 50 carbon atoms for forming a ring, and an aryl or heteroaryl group obtained through ring condensation with any adjacent substituent; n may be an integer from 0 to 4; and $L^1$ may be selected from a single bond, a substituted or unsubstituted arylene group having 6 to 18 carbon atoms for forming a ring, and a substituted or unsubstituted heteroarylene group having 5 to 15 carbon atoms for forming a ring.

Moreover, in Formula 1, amino groups are excluded from the scope of substituents which may be included in $Ar^1$ to $Ar^5$. Thus, the compound represented by Formula 1 is a monoamine derivative having only one amino group in the overall structural formula.

Generally, the first monoamine derivative represented by Formula 1 may contain a dibenzosilolyl moiety, and may thus have a deeper highest occupied molecular orbital (HOMO) level (e.g., the absolute value of the energy of the HOMO level becomes larger) than an analogous diamine derivative having arylamino groups connected to both sides.

When compounds having a shallow HOMO level (e.g., having a small absolute value of the energy of the HOMO level) are used in the hole transport layer, as may be the case when a diamine derivative, etc. is used, the energy barrier against transfer of holes to the light-emitting material in the emission layer is often large, the density of holes being transported to the emission layer may be reduced, and the emission efficiency of the organic electroluminescent device may be decreased. In particular, most blue light-emitting materials have a deep HOMO level. Therefore, when a blue light-emitting material is used in the emission layer and a compound having a shallow HOMO level is used in the hole transport layer, the gap between the HOMO levels of the light-emitting material and the compound may be large, and thus the emission efficiency is often decreased.

In one or more embodiments, the first monoamine derivative represented by Formula 1 has a deeper HOMO level than the analogous diamine derivative. In this case, the energy barrier between the first monoamine derivative and the light-emitting material in the emission layer may be small. Thus, using the first monoamine derivative represented by Formula 1 may lower the operating voltage and improve the emission efficiency of the organic electroluminescent device.

When the emission layer includes a blue light-emitting material and/or a green light-emitting material, the first monoamine derivative represented by Formula 1 may suitably reduce the operating voltage and improve the emission efficiency of the organic electroluminescent device.

The first monoamine derivative may be included in at least one of the layers between the emission layer and the anode. Specifically, the monoamine derivative represented by Formula 1 may be included in the hole transport layer and/or the hole injection layer.

However, in the organic electroluminescent device, the layers that may include the first monoamine derivative represented by Formula 1 are not limited to those in the examples given above. For example, the first monoamine derivative represented by Formula 1 may be included in any of the organic layers between the anode and the cathode of an organic electroluminescent device, and in particular, may be included in the emission layer.

In the above Formula 1, $Ar^1$ and $Ar^2$ may each independently be selected from a substituted or unsubstituted aryl group having 6 to 18 carbon atoms for forming a ring, and a substituted or unsubstituted heteroaryl group having 5 to 12 carbon atoms for forming a ring. Moreover, $Ar^1$ and $Ar^2$ may each independently be selected from a biphenyl group and a terphenyl group.

When $Ar^1$ and $Ar^2$ are such substituents as described above, the first monoamine derivative represented by Formula 1 may reduce the operating voltage and improve the emission efficiency of an organic electroluminescent device, as will be described in examples below.

In the above Formula 1, $Ar^3$ to $Ar^5$ may each independently be selected from a halogen atom, a substituted or unsubstituted alkyl group having 1 to 5 carbon atoms, and a substituted or unsubstituted aryl group having 6 to 12 carbon atoms for forming a ring. Moreover, $Ar^3$ and $Ar^4$ may each independently be selected from a methyl group and a phenyl group.

When $Ar^3$ to $Ar^5$ are such substituents as described above, the first monoamine derivative represented by Formula 1 may reduce the operating voltage and improve the emission efficiency of an organic electroluminescent device, as will be described in examples below.

In the above Formula 1, $L^1$ may be selected from a single bond, a phenylene group, and a biphenylene group.

When $L^1$ is such a substituent as described above, the first monoamine derivative represented by Formula 1 may reduce the operating voltage and improve the emission efficiency of an organic electroluminescent device, as will be described in examples below.

In the above Formula 1, non-limiting examples of an aryl group or a heteroaryl group may include a phenyl group, a biphenyl group, a terphenyl group, a naphthyl group, an anthryl group, a phenanthrenyl group, a fluorenyl group, an indenyl group, a pyrenyl group, a fluoranthenyl group, a triphenylenyl group, a pyrazinyl group, a pyrrolyl group, a pyridyl group, a pyrimidyl group, a pyridazyl group, a pyrazinyl group, a furanyl group, a pyranyl group, a thienyl group, a quinolyl group, an isoquinolyl group, a benzofuranyl group, a benzothienyl group, an indolyl group, a benzoxazolyl group, a benzothiazolyl group, a quinoxalyl group, a benzoimidazolyl group, a pyrazolyl group, a tetrazolyl group, an imidazolyl group, an oxazolyl group, an isoxazolyl group, a thiazolyl group, an isothiazolyl group, a carbazolyl group, a dibenzofuranyl group, a dibenzothienyl group, etc.

In the above Formula 1, non-limiting examples of an alkyl group may include a straight-chain alkyl group (such as a methyl group, an ethyl group, a propyl group, a butyl group, an octyl group, a decyl group, a pentadecyl group, etc.), and a branched chain alkyl group (such as a t-butyl group, etc.).

In the above Formula 1, a halogen atom may include a fluorine atom, a chlorine atom, a bromine atom, an iodine atom, etc.

In the above Formula 1, non-limiting examples of an arylene group and a heteroarylene group may include divalent groups in which one additional hydrogen is substituted from the aryl and heteroaryl groups which are described above.

Specific examples of the above-described first monoamine derivative represented by Formula 1 may include Compounds 1 to 20, which are represented in Formula 2, below. However, examples of the first monoamine derivative according to the present embodiment are not limited to the following compounds:

Formula 2

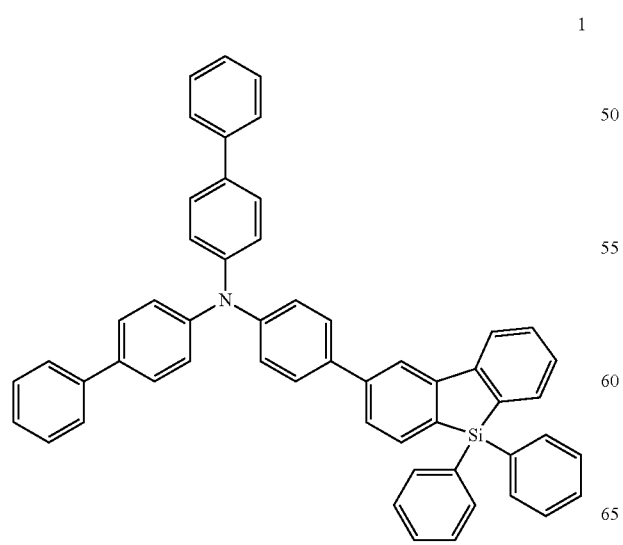

1

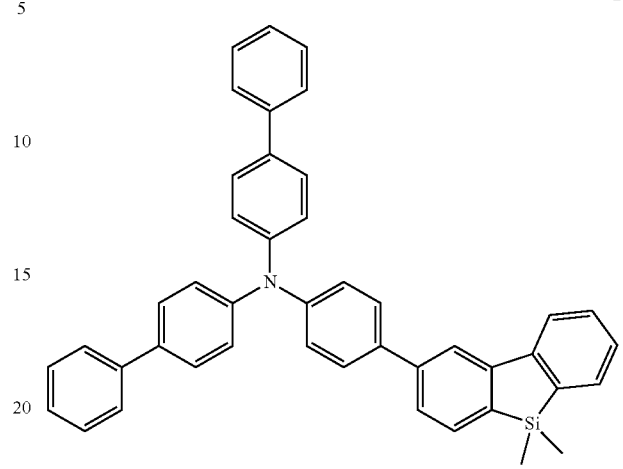

2

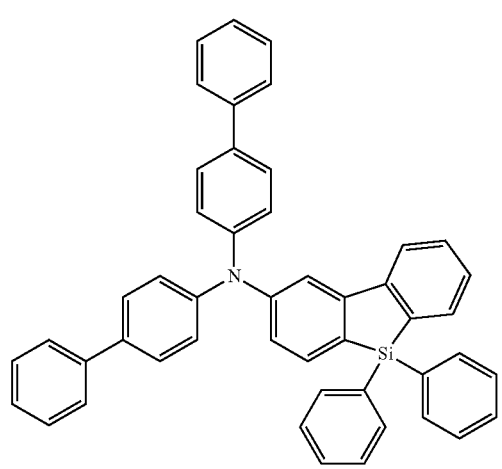

3

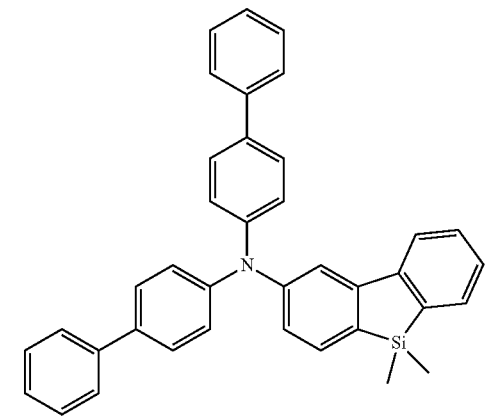

4

5
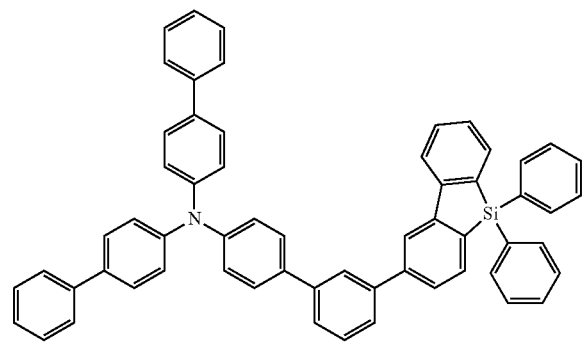
6
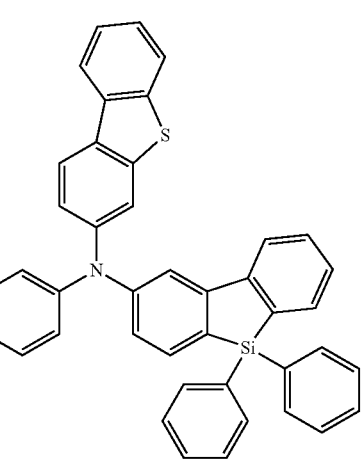
7
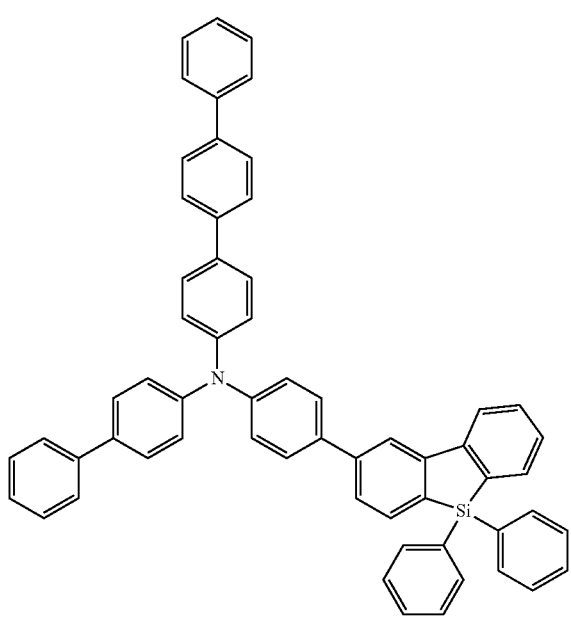
8
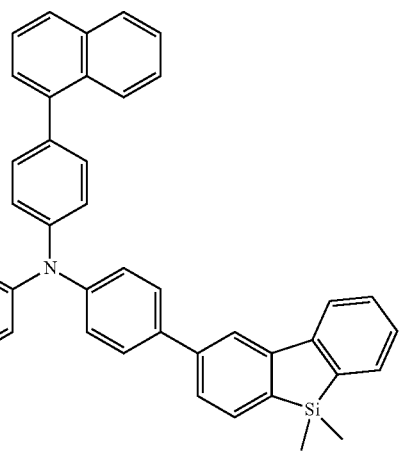
9
10

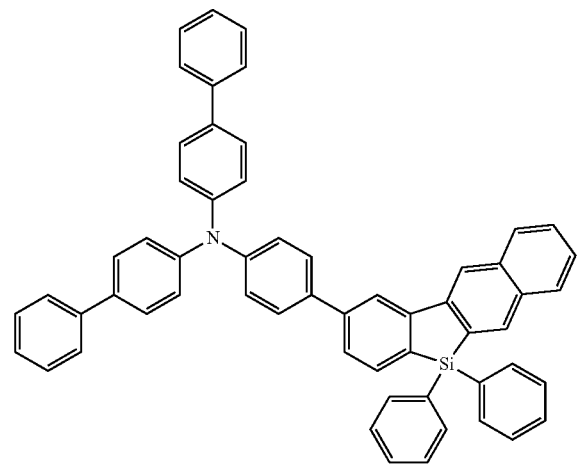
11
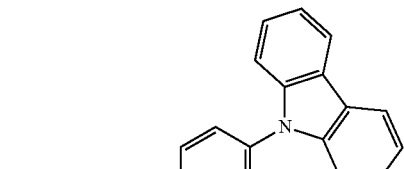
5
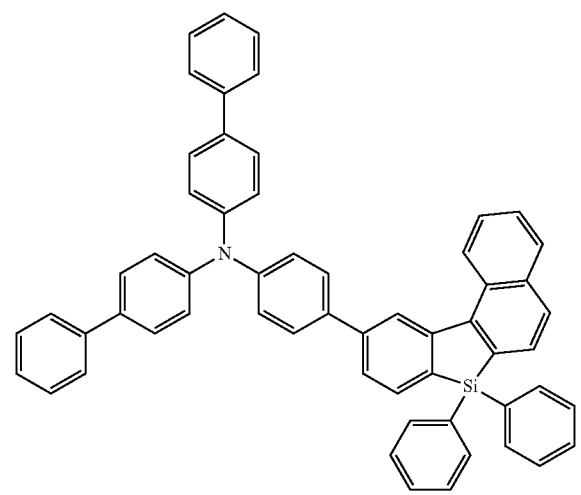
12
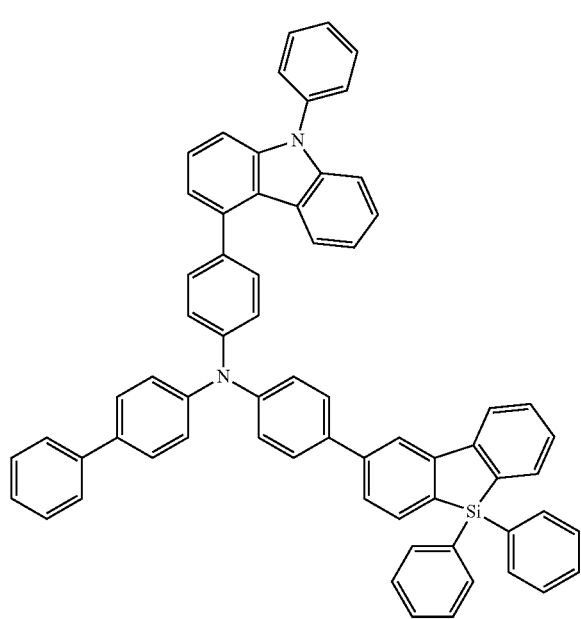
13
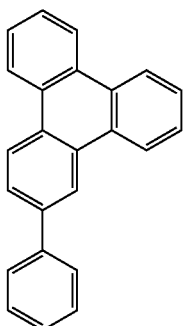
14
15

16

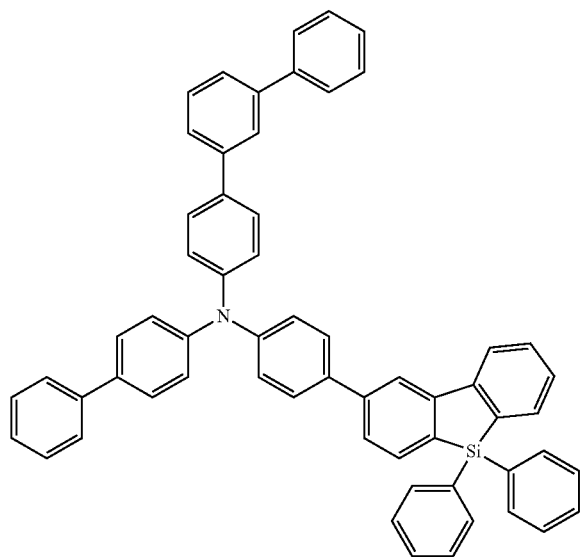

17

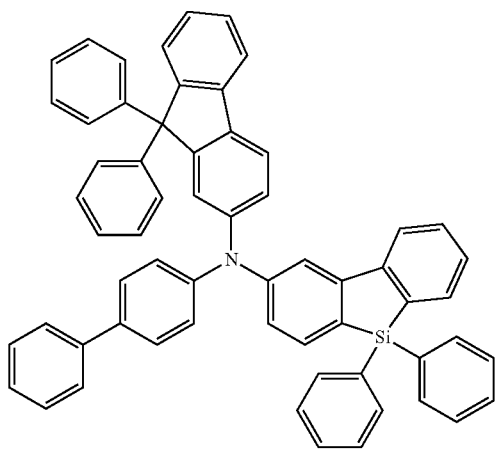

18

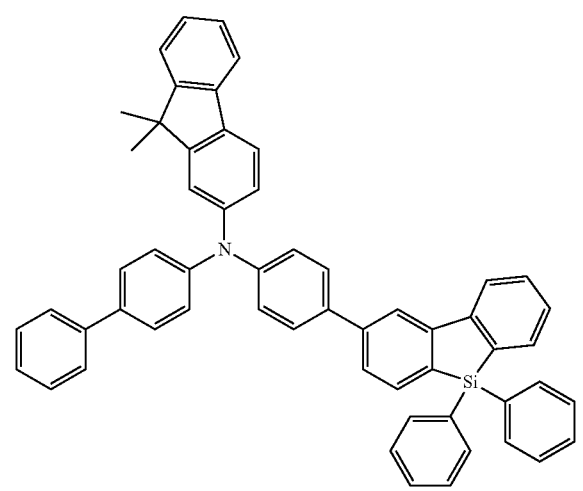

19

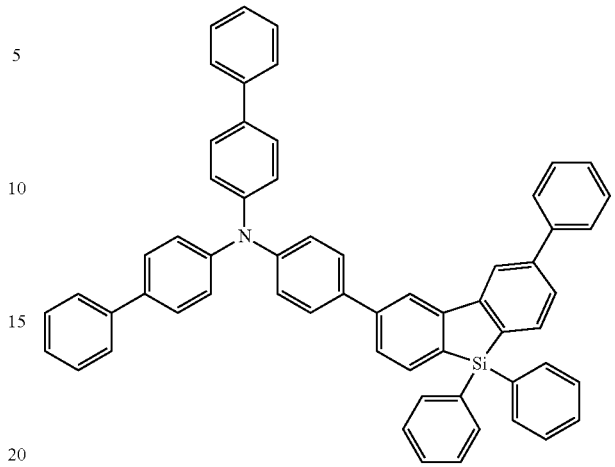

20

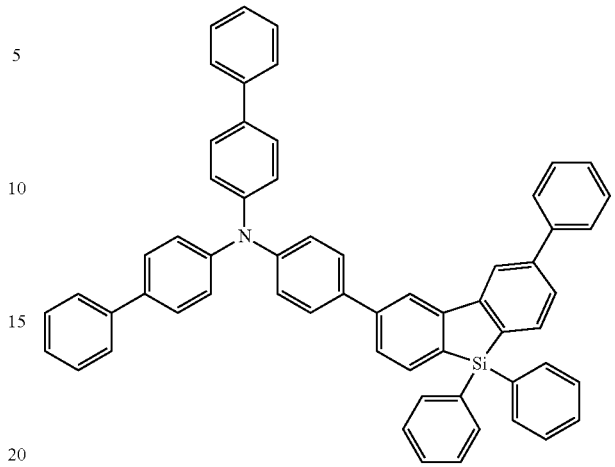

As described above, the first monoamine derivative may be used as a hole transport material and/or a hole injection material in one or more embodiments. In addition, since the first monoamine derivative may cause the HOMO level to be deeper and the energy barrier against hole transfer to the light-emitting material in the emission layer to be smaller, the operating voltage may be lowered and the emission efficiency may be improved in the organic electroluminescent device.

As above, an embodiment of the first monoamine derivative will now be described in more detail.

1-2. An Organic Electroluminescent Device of an Embodiment which Includes the Monoamine Derivative Represented by Formula 1

Hereinafter, the monoamine derivative represented by Formula 1 may be described as the first monoamine derivative.

Referring to the drawing, a detailed description will be given of one or more embodiments of an organic electroluminescent device that includes the first monoamine derivative. The drawing is a schematic diagram illustrating an example embodiment of the organic electroluminescent device.

As illustrated in the drawing, an organic electroluminescent device 100 according to the present embodiment includes a substrate 110, a first electrode 120 on the substrate 110, a hole injection layer 130 on the first electrode 120, a hole transport layer 140 on the hole injection layer 130, an emission layer 150 on the hole transport layer 140, an electron transport layer 160 on the emission layer 150, an electron injection layer 170 on the electron transport layer 160, and a second electrode 180 on the electron injection layer 170.

For example, the first monoamine derivative represented by Formula 1 may be included in at least one of the hole injection layer 130 and/or the hole transport layer 140, which are positioned between the first electrode 120 and the emission layer 150. The first monoamine derivative may also be included in the emission layer 150.

Any substrate suitable for use in an organic electroluminescent device may be used as the substrate 110. For example, the substrate 110 may be a glass substrate, a semiconductor substrate, a transparent plastic substrate, etc.

The first electrode 120 is positioned on the substrate 110. For example, the first electrode 120 may be an anode, and may be formed as a transmissive electrode using a metal, an alloy, and/or a conductive compound which has a large work function. For example, the first electrode 120 may be formed of indium tin oxide ($In_2O_3$—$SnO_2$, ITO), indium zinc oxide ($In_2O_3$—ZnO, IZO), tin oxide ($SnO_2$), zinc oxide (ZnO), etc., which exhibit good transparency and conductivity. Moreover, the first electrode 120 may also be formed as a reflective electrode in which the transparent conducting layer and layers of magnesium (Mg), aluminum (Al), etc. are laminated.

The hole injection layer 130 is positioned on the first electrode 120. The hole injection layer 130 has the function of allowing holes to be easily injected from the first electrode 120, and may have a thickness of, for example, about 10 nm to about 150 nm.

The hole injection layer 130 may include the first monoamine derivative, and may also be formed of any suitable hole injection material. The hole injection material used to form the hole injection layer 130 may include, for example, triphenylamine-containing poly ether ketone (TPAPEK), 4-isopropyl-4'-methyldiphenyliodoniumtetrakis(pentafluorophenyl)borate (PPBI), N,N'-diphenyl-N,N'-bis-[4-(phenyl-m-tolyl-amino)-phenyl]-biphenyl-4,4'-diamine (DNTPD), a phthalocyanine compound such as copper phthalocyanine, 4,4',4"-tris(3-methylphenylphenylamino)triphenylamine (m-MTDATA), N,N'-di(1-naphthyl)-N,N'-diphenylbenzidine (NPB), 4,4',4"-tris{N,N-diphenylamino}triphenylamine (TDATA), 4,4',4"-tris(N,N-2-naphthylphenylamino)triphenylamine (2-TNATA), polyaniline/dodecylbenzenesulfonic acid (PANI/DBSA), poly(3,4-ethylenedioxythiophene)/poly(4-styrenesulfonate (PEDOT/PSS), polyaniline/camphorsulfonic acid (PANI/CSA), polyaniline/poly(4-styrenesulfonate (PANI/PSS), etc.

The hole transport layer 140 is positioned on the hole injection layer 130. The hole transport layer 140 has the function of transporting holes and may have a thickness of, for example, about 10 nm to about 150 nm. The hole transport layer 140 may have a multilayered structure.

In one or more embodiments, the hole transport layer 140 may be formed of the first monoamine derivative. However, when the first monoamine derivative is included in another layer (for example, the hole injection layer 130, or the emission layer 150), the hole transport layer 140 may be formed of any suitable hole transport material. The suitable hole transport material may include, for example, 1,1-bis [(di-4-tolylamino)phenyl]cyclohexane (TAPC); a carbazole derivative such as N-phenyl carbazole or polyvinyl carbazole; N,N'-bis(3-methylphenyl)-N,N'-diphenyl-[1,1-biphenyl]-4,4'-diamine (TPD); 4,4', 4"-tris(N-carbazolyl)triphenylamine (TCTA); N,N'-di(1-naphthyl)-N,N'-diphenylbenzidine (NPB), etc.

The emission layer 150 is positioned on the hole transport layer 140. The emission layer 150 may emit light through fluorescence, phosphorescence, etc., and may have a thickness of, for example, about 10 nm to about 60 nm. Any suitable light-emitting material may be used in the emission layer 150. Non-limiting examples of the suitable light-emitting material may include a fluoranthene derivative, a styryl derivative, a pyrene derivative, an arylacetylene derivative, a fluorene derivative, a perylene derivative, a chrysene derivative, etc. Moreover, a styryl derivative, a pyrene derivative, a perylene derivative, or an anthracene derivative may be used. For example, an anthracene derivative represented by Formula 5 may be used in the emission layer 150:

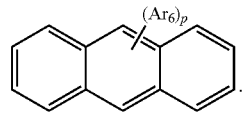

Formula 5

In Formula 5, each $Ar_6$ may independently be selected from hydrogen, deuterium, a substituted or unsubstituted alkyl group having 1 to 50 carbon atoms, a substituted or unsubstituted cycloalkyl group having 3 to 50 carbon atoms for forming a ring, a substituted or unsubstituted alkoxy group having 1 to 50 carbon atoms, a substituted or unsubstituted aralkyl group having 7 to 50 carbon atoms, a substituted or unsubstituted aryloxy group having 6 to 50 carbon atoms for forming a ring, a substituted or unsubstituted arylthio group having 6 to 50 carbon atoms for forming a ring, a substituted or unsubstituted alkoxycarbonyl group having 2 to 50 carbon atoms, a substituted or unsubstituted aryl group having 6 to 50 carbon atoms for forming a ring, a substituted or unsubstituted heteroaryl group having 5 to 50 atoms for forming a ring, a substituted or unsubstituted silyl group, a carboxyl group, a halogen atom, a cyano group, a nitro group, and a hydroxyl group; and p may be an integer from 1 to 10.

Specifically, each $Ar_6$ may independently be selected from a phenyl group, a biphenyl group, a terphenyl group, a naphthyl group, a phenylnaphthyl group, a naphthylphenyl group, an anthryl group, a phenanthryl group, a fluorenyl group, an indenyl group, a pyrenyl group, an acetonaphthenyl group, a fluoranthenyl group, a triphenylenyl group, a pyridyl group, a furanyl group, a pyranyl group, a thienyl group, a quinolyl group, an isoquinolyl group, a benzofuranyl group, a benzothienyl group, an indolyl group, a carbazolyl group, a benzoxazolyl group, a benzothiazolyl group, a quinoxalyl group, a pyrazolyl group, a dibenzofuranyl group, a dibenzothienyl group, etc. In addition, each $Ar_6$ may be a phenyl group, a biphenyl group, a terphenyl group, a fluorenyl group, a carbazolyl group, a dibenzofuranyl group, etc.

The compounds represented by the above Formula 5 may include, for example, Compounds a-1 to a-12, below. However, the compounds represented by Formula 5 are not limited to Compounds a-1 to a-12:

a-1
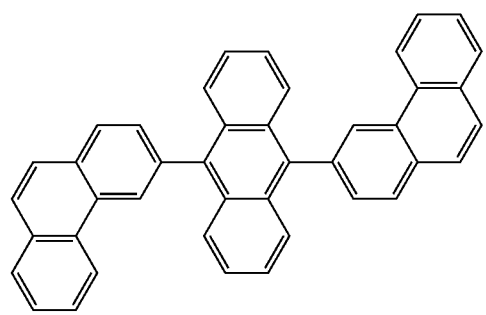
a-2
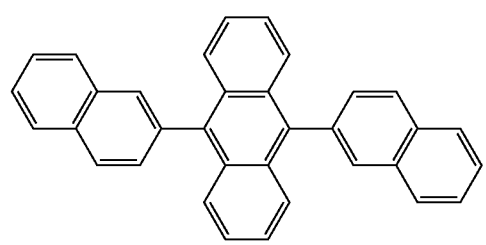
a-3
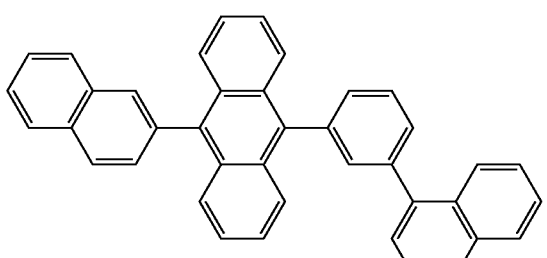
a-4
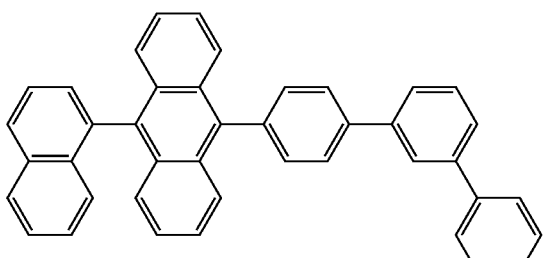
a-5
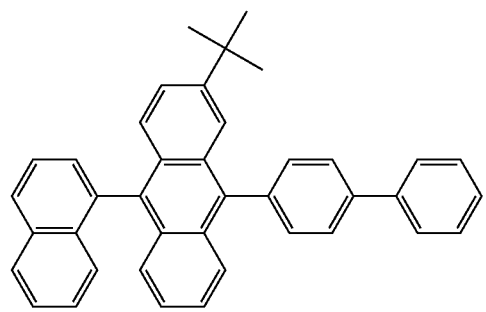
a-6
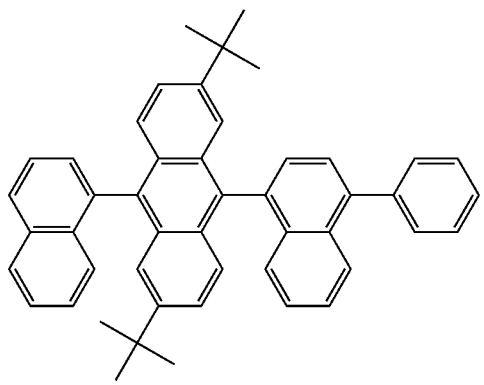
a-7
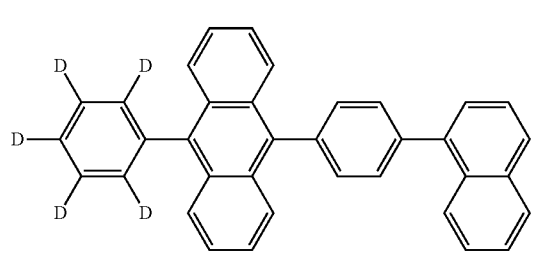
a-8
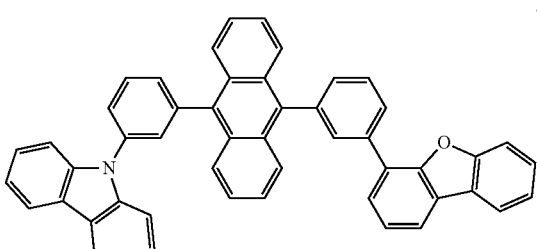
a-9
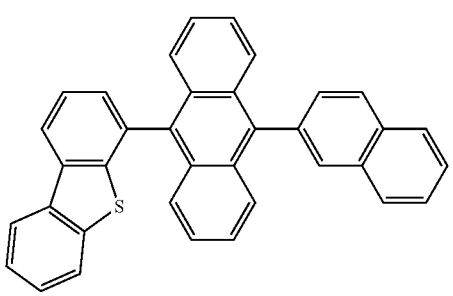
a-10
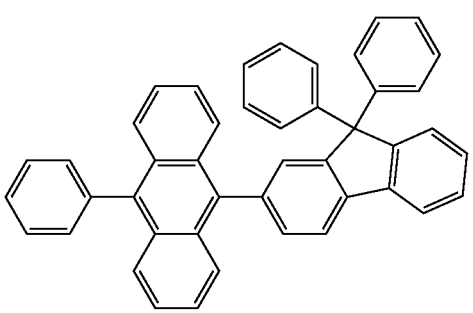

a-11

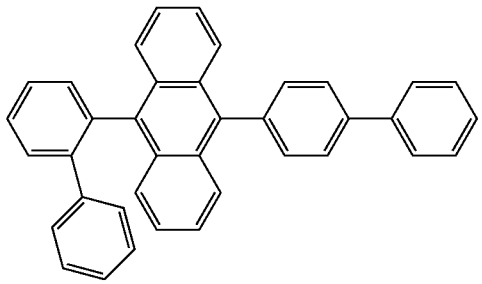

a-12

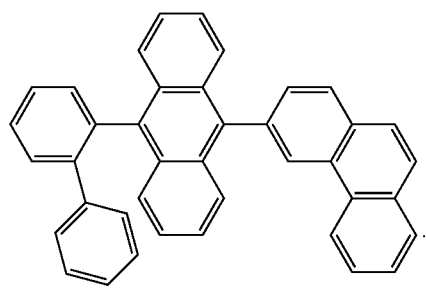

In addition, the emission layer 150, for example, may be formed of a styryl derivative (such as 1,4-bis[2-(3-N-ethylcarbazoryl)vinyl]benzene (BCzVB), 4-(di-p-tolylamino)-4'-[(di-p-tolylamino)styryl]stilbene (DPAVB), N-(4-((E)-2-(6-((E)-4-(diphenylamino)styryl)naphthalen-2-yl)vinyl)phenyl)-N-phenylbenzenamine (N-BDAVBi), etc.). The emission layer 150 may also be formed of, for example, a perylene derivative (for example, 2,5,8,11-tetra-t-butylperylene (TBPe), etc.) or a pyrene derivative (such as 1,1-dipyrene, 1,4-dipyrenylbenzene, 1,4-bis(N,N-diphenylamino)pyrene, etc.). However, embodiments of the present disclosure are not limited to the above example compounds.

The electron transport layer 160 is positioned on the emission layer 150. The electron transport layer 160 has the function of transporting electrons, and may have a thickness, for example, of about 15 nm to about 50 nm.

The electron transport layer 160 may be formed of any suitable electron transport material. The electron transport material may include, for example, tris(8-hydroxyquinolinato)aluminum (Alq3), or a compound that has a nitrogen-containing aromatic ring. Non-limiting examples of the compound that has a nitrogen-containing aromatic ring may include a compound which has a pyridine ring (such as 1,3,5-tri[(3-pyridyl)-phen-3-yl]benzene); a compound which has a triazine ring (such as 2,4,6-tris(3'-(pyridin-3-yl)biphenyl-3-yl)-1,3,5-triazine); and a compound which has a imidazole derivative (such as 2-(4-(N-phenylbenzoimidazolyl-1-ylphenyl)-9,10-dinaphthylanthracene), etc.

The electron injection layer 170 is positioned on the electron transport layer 160. The electron injection layer 170 has the function of allowing electrons to be easily injected from the second electrode 180, and may have a thickness of about 0.3 nm to about 9 nm. Any suitable material may be used to form the electron injection layer 170. For example, the electron injection layer 170 may be formed of a lithium (Li) complex (such as lithium 8-quinolinolato (Liq), lithium fluoride (LiF), etc.), sodium chloride (NaCl), cesium fluoride (CsF), lithium oxide ($Li_2O$), barium oxide (BaO), etc.

The second electrode 180 is positioned on the electron injection layer 170. The second electrode 180 may be, for example, a cathode, and may be formed as a reflective electrode using a metal, an alloy, or a conductive compound which has a low work function. The second electrode 180 may also be formed of, for example, a metal such as lithium (Li), magnesium (Mg), aluminum (Al), calcium (Ca), etc., or a mixture of metals such as aluminum-lithium (Al—Li), magnesium-indium (Mg—In), magnesium-silver (Mg—Ag), etc. Moreover, the second electrode 180 may also be formed as a transmissive electrode using a thin film of the metal material having a thickness up to about 20 nm, or using a transparent conductive film such as indium tin oxide, indium zinc oxide, etc.

Each of the above-described layers may be formed via an appropriate film forming method, such as vacuum deposition, sputtering, various coating methods, etc., according to the material to be used. Each organic layer positioned between the first electrode 120 and the second electrode 180 may be formed through various deposition methods, various coating methods, etc. In addition, each metal layer such as the first electrode 120 and the second electrode 180 may be formed, for example, through vacuum deposition, sputtering, etc.

In the above description of an example organic electroluminescent device 100, which includes the first monoamine derivative, the operating voltage is lowered and the emission efficiency is improved.

However, embodiments of the organic electroluminescent device 100 are not limited to the example structure as described above. Other embodiments may have various other known structures of organic electroluminescent devices. For example, the organic electroluminescent device 100 may exclude at least one of the hole injection layer 130, the hole transport layer 140, the electron transport layer 160, or the electron injection layer 170. Alternatively, additional layers may be further included. Each layer included in the organic electroluminescent device 100 may be formed as a single layer, or as multiple layers.

The organic electroluminescent device 100 may also include a hole blocking layer between the hole transport layer 140 and the emission layer 150 to prevent triplet excitons and holes from diffusing into the electron transport layer 160. The hole blocking layer may be formed of, for example, an oxadiazole derivative, a triazole derivative, a phenanthroline derivative, etc.

1-3. Examples

Hereinafter, embodiments of a first monoamine derivative and an organic electroluminescent device including the first monoamine derivative as represented by Formula 1 will be described in more detail with reference to Examples and Comparative Examples. However, the Examples given below are merely specific examples, and the monoamine derivative and organic electroluminescent device are not limited to the following Examples.

1-3-1. Synthesis of the First Monoamine Derivative

First, a method of synthesizing embodiments of the first monoamine derivative represented by Formula 1 will be described by providing Examples for synthetic methods of Compounds 1, 3, and 6, which are represented in the above Formula 2. However, the synthetic methods to be described below are merely examples, and methods of synthesizing monoamine derivatives according to the present embodiment are not limited to the examples given below.

Synthesis of Compound 1 Represented in Formula 2

Compound 1, a first monoamine derivative, was synthesized according to the following Reaction Formula 1:

(Reaction Formula 1)

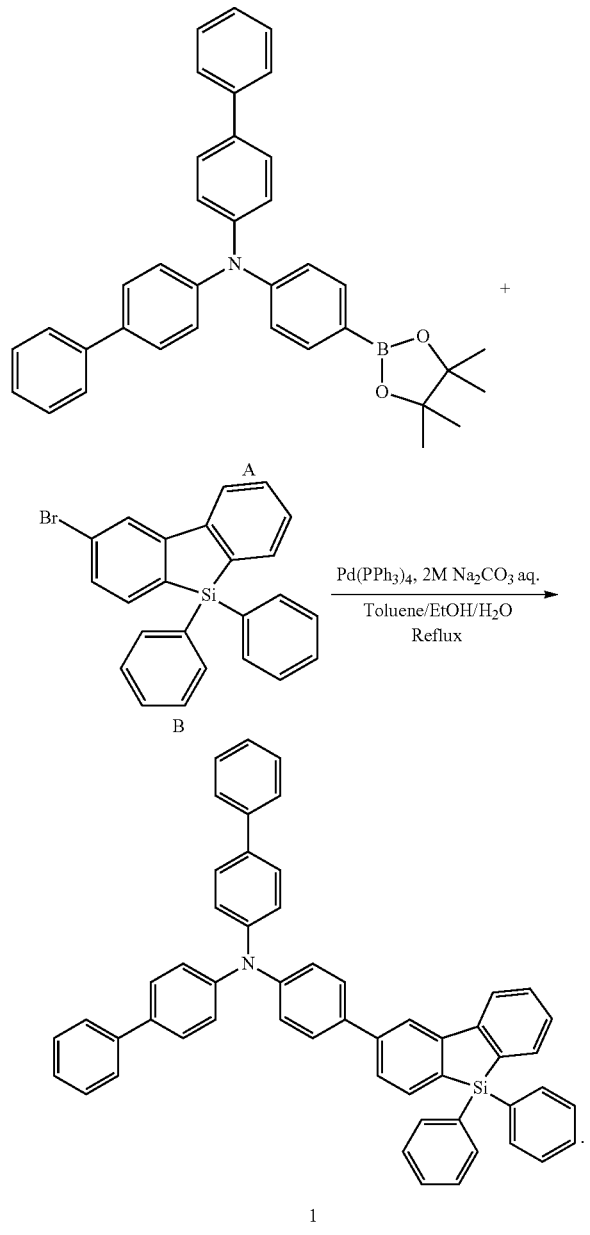

1.52 g (2.90 mmol) of Compound A, 1.00 g (2.42 mmol) of Compound B, 25 mL of toluene, 12 mL of ethanol, and 6 mL of a 2 M aqueous solution of sodium carbonate ($Na_2CO_3$) were added to a reaction vessel to produce a mixed solution, and the atmosphere of the reaction vessel was replaced with argon (Ar). 0.08 g (0.07 mmol) of $Pd(PPh_3)_4$ was added to the mixed solution, followed by stirring while heating and refluxing for 1.5 hours.

After cooling, the organic layer was extracted using a separatory funnel. The extracted organic layer was dried using anhydrous magnesium sulfate ($MgSO_4$) and then filtered. The filtrate was concentrated using a rotary evaporator to obtain a product. The obtained product was purified through silica gel column chromatography (eluent: toluene/hexane), and the purified solid was recrystallized using toluene/hexane to obtain 1.68 g (Yield 95%) of the target material, Compound 1, as a white solid powder.

The molecular weight of the obtained Compound 1 was measured using FAB-MS (Fast Atom Bombardment-Mass Spectrometry) to be 729.23 ($C_{54}H_{39}NSi$).

Synthesis of Compound 3 Represented in Formula 2

Compound 3, a first monoamine derivative, was synthesized according to the following Reaction Formula 2:

(Reaction Formula 2)

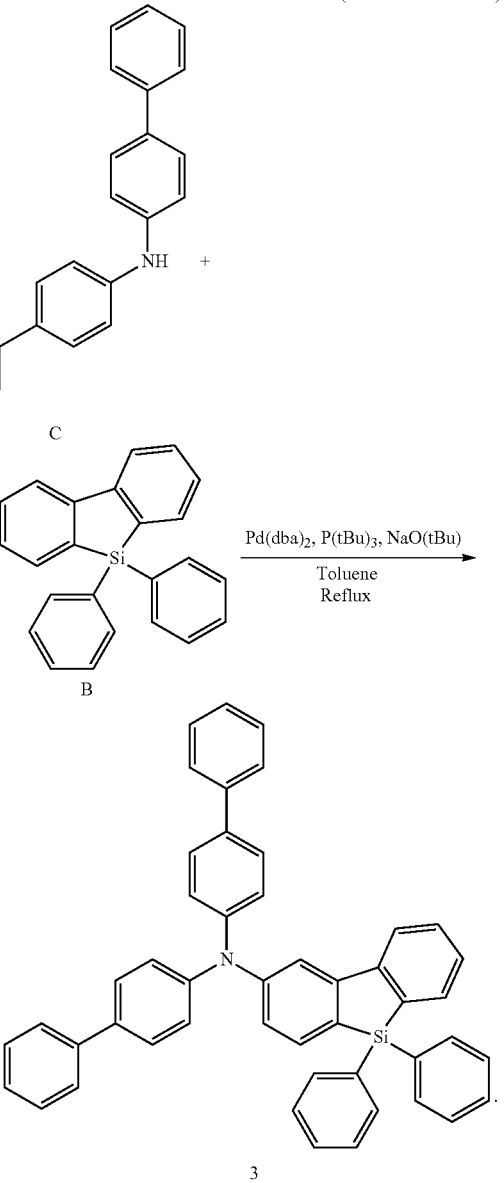

Under an argon atmosphere, 1.50 g (4.67 mmol) of Compound C, 2.32 g (5.60 mmol) of Compound B, 0.13 g (0.23 mmol) of bis(dibenzylideneacetone)palladium(0), and 0.90 g (9.33 mmol) of sodium tert-butoxide were added to a reaction vessel to produce a mixed solution. Next, 47 mL of anhydrous toluene and 0.62 mL (0.93 mmol) of a 1.5 M toluene solution of tri-tert-butylphosphine were added to the mixed solution, followed by heating and stirring at 100° C. for 1 hour.

After cooling in air, water was added, and the organic layer was washed and separated. The separated organic layer was dried using anhydrous magnesium sulfate and then filtered. The filtrate was concentrated using a rotary evaporator to obtain a product. The obtained product was purified through silica gel column chromatography (eluent: toluene/hexane), and the purified solid was recrystallized using toluene/hexane to obtain 2.84 g (Yield 93%) of the target material, Compound 3, as a white solid powder.

The molecular weight of the obtained Compound 3 was measured using FAB-MS to be 653.25 ($C_{48}H_{35}NSi$).

Synthesis of Compound 6 Represented in Formula 2

Next, Compound 6, a first monoamine derivative according to the present embodiment, was synthesized according to the following Reaction Formula 3:

(Reaction Formula 3)

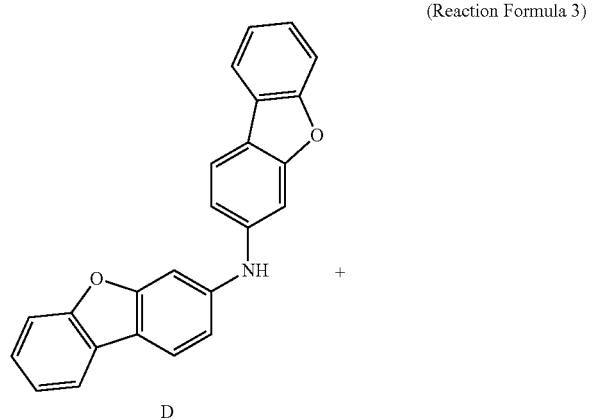

D

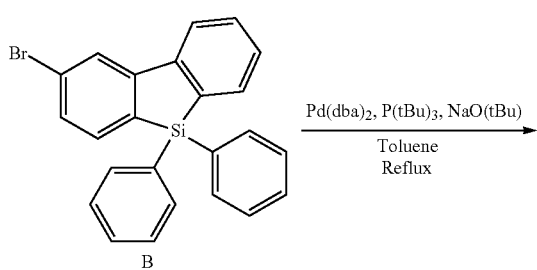

B

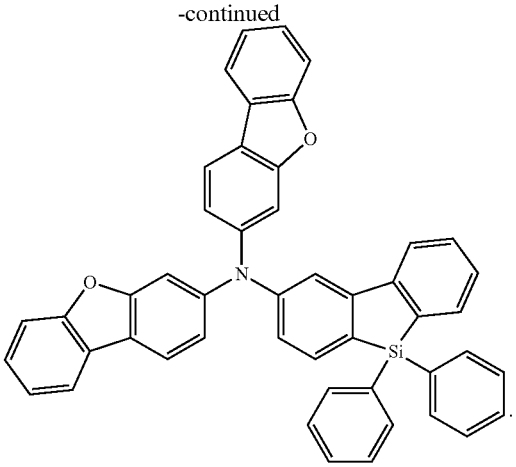

6

Under an argon atmosphere, 1.80 g (5.15 mmol) of Compound D, 2.56 g (6.18 mmol) of Compound B, 0.15 g (0.26 mmol) of bis(dibenzylideneacetone)palladium(0), and 0.99 g (10.30 mmol) of sodium tert-butoxide were added to a reaction vessel to produce a mixed solution. Next, 52 mL of anhydrous toluene and 0.69 mL (1.03 mmol) of a 1.5 M toluene solution of tri-tert-butylphosphine were added to the mixed solution, followed by heating and stirring at 100° C. for 1 hour.

After cooling in air, water was added, and the organic layer was washed and separated. The separated organic layer was dried using anhydrous magnesium sulfate and then filtered. The filtrate was concentrated using a rotary evaporator to obtain a product. The obtained product was purified through silica gel column chromatography (eluent: toluene/hexane), and the purified solid was recrystallized using toluene/hexane to obtain 3.09 g (Yield 88%) of the target material, Compound 6, as a white solid powder.

The molecular weight of the obtained Compound 6 was measured using FAB-MS to be 681.21 ($C_{48}H_{31}NO_2Si$).

1-3-2. Manufacturing of Organic Electroluminescent Device

Next, a blue light-emitting organic electroluminescent device which includes the first monoamine derivative represented by Formula 1 was manufactured through the following procedure using vacuum deposition.

Example 1-1

First, surface treatment using ultraviolet (UV) radiation and ozone ($O_3$) was performed on an ITO-glass substrate which was subjected to patterning and cleaning in advance. The ITO layer (as a first electrode) on the glass substrate was about 150 nm thick. The surface treated substrate was placed inside a glass bell jar type (e.g., bell jar) deposition apparatus for forming an organic film, and a hole injection layer, a hole transport layer, an emission layer, and an electron transport layer were successively deposited under a vacuum level of about $10^{-4}$ to about $10^{-5}$ Pa.

The hole injection layer was formed of 4,4',4"-tris(N,N-2-naphthylphenylamino)triphenylamine (2-TNATA) to have a thickness of about 60 nm. The hole transport layer was formed of Compound 1 to have a layer thickness of about 30 nm. The emission layer was formed using 9,10-di(2-naphthyl)anthracene (ADN) as a light-emitting host material and 2,5,8,11-tetra-t-butylperylene (TBP) as a dopant material, to have a layer thickness of about 25 nm. Moreover, the doping amount of the dopant material was about 3% by mass based on the total mass of the host material. The electron transport layer was formed of Alq3 to have a layer thickness of about 25 nm.

Next, the substrate was transferred to the glass bell jar type (e.g., bell jar) deposition apparatus for forming a metal layer, and an organic electroluminescent device was manufactured through deposition of an electron injection layer and a second electrode under a vacuum level of about $10^{-4}$ to about $10^{-5}$ Pa. Moreover, the electron injection layer was formed of lithium fluoride (LiF) to have a layer thickness of about 1 nm, and the second electrode was formed of aluminum (Al) to have a layer thickness of about 100 nm.

Example 1-2

An organic electroluminescent device was manufactured through the same method as that used in Example 1-1, except the hole transport layer was formed of Compound 3, which is represented in Formula 2.

Example 1-3

An organic electroluminescent device was manufactured through the same method as that used in Example 1-1, except the hole transport layer was formed of Compound 6 which is represented in Formula 2.

Comparative Example 1-1

An organic electroluminescent device was manufactured through the same method as that used in Example 1-1, except the hole transport layer was formed of the below Compound c1. The structure of Compound c1 differs from Compound 1, in that one of the covalent bonds forming a dibenzosilole ring is severed.

Comparative Example 1-2

An organic electroluminescent device was manufactured through the same method as that used in Example 1-1, except the hole transport layer was formed of the below Compound c2. Compound c2 is a widely known arylamine compound that is commonly used as a hole transport material.

Comparative Example 1-3

An organic electroluminescent device was manufactured through the same method as that used in Example 1-1, except the hole transport layer was formed of the below Compound c3. Compound c3 includes an additional carbazolyl group compared to Compound c1.

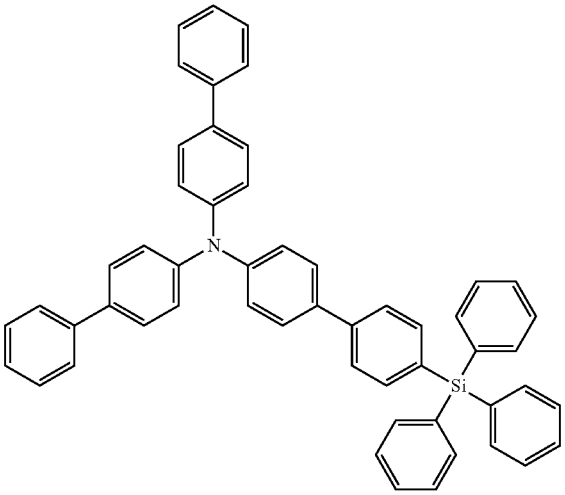
(Compound c1)

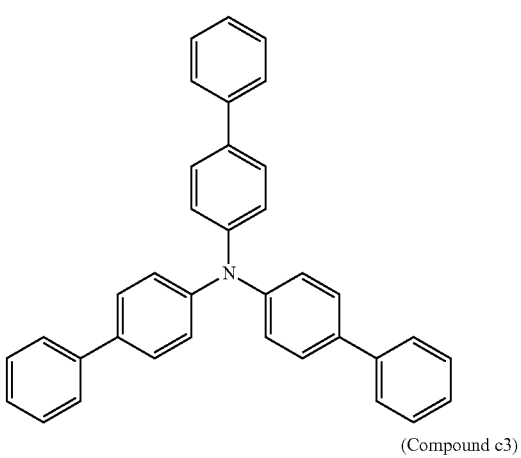
(Compound c2)

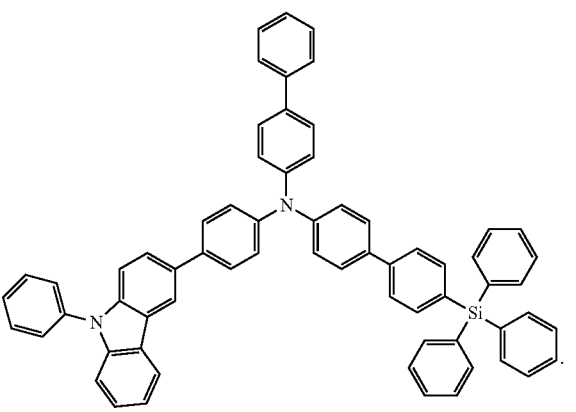
(Compound c3)

1-3-3. Evaluation Results

The evaluation results of organic electroluminescent devices manufactured according to Examples 1-1 to 1-3 and Comparative Examples 1-1 to 1-3 are shown in the below Table 1. A luminance distribution measurement device (C9920-11) produced by HAMAMATSU Photonics was used to evaluate the electroluminescent properties of the manufactured organic electroluminescent devices. The results shown in Table 1 were measured at a current density of about 10 mA/cm².

TABLE 1

|  | HTL | Operating Voltage [V] | Emission Efficiency [cd/A] |
|---|---|---|---|
| Example 1-1 | Compound 1 | 6.0 | 8.0 |
| Example 1-2 | Compound 3 | 6.3 | 7.3 |
| Example 1-3 | Compound 6 | 6.1 | 7.5 |
| Comparative Example 1-1 | Compound c1 | 7.2 | 6.5 |
| Comparative Example 1-2 | Compound c2 | 7.5 | 5.2 |
| Comparative Example 1-3 | Compound c3 | 6.7 | 6.9 |

According to Table 1, it can be seen that the organic electroluminescent devices of Examples 1-1 to 1-3, in which the hole transport layer is formed of variations of the first monoamine derivative, have a lower operating voltage and an improved emission efficiency when compared to Comparative Examples 1-1 to 1-3.

In particular, it can be seen that the organic electroluminescent devices of Examples 1-1 to 1-3, in which variations of the first monoamine derivative are used in the hole transport layer, have lower operating voltages and improved emission efficiencies when compared to Comparative Examples 1-1 and 1-3. The organic electroluminescent devices of Comparative Examples 1-1 and 1-3 contain Compounds c1 and c3 (where one of the covalent bonds forming a dibenzosilole is severed) in the hole transport layer. Moreover, the organic electroluminescent devices of Examples 1-1 to 1-3 also have lower operating voltages and improved emission efficiencies compared to Comparative Example 1-3. Comparative Example 1-3 uses Compound c3 in the hole transport layer, which includes an additional carbazolyl group when compared to Compound c1. Therefore, it can be seen that including a dibenzosilolyl group instead of a carbazolyl group (as in variations of the first monoamine derivative) may lower the operating voltage and improve the emission efficiency of an organic electroluminescent device.

In addition, it can be seen that the organic electroluminescent devices of Examples 1-1 to 1-3, in which variations of the first monoamine derivative represented by Formula 1 are used in the hole transport layer, have lower operating voltages and improved emission efficiencies when compared to Comparative Example 1-2, which includes Compound c2, a widely known arylamine derivative, in the hole transport layer.

For example, although arylamine compounds such as Compound c2 (used in Comparative Example 1-2) have a high hole transporting ability, the arylamine compounds have a shallow HOMO level and a large energy barrier against light-emitting materials in the emission layer. Moreover, although monoamine derivatives having a tetraphenylsilyl moiety have a deep HOMO level (such as Compounds c1 and c3, which were used in Comparative Examples 1-1 and 1-3), their hole transporting ability is low. The first monoamine derivative represented by Formula 1 includes a dibenzosilolyl group, and may thus have both a high hole transporting ability and a deep HOMO level. Consequently, the efficiency is good, and holes and electrons may be recombined in the emission layer.

As understood from the above results, when the first monoamine derivative represented by Formula 1 is included in an organic electroluminescent device, the operating voltage may be lowered and the emission efficiency may be improved. Thus, the first monoamine derivative may be suitably used as a material for organic electroluminescent devices, and in particular, may be suitably used as a hole transport and/or hole injection material.

2-1. Monoamine Derivative Represented By Formula 3

Hereinafter, the monoamine derivative represented by Formula 3 may be described as a second monoamine derivative.

First, a description will be given of the second monoamine derivative of an embodiment represented by the following Formula 3. The second monoamine derivative may be used as a hole transport and/or hole injection material in an organic electroluminescent device, and is represented by the following Formula 3:

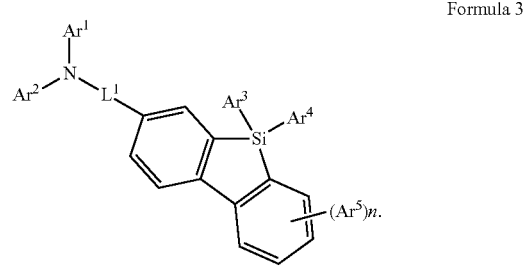

Formula 3

In Formula 3, $Ar^1$ and $Ar^2$ may each independently be selected from a substituted or unsubstituted aryl group having 6 to 50 carbon atoms for forming a ring, and a substituted or unsubstituted heteroaryl group having 5 to 50 carbon atoms for forming a ring; $Ar^a$ to $Ar^5$ may each independently be selected from hydrogen, deuterium, a halogen atom, a substituted or unsubstituted alkyl group having 1 to 20 carbon atoms, a substituted or unsubstituted aryl group having 6 to 50 carbon atoms for forming a ring, a substituted or unsubstituted heteroaryl group having 5 to 50 carbon atoms for forming a ring, and an aryl or heteroaryl group obtained through ring condensation with any adjacent substituent; n may be an integer from 0 to 4; and $L^1$ may be selected from a single bond, a substituted or unsubstituted arylene group having 6 to 18 carbon atoms for forming a ring, and a substituted or unsubstituted heteroarylene group having 5 to 15 carbon atoms for forming a ring.

Moreover, in the above Formula 3, all amino groups are excluded from the scope of substituents which may be included in $Ar^1$ to $Ar^5$. That is, the compounds represented by Formula 3 are monoamine derivatives containing only one amino moiety.

Generally, the second monoamine derivative represented by Formula 3 contains a dibenzosilolyl moiety, and thus has a deeper highest occupied molecular orbital (HOMO) level (e.g., the absolute value of the energy of the HOMO level becomes larger) than an analogous diamine derivative having arylamino groups connected to both sides thereof.

When a compound having a shallow HOMO level (e.g., having a small absolute value of the energy of the HOMO level) such as a diamine derivative, etc. is used in the hole transport layer, the energy barrier against the light-emitting material in the emission layer is often large, the amount of holes transported to the emission layer may be reduced, and the emission efficiency of the organic electroluminescent device is often decreased. In particular, most blue light-emitting materials have a deep HOMO level. Therefore, when a compound having a shallow HOMO level is used in the hole transport layer, the energy gap between the HOMO level of the hole transport layer material and the blue light-emitting material in the emission layer becomes large, and thus the emission efficiency is often decreased.

Since the second monoamine derivative represented by Formula 3 may have a deeper HOMO level than the diamine derivative having a structure analogous to the monoamine derivative, the energy barrier against the light-emitting material in the emission layer may be small. Thus, by using the second monoamine derivative represented by Formula 3, the operating voltage may be lowered and the emission efficiency may be improved in an organic electroluminescent device.

In particular, when the emission layer includes a blue light-emitting material and/or a green light-emitting material, the second monoamine derivative represented by Formula 3 may suitably reduce the operating voltage and improve the emission efficiency in an organic electroluminescent device.

The second monoamine derivative represented by Formula 3 may be included in at least one of the layers positioned between the emission layer and the anode in an organic electroluminescent device. Specifically, the second monoamine derivative represented by Formula 3 may be included in the hole transport layer and/or the hole injection layer.

However, in an organic electroluminescent device, layers which include the second monoamine derivative represented by Formula 3 are not limited to the examples given above. For example, the second monoamine derivative represented by Formula 3 may be included in any of the organic layers positioned between the anode and cathode of an organic electroluminescent device, and for example, may be included in the emission layer.

In Formula 3, $Ar^1$ and $Ar^2$ may each independently be selected from a substituted or unsubstituted aryl group having 6 to 18 carbon atoms for forming a ring, and a substituted or unsubstituted heteroaryl group having 5 to 12 carbon atoms for forming a ring. Moreover, $Ar^1$ and $Ar^2$ may each independently be selected from a biphenyl group and a terphenyl group.

When $Ar^1$ and $Ar^2$ are such substituents as described above, the second monoamine derivative represented by Formula 3 may reduce the operating voltage and improve the emission efficiency of an organic electroluminescent device, as will be described in examples below.

In Formula 3, $Ar^3$ to $Ar^5$ may each independently be selected from a halogen atom, a substituted or unsubstituted alkyl group having 1 to 5 carbon atoms, and a substituted or unsubstituted aryl group having 6 to 12 carbon atoms for forming a ring. Moreover, $Ar^3$ and $Ar^4$ may each independently be selected from a methyl group or a phenyl group.

When $Ar^3$ to $Ar^5$ are such substituents as described above, the second monoamine derivative represented by Formula 3 may reduce the operating voltage and improve the emission efficiency of an organic electroluminescent device, as will be described in examples below.

In the above Formula 3, $L^1$ may be selected from a single bond, a phenylene group, and a biphenylene group.

When $L^1$ is such a substituent as described above, the second monoamine derivative represented by Formula 3 may reduce the operating voltage and improve the emission efficiency of an organic electroluminescent device, as will be described in examples below.

In the above Formula 3, non-limiting examples of an aryl group or a heteroaryl group may include a phenyl group, a biphenyl group, a terphenyl group, a naphthyl group, an anthryl group, a phenanthrenyl group, a fluorenyl group, an indenyl group, a pyrenyl group, a fluoranthenyl group, a triphenylenyl group, a pyrazinyl group, a pyrrolyl group, a pyridyl group, a pyrimidyl group, a pyridazyl group, a pyrazinyl group, a furanyl group, a pyranyl group, a thienyl group, a quinolyl group, an isoquinolyl group, a benzofuranyl group, a benzothienyl group, an indolyl group, a benzoxazolyl group, a benzothiazolyl group, a quinoxalyl group, a benzoimidazolyl group, a pyrazolyl group, a tetrazolyl group, an imidazolyl group, an oxazolyl group, an isoxazolyl group, a thiazolyl group, an isothiazolyl group, a carbazolyl group, a dibenzofuranyl group, a dibenzothienyl group, etc.

In the above Formula 3, non-limiting examples of an alkyl group may include a straight-chain alkyl group (such as a methyl group, an ethyl group, a propyl group, a butyl group, an octyl group, a decyl group, a pentadecyl group, etc.), and a branched chain alkyl group (such as a t-butyl group, etc.).

In Formula 3, a halogen atom may be selected from a fluorine, a chlorine, a bromine, an iodine, etc.

In Formula 3, non-limiting examples of an arylene group and a heteroarylene group may include divalent groups in which one hydrogen is additionally removed from the aryl and heteroaryl groups described above.

Specific embodiments of the second monoamine derivative represented by the above-described Formula 3 may be shown as structural formulas of Compounds 1 to 20 which are represented in Formula 4, below. However, examples of the second monoamine derivative according to the present embodiment are not limited to the following compounds:

Formula 4

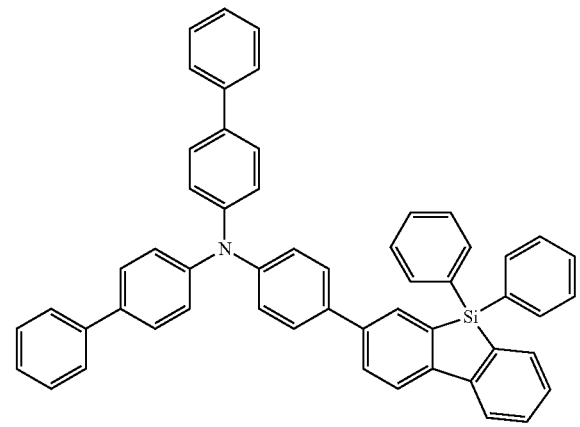

1

-continued
2
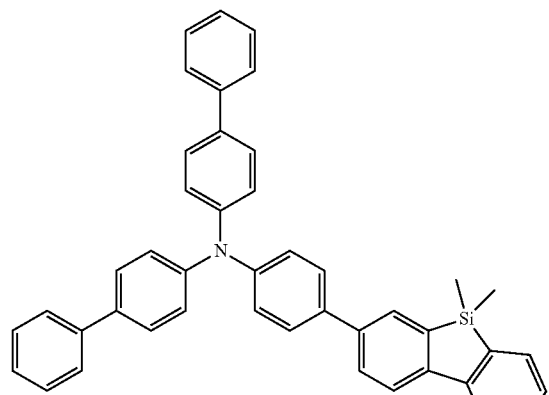
3
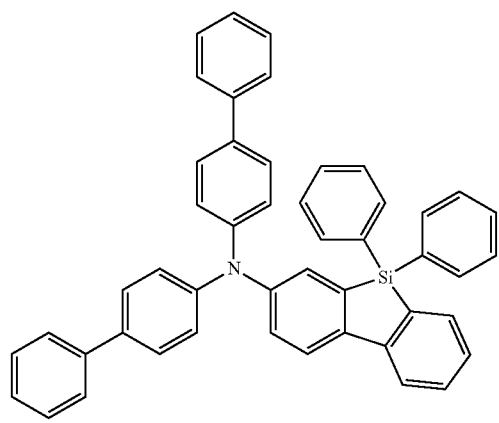
4
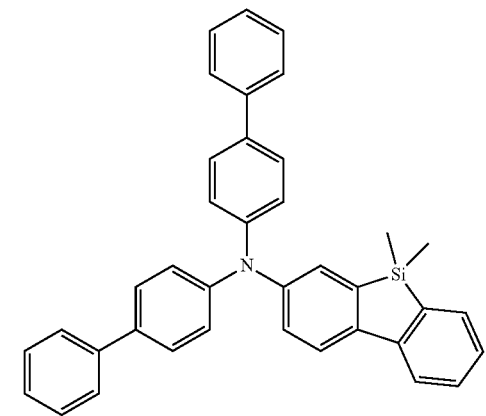
5
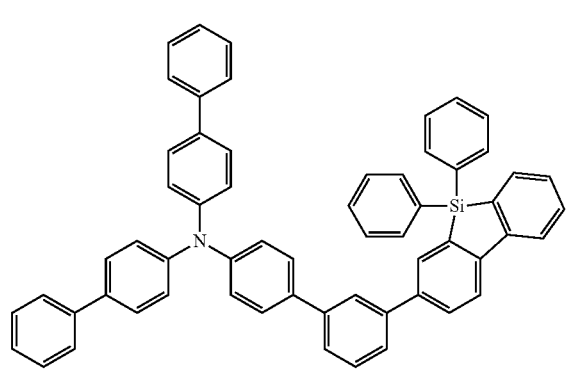
-continued
5
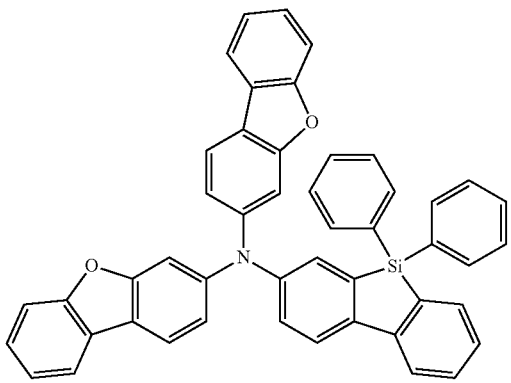
6
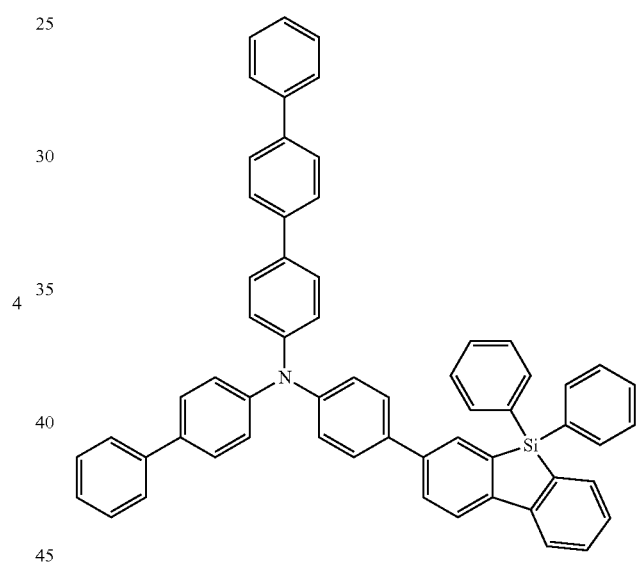
7
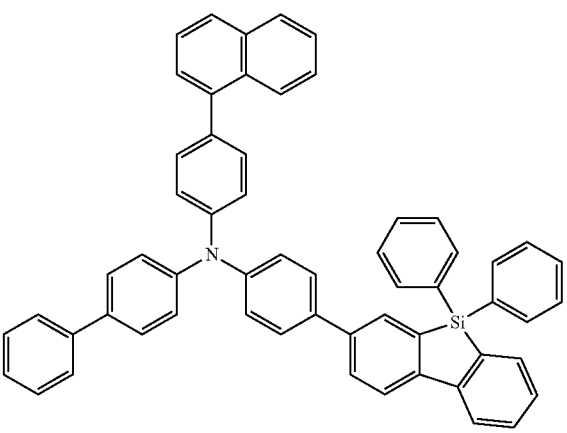

9
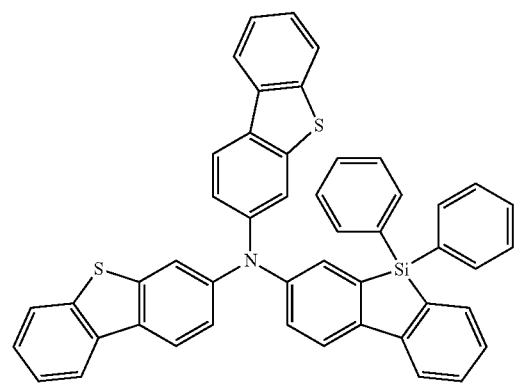
10
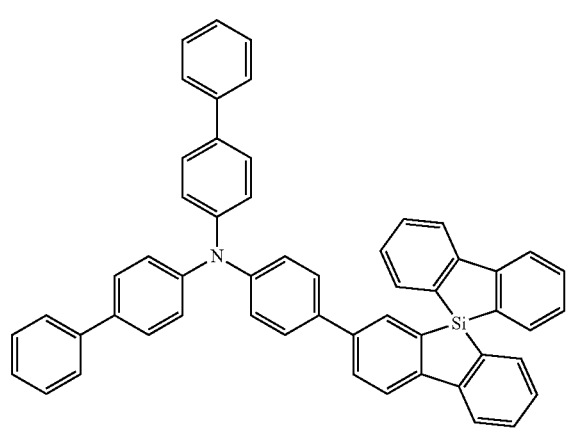
11
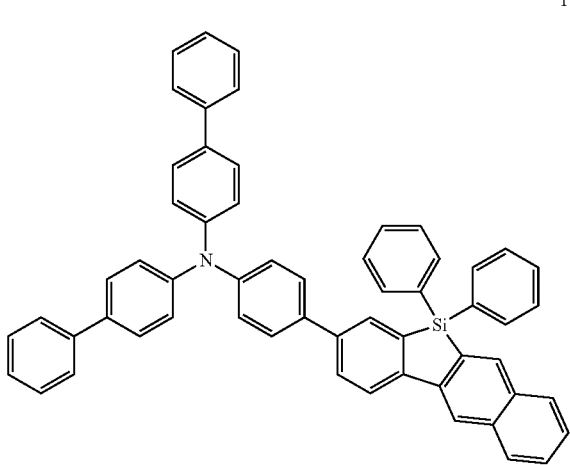
12
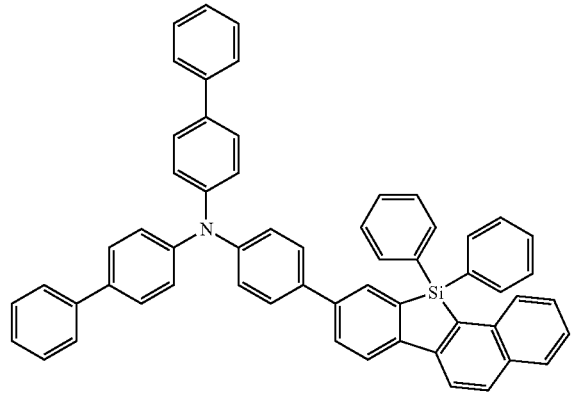
13
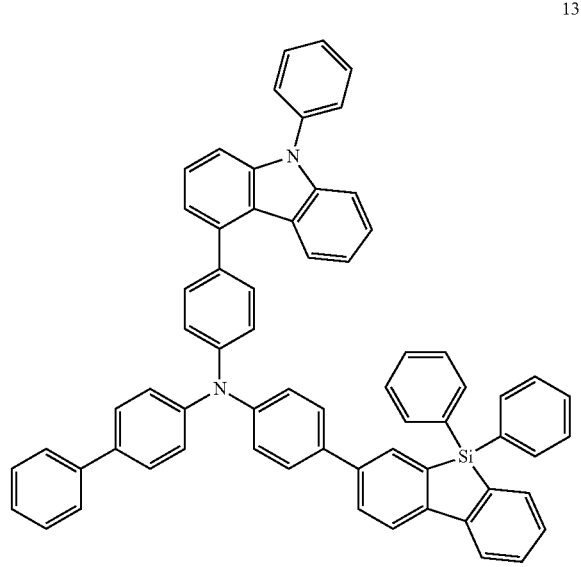
14
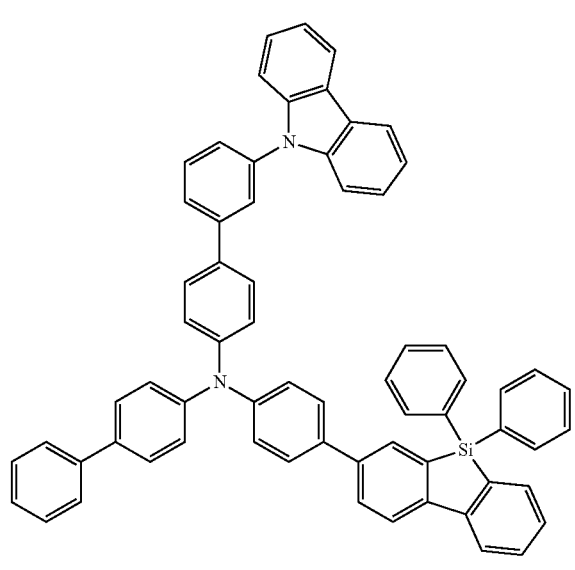

15

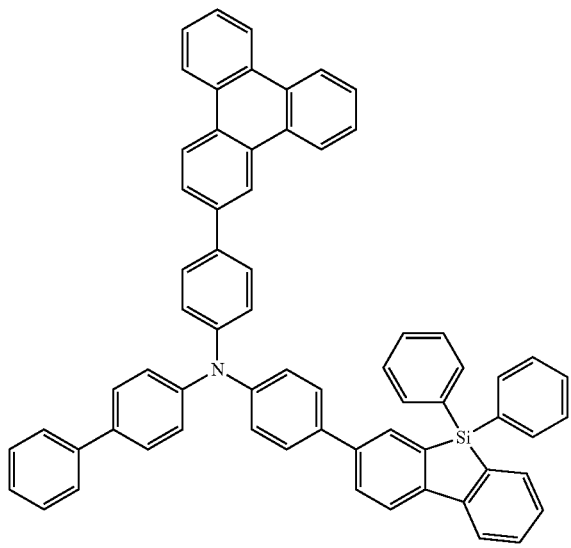

16

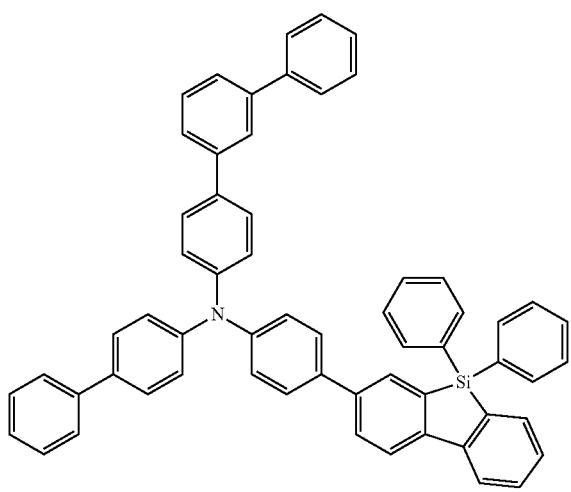

17

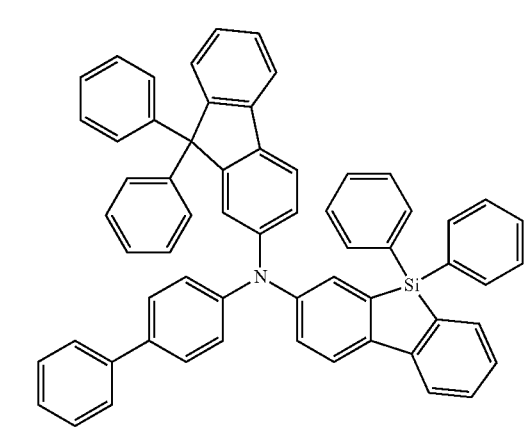

18

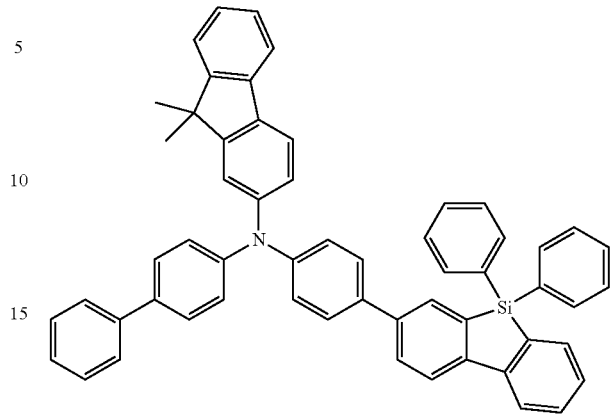

19

19

20

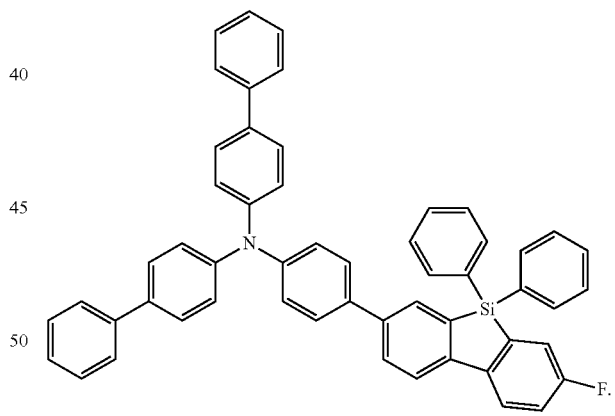

The second monoamine derivative represented by Formula 3 as described above may be used as a hole transport material and/or a hole injection material. In addition, since the second monoamine derivative according to the present embodiment may cause the HOMO level to be deeper and the energy barrier against the light-emitting material in the emission layer to be smaller, the operating voltage may be lowered and the emission efficiency may be improved in an organic electroluminescent device.

As above, an embodiment of the second monoamine derivative represented by Formula 3 will now be described in more detail.

2-2. An Organic Electroluminescent Device of an Embodiment Which Includes the Monoamine Derivative Represented By Formula 3

Hereinafter, the monoamine derivative represented by Formula 3 may be described as the second monoamine derivative.

Referring to the drawing, a detailed description will be given of an organic electroluminescent device which includes the second monoamine derivative according to the present embodiment. The drawing is a schematic diagram illustrating an example of the organic electroluminescent device according to the present embodiment.

As illustrated in the drawing, an organic electroluminescent device 100 according to the present embodiment includes a substrate 110, a first electrode 120 on the substrate 110, a hole injection layer 130 on the first electrode 120, a hole transport layer 140 on the hole injection layer 130, an emission layer 150 on the hole transport layer 140, an electron transport layer 160 on the emission layer 150, an electron injection layer 170 on the electron transport layer 160, and a second electrode 180 on the electron injection layer 170.

The organic electroluminescent device that includes the second monoamine derivative may have the same structure as the above-described organic electroluminescent device that includes the first monoamine derivative. Structures of the substrate 110, the first electrode 120, the electron transport layer 160, the electron injection layer 170, and the second electrode 180 have been previously described and will not be described again. Hereinafter, detailed descriptions are given of the hole injection layer 130, the hole transport layer 140, and the emission layer 150.

The hole injection layer 130 may be positioned on the first electrode 120. The hole injection layer 130 has the function of allowing holes to be easily injected from the first electrode 120 and may have a thickness of, for example, about 10 nm to about 150 nm.

The hole injection layer 130 may be formed of the monoamine derivative according to the present embodiment, and may also be formed of any suitable hole injection material. The hole injection material used to form the hole injection layer 130 may include, for example, triphenylamine-containing poly ether ketone (TPAPEK), 4-isopropyl-4'-methyldiphenyliodoniumtetrakis(pentafluorophenyl)borate (PPBI), N,N'-diphenyl-N,N'-bis-[4-(phenyl-m-tolyl-amino)-phenyl]-biphenyl-4,4'-diamine (DNTPD), a phthalocyanine compound such as copper phthalocyanine, 4,4',4''-tris(3-methylphenylphenylamino)triphenylamine (m-MTDATA), N,N'-di(1-naphthyl)-N,N'-diphenylbenzidine (NPB), 4,4', 4''-tris{N,N-diphenylamino}triphenylamine (TDATA), 4,4', 4''-tris(N,N-2-naphthylphenylamino)triphenylamine (2-TNATA), polyaniline/dodecylbenzenesulfonic acid (PANI/DBSA), poly(3,4-ethylenedioxythiophene)/poly(4-styrenesulfonate) (PEDOT/PSS), polyaniline/camphorsulfonic acid (PANI/CSA), polyaniline/poly(4-styrenesulfonate) (PANI/PSS), etc.

The hole transport layer 140 is positioned on the hole injection layer 130. The hole transport layer 140 has the function of transporting holes and may have a thickness of, for example, about 10 nm to about 150 nm. The hole transport layer 140 may have a multilayered structure.

Here, the hole transport layer 140 may be formed of the second monoamine derivative according to the present embodiment. However, when the second monoamine derivative is included in another layer (for example, the hole injection layer 130, and/or the emission layer 150), the hole transport layer 140 may be formed of any suitable hole transport material. The hole transport material may include, for example, 1,1-bis[(di-4-tolylamino)phenyl]cyclohexane (TAPC); a carbazole derivative such as N-phenyl carbazole or polyvinyl carbazole; N,N'-bis(3-methylphenyl)-N,N'-diphenyl-[1,1-biphenyl]-4,4'-diamine (TPD); 4,4', 4''-tris(N-carbazolyl)triphenylamine (TCTA); N,N'-di(1-naphthyl)-N,N'-diphenylbenzidine (NPB), etc.

The emission layer 150 is positioned on the hole transport layer 140. The emission layer 150 may emit light through fluorescence, phosphorescence, etc., and may have a thickness of, for example, about 10 nm to about 60 nm. Any suitable light-emitting material may be used as the light-emitting material in the emission layer 150. Non-limiting examples of the light-emitting material may include a fluoranthene derivative, a styryl derivative, a pyrene derivative, an arylacetylene derivative, a fluorene derivative, a perylene derivative, a chrysene derivative, etc. Moreover, a styryl derivative, a pyrene derivative, a perylene derivative, or an anthracene derivative may be used. For example, an anthracene derivative represented by the following Formula 5 may be used as a material of the emission layer 150:

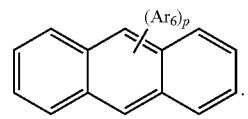

Formula 5

In the above Formula 5, each $Ar_6$ may independently be selected from hydrogen, deuterium, a substituted or unsubstituted alkyl group having 1 to 50 carbon atoms, a substituted or unsubstituted cycloalkyl group having 3 to 50 carbon atoms for forming a ring, a substituted or unsubstituted alkoxy group having 1 to 50 carbon atoms, a substituted or unsubstituted aralkyl group having 7 to 50 carbon atoms, a substituted or unsubstituted aryloxy group having 6 to 50 carbon atoms for forming a ring, a substituted or unsubstituted arylthio group having 6 to 50 carbon atoms for forming a ring, a substituted or unsubstituted alkoxycarbonyl group having 2 to 50 carbon atoms, a substituted or unsubstituted aryl group having 6 to 50 carbon atoms for forming a ring, a substituted or unsubstituted heteroaryl group having 5 to 50 atoms for forming a ring, a substituted or unsubstituted silyl group, a carboxyl group, a halogen atom, a cyano group, a nitro group, and a hydroxyl group; and p may be an integer from 1 to 10.

Specifically, each $Ar_6$ may independently be selected from a phenyl group, a biphenyl group, a terphenyl group, a naphthyl group, an anthryl group, a phenanthryl group, a fluorenyl group, an indenyl group, a pyrenyl group, an acetonaphthenyl group, a fluoranthenyl group, a triphenylenyl group, a pyridyl group, a furanyl group, a pyranyl group, a thienyl group, a quinolyl group, an isoquinolyl group, a benzofuranyl group, a benzothienyl group, an indolyl group, a carbazolyl group, a benzoxazolyl group, a benzothiazolyl group, a quinoxalyl group, a pyrazolyl group, a dibenzofuranyl group, and a dibenzothienyl group, etc. In addition, each $Ar_6$ may be selected from a phenyl group, a biphenyl group, a terphenyl group, a fluorenyl group, a carbazolyl group, and a dibenzofuranyl group, etc.

The compounds represented by the above Formula 5 may include, for example, Compounds a-1 to a-12, which are represented below. The compounds represented by Formula 5 are not limited to the following Compounds a-1 to a-12:

a-1
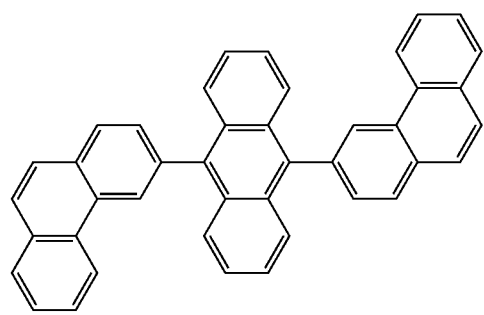
a-2
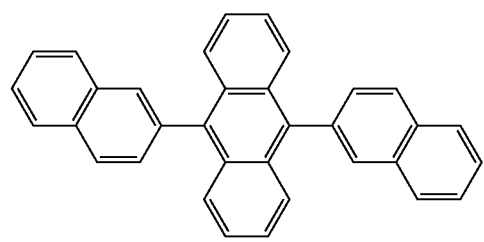
a-3
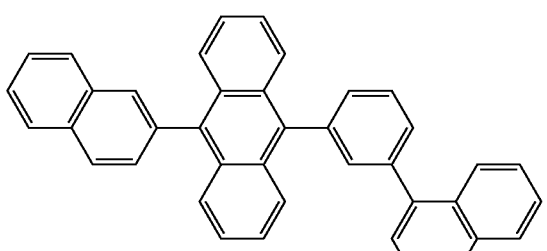
a-4
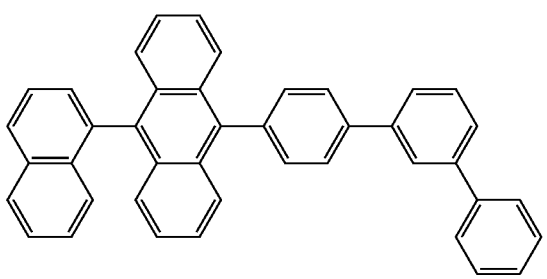
a-5
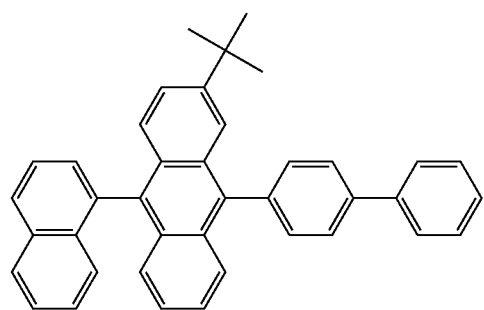
a-6
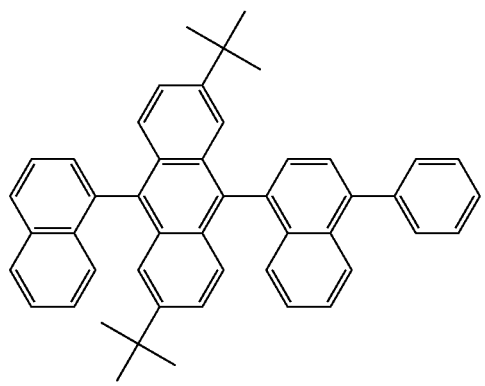
a-7
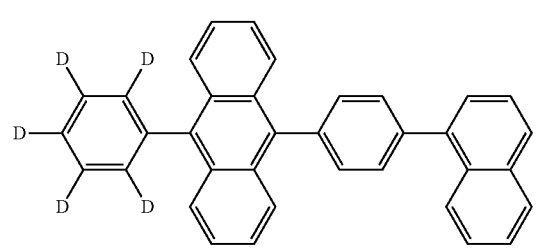
a-8
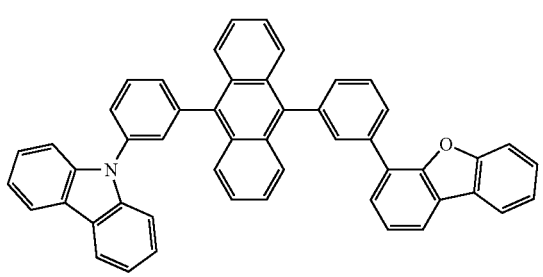
a-9
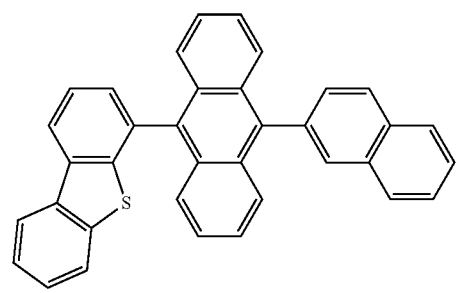
a-10
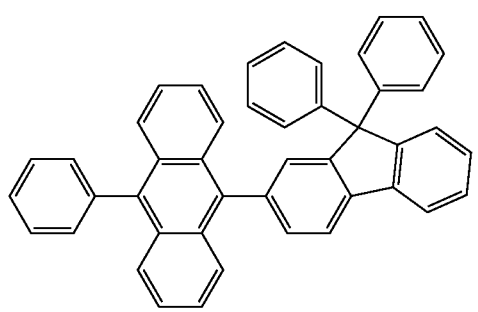

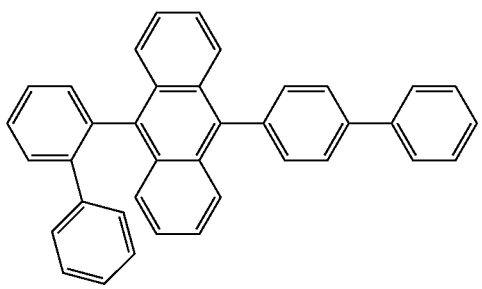

a-11

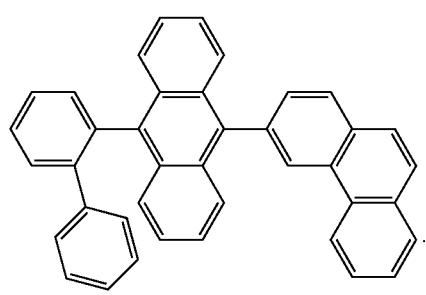

a-12

In addition, the emission layer 150, for example, may be formed of a styryl derivative (such as 1,4-bis[2-(3-N-ethylcarbazoryl)vinyl]benzene (BCzVB), 4-(di-p-tolylamino)-4'-[(di-p-tolylamino)styryl]stilbene (DPAVB), N-(4-((E)-2-(6-((E)-4-(diphenylamino)styryl)naphthalen-2-yl)vinyl)phenyl)-N-phenylbenzenamine (N-BDAVBi), etc.). The emission layer 150 may also be formed of, for example, a perylene derivative (for example, 2,5,8,11-tetra-t-butylperylene (TBPe), etc.) or a pyrene derivative such as 1,1-dipyrene, 1,4-dipyrenylbenzene, 1,4-bis(N,N-diphenylamino)pyrene, etc. However, embodiments of the present disclosure are not limited to the above example compounds.

As above, a description was given of an example of the organic electroluminescent device 100 according to the present embodiment. The operating voltage is lowered and the emission efficiency is improved in the organic electroluminescent device 100 which includes the second monoamine derivative according to an embodiment of the present disclosure.

However, structures of the organic electroluminescent device 100 are not limited to the example as described above. The organic electroluminescent device 100 may also have various other suitable structures of organic electroluminescent devices. For example, the organic electroluminescent device 100 may exclude at least one layer selected from the hole injection layer 130, the hole transport layer 140, the electron transport layer 160, and the electron injection layer 170. Alternatively, additional layers may be further included. Each layer included in the organic electroluminescent device 100 may be formed as a single layer, or as multiple layers.

The organic electroluminescent device 100 may also include a hole blocking layer between the hole transport layer 140 and the emission layer 150 to prevent or block triplet excitons and holes from diffusing into the electron transport layer 160. The hole blocking layer may be formed of, for example, an oxadiazole derivative, a triazole derivative, a phenanthroline derivative, etc.

2-3. Examples

Hereinafter, embodiments of a second monoamine derivative and an organic electroluminescent device including the second monoamine derivative will be described in more detail with reference to Examples and Comparative Examples.

However, the Examples given below are merely specific examples, and the monoamine derivative and organic electroluminescent device according to the present embodiment are not limited to the below-given Examples.

2-3-1. Synthesis of Second Monoamine Derivative Represented by Formula 3

First, a method of synthesizing the second monoamine derivative according to the present embodiment will be specifically described by providing Examples for synthetic methods of Compounds 1, 3, and 17, which are represented in the above Formula 4. However, the synthetic methods to be described below are merely examples, and methods of synthesizing the second monoamine derivative according to an embodiment of the present disclosure are not limited to examples given below.

Synthesis of Compound 1 Represented By Formula 4

Compound 1, a second monoamine derivative according to the present embodiment, was synthesized according to the following Reaction Formula 4:

Reaction Formula 4

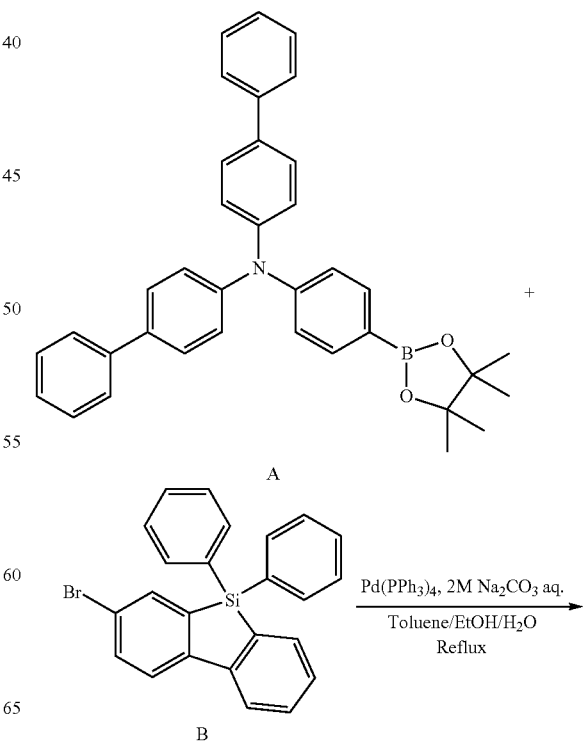

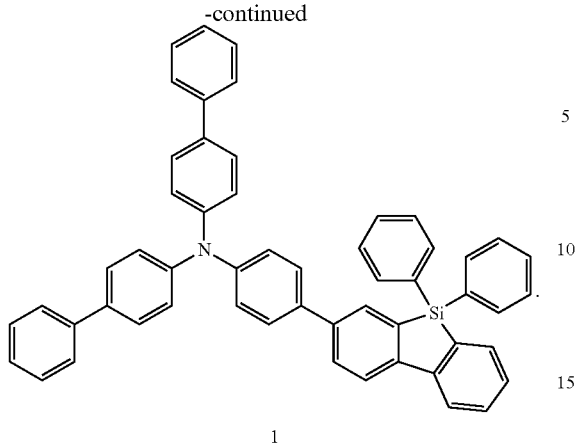

1

1.52 g (2.90 mmol) of Compound A, 1.00 g (2.42 mmol) of Compound B, 25 mL of toluene, 12 mL of ethanol, and 6 mL of a 2 M aqueous solution of sodium carbonate (Na$_2$CO$_3$) were added to a reaction vessel to produce a mixed solution, and the atmosphere of the reaction vessel was replaced with argon (Ar). 0.08 g (0.07 mmol) of Pd(PPh$_3$)$_4$ was added to the mixed solution, followed by stirring, while heating and refluxing, for 1.5 hours.

After cooling, the organic layer was extracted using a separatory funnel. The extracted organic layer was dried using anhydrous magnesium sulfate (MgSO$_4$) and then filtered. The filtrate was concentrated using a rotary evaporator to obtain a product. The obtained product was purified through silica gel column chromatography (eluent: toluene/hexane), and the purified solid was recrystallized using toluene/hexane to obtain 1.60 g (Yield 90%) of the target material, Compound 1, as a white solid powder.

The molecular weight of the obtained Compound 1 was measured through FAB-MS (Fast Atom Bombardment-Mass Spectrometry) to be 729.29 (C$_{54}$H$_{39}$NSi).

Synthesis of Compound 3 Represented By Formula 4

Compound 3, a second monoamine derivative according to the present embodiment, was synthesized according to the following Reaction Formula 5:

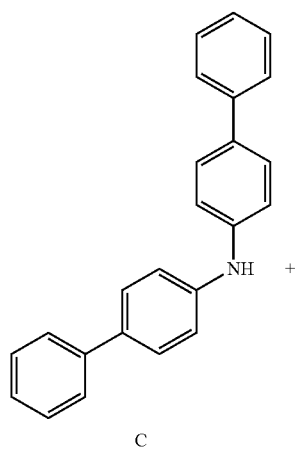

C

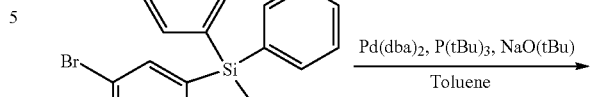

B

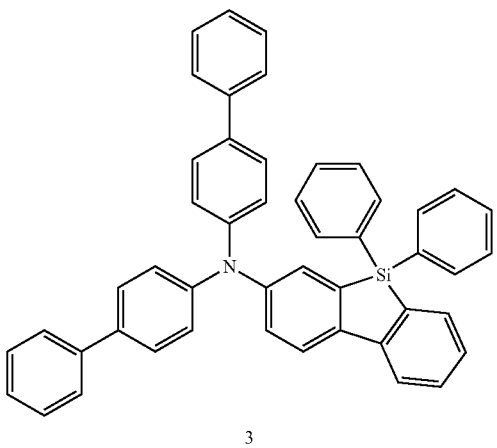

3

Under an argon atmosphere, 1.00 g (3.11 mmol) of Compound C, 1.54 g (3.73 mmol) of Compound B, 0.09 g (0.16 mmol) of bis(dibenzylideneacetone)palladium(0), and 0.60 g (6.22 mmol) of sodium tert-butoxide were added to a reaction vessel to produce a mixed solution. Next, 31 mL of anhydrous toluene and 0.41 mL (0.62 mmol) of a 1.5 M toluene solution of tri-tert-butylphosphine were added to the mixed solution, followed by heating and stirring at 100° C. for 1 hour.

After cooling in air, water was added, and the organic layer was washed and separated. The separated organic layer was dried using anhydrous magnesium sulfate and then filtered. The filtrate was concentrated using a rotary evaporator to obtain a product. The obtained product was purified through silica gel column chromatography (eluent: toluene/hexane), and the purified solid was recrystallized using toluene/hexane to obtain 1.93 g (Yield 95%) of the target material, Compound 3, as a white solid powder.

The molecular weight of the obtained Compound 3 was measured through FAB-MS to be 653.25 (C$_{48}$H$_{35}$NSi).

Synthesis of Compound 17 Represented By Formula 4

Next, Compound 17, a second monoamine derivative according to the present embodiment, was synthesized according to the following Reaction Formula 6:

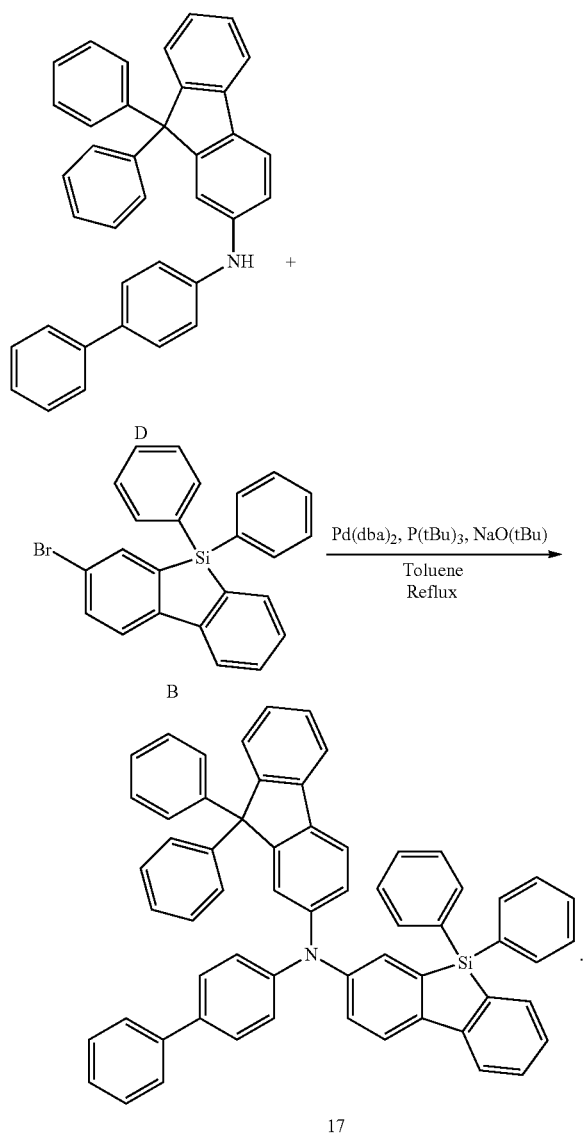

Under an argon atmosphere, 1.80 g (3.71 mmol) of Compound D, 1.84 g (4.45 mmol) of Compound B, 0.11 g (0.19 mmol) of bis(dibenzylideneacetone)palladium(0), and 0.71 g (7.41 mmol) of sodium tert-butoxide were added to a reaction vessel to produce a mixed solution. Next, 37 mL of anhydrous toluene and 0.49 mL (0.74 mmol) of a 1.5 M toluene solution of tri-tert-butylphosphine were added to the mixed solution, followed by heating and stirring at 100° C. for 1 hour.

After cooling in air, water was added, and the organic layer was washed and separated. The separated organic layer was dried using anhydrous magnesium sulfate and then filtered. The filtrate was concentrated using a rotary evaporator to obtain a product. The obtained product was purified through silica gel column chromatography (eluent: toluene/hexane), and the purified solid was recrystallized using toluene/hexane to obtain 2.52 g (Yield 83%) of the target material, Compound 17, as a white solid powder.

The molecular weight of the obtained Compound 17 was measured through FAB-MS to be 817.32 ($C_{61}H_{43}NSi$).

2-3-2. Manufacturing of Organic Electroluminescent Device

Next, a blue light-emitting organic electroluminescent device which includes the second monoamine derivative according to the present embodiment was manufactured through the following procedure using vacuum deposition.

Example 2-1

First, surface treatment using ultraviolet (UV) radiation and ozone ($O_3$) was performed on an ITO-glass substrate which was subjected to patterning and cleaning. The ITO layer (as the first electrode) on the ITO-glass substrate was about 150 nm thick. The surface treated substrate was placed inside a glass bell jar type (e.g., glass bell jar) deposition apparatus for forming an organic film, and a hole injection layer, a hole transport layer, an emission layer, and an electron transport layer were successively deposited under a vacuum level of about $10^{-4}$ to about $10^{-5}$ Pa.

The hole injection layer was formed of 4,4',4''-tris(N,N-2-naphthylphenylamino)triphenylamine (2-TNATA) to a thickness of about 60 nm. The hole transport layer was formed of Compound 1 to a thickness of about 30 nm. The emission layer was formed using 9,10-di(2-naphthyl)anthracene (ADN) as a light-emitting host material and 2,5,8,11-tetra-t-butylperylene (TBP) as a dopant material, to a thickness of about 25 nm. Moreover, the doping amount of the dopant material was about 3% by mass based on the total mass of the host material. The electron transport layer was formed of $Alq_3$ to have a layer thickness of about 25 nm.

Next, the substrate was transferred to the glass bell jar type (e.g., glass bell jar) deposition apparatus for forming a metal layer, and an organic electroluminescent device was manufactured through deposition of an electron injection layer and a second electrode under a vacuum level of about $10^{-4}$ to about $10^{-5}$ Pa. Moreover, the electron injection layer was formed of lithium fluoride (LiF) to a thickness of about 1 nm, and the second electrode was formed of aluminum (Al) to a layer thickness of about 100 nm.

Example 2-2

An organic electroluminescent device was manufactured through the same method as the manufacturing method of Example 2-1, except the hole transport layer was formed of Compound 3.

Example 2-3

An organic electroluminescent device was manufactured through the same method as the manufacturing method of Example 2-1, except the hole transport layer was formed of Compound 17.

Comparative Example 2-1

An organic electroluminescent device was manufactured through the same method as the manufacturing method of Example 2-1, except the hole transport layer was formed of the below Compound c1. The structure of Compound c1 differs from Compound 1 in that one of the covalent bonds forming the dibenzosilole ring is severed.

Comparative Example 2-2

An organic electroluminescent device was manufactured through the same method as the manufacturing method of Example 2-1, except the hole transport layer was formed of the below Compound c2. Compound c2 is a widely known arylamine compound which is generally used as a hole transport material.

Comparative Example 2-3

An organic electroluminescent device was manufactured through the same method as the manufacturing method of Example 2-1, except the hole transport layer was formed of the below Compound c3. Compound c3 is an arylamine compound which includes an arylsilyl group and a carbazolyl group:

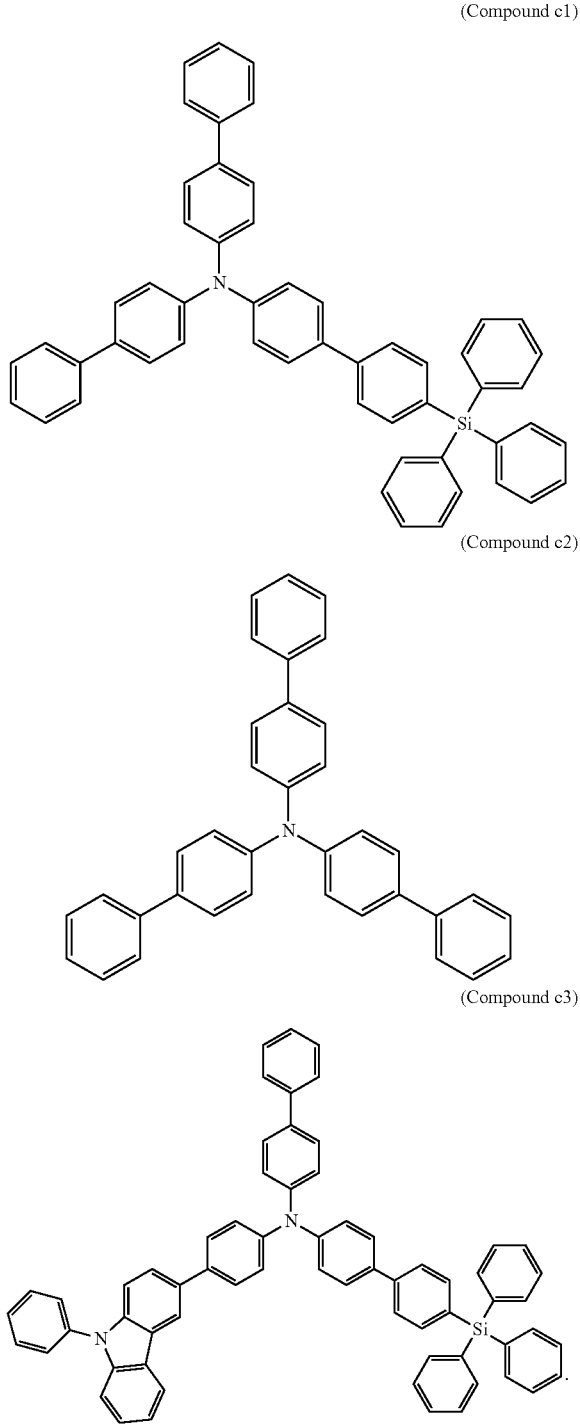

(Compound c1)

(Compound c2)

(Compound c3)

2-3-3. Evaluation Results

Evaluation results of the organic electroluminescent devices manufactured according to Examples 2-1 to 2-3 and Comparative Examples 2-1 to 2-3 are shown in the below Table 2. A luminance distribution measurement device (C9920-11) produced by HAMAMATSU Photonics was used to evaluate the field emitting properties of the manufactured organic electroluminescent device 100. The results shown in the below Table 2 were measured at a current density of about 10 mA/cm$^2$

TABLE 2

|  | HTL | Operating Voltage [V] | Emission Efficiency [cd/A] |
| --- | --- | --- | --- |
| Example 2-1 | Compound 1 | 6.1 | 7.8 |
| Example 2-2 | Compound 3 | 6.5 | 7.5 |
| Example 2-3 | Compound 17 | 6.3 | 7.6 |
| Comparative Example 2-1 | Compound c1 | 7.0 | 6.5 |
| Comparative Example 2-2 | Compound c2 | 7.5 | 5.2 |
| Comparative Example 2-3 | Compound c3 | 6.7 | 6.9 |

Referring to Table 2, it can be seen that the organic electroluminescent devices of Examples 2-1 to 2-3, in which the hole transport layer includes the second monoamine derivative, have lower operating voltages and improved emission efficiencies when compared to the organic electroluminescent devices of Comparative Examples 2-1 to 2-3.

In particular, it can be seen that the organic electroluminescent devices of Examples 2-1 to 2-3, in which embodiments of the second monoamine derivative form the hole transport layer, have lower operating voltages and improved emission efficiencies when compared to Comparative Example 2-1. The organic electroluminescent device of Comparative Example 2-1 uses Compound c1 in the hole transport layer, where one of the covalent bonds forming a dibenzosilole is severed.

In addition, it can be seen that the organic electroluminescent devices of Examples 2-1 to 2-3, in which embodiments of the second monoamine derivative form the hole transport layer, have lower operating voltages and improved emission efficiencies when compared to Comparative Example 2-2, in which Compound c2, a widely known arylamine derivative, forms the hole transport layer.

The organic electroluminescent devices of Examples 2-1 to 2-3 also have lower operating voltages and improved emission efficiencies compared to the organic electroluminescent devices of Comparative Example 2-3. The hole transport layer of Comparative Example 2-3 is formed of Compound c3 which includes an arylsilyl group and a carbazolyl group. Therefore, it can be understood that including a dibenzosilolyl group in the monoamine derivative according to the present embodiment lowers the operating voltage and improves the emission efficiency of the organic electroluminescent device.

For example, although arylamine compounds such as Compound c2 (used in Comparative Example 2-2) have high hole transporting abilities, such arylamine compounds have shallow HOMO levels, and large energy barriers against light-emitting materials of the emission layer. Moreover, although monoamine derivatives having a tetraphenylsilyl group, such as Compounds c1 and c3, have deep HOMO levels, the hole transporting abilities were low in Comparative Examples 2-1 and 2-3. The second monoamine derivative according to the present embodiment includes a dibenzosilolyl group, and may thus have both a high hole transporting ability and a deep HOMO level. Consequently, the efficiency is good, and holes and electrons may be recombined in the emission layer.

Therefore, the monoamine derivative according to the present embodiment may be useful in practical applications of organic electroluminescent devices in various areas of use.

As described above, according to one or more embodiments of the present disclosure, an organic electroluminescent device having a lower operating voltage and an improved emission efficiency may be provided.

As used herein, expressions such as "at least one of," "one of," "at least one selected from," and "one selected from," when preceding a list of elements, modify the entire list of elements and do not modify the individual elements of the list. Further, the use of "may" when describing embodiments of the present invention refers to "one or more embodiments of the present invention".

In addition, as used herein, the terms "use," "using," and "used" may be considered synonymous with the terms "utilize," "utilizing," and "utilized," respectively.

As used herein, the terms "substantially," "about," and similar terms are used as terms of approximation and not as terms of degree, and are intended to account for the inherent deviations in measured or calculated values that would be recognized by those of ordinary skill in the art.

Also, any numerical range recited herein is intended to include all subranges of the same numerical precision subsumed within the recited range. For example, a range of "1.0 to 10.0" is intended to include all subranges between (and including) the recited minimum value of 1.0 and the recited maximum value of 10.0, that is, having a minimum value equal to or greater than 1.0 and a maximum value equal to or less than 10.0, such as, for example, 2.4 to 7.6. Any maximum numerical limitation recited herein is intended to include all lower numerical limitations subsumed therein and any minimum numerical limitation recited in this specification is intended to include all higher numerical limitations subsumed therein. Accordingly, Applicant reserves the right to amend this specification, including the claims, to expressly recite any sub-range subsumed within the ranges expressly recited herein.

The above-disclosed subject matter is to be considered illustrative and not restrictive, and the appended claims are intended to cover all such modifications, enhancements, and other embodiments, which fall within the true spirit and scope of the present disclosure. Thus, to the maximum extent allowed by law, the scope of the present disclosure is to be determined by the broadest permissible interpretation of the following claims and their equivalents, and shall not be restricted or limited by the foregoing detailed description.

What is claimed is:

1. A monoamine derivative selected from the group of compounds represented by Formula 2 and Formula 4;

Formula 2

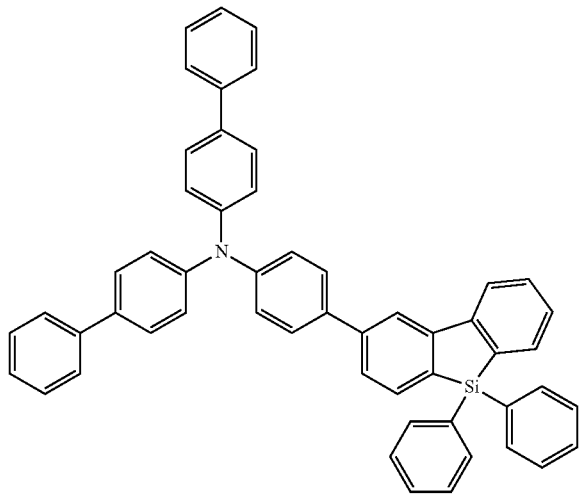

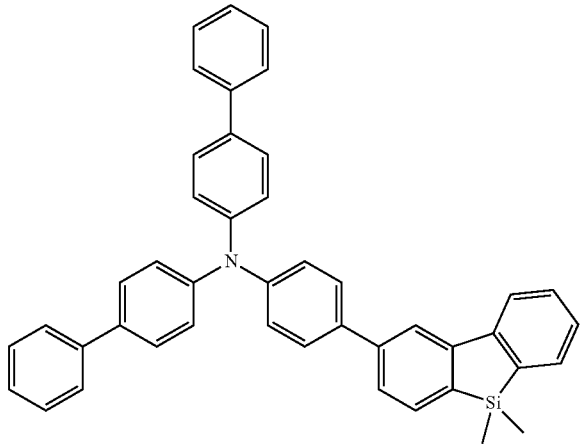

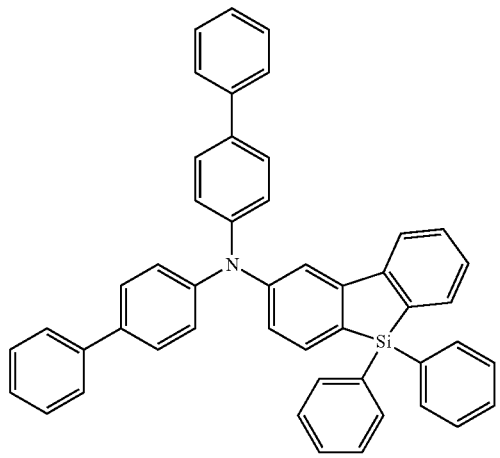

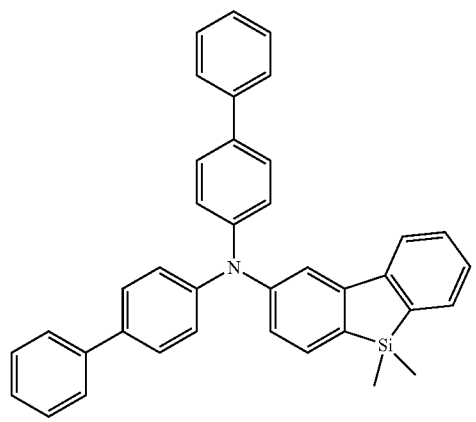
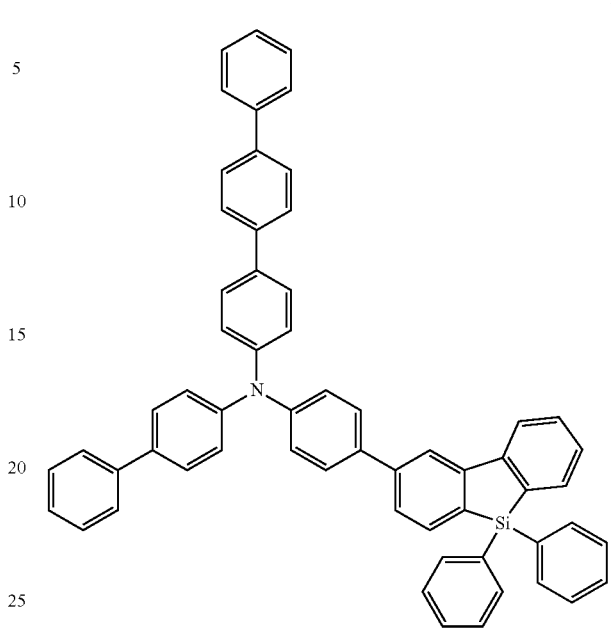
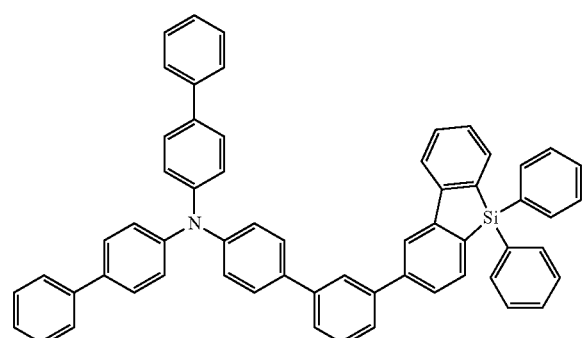
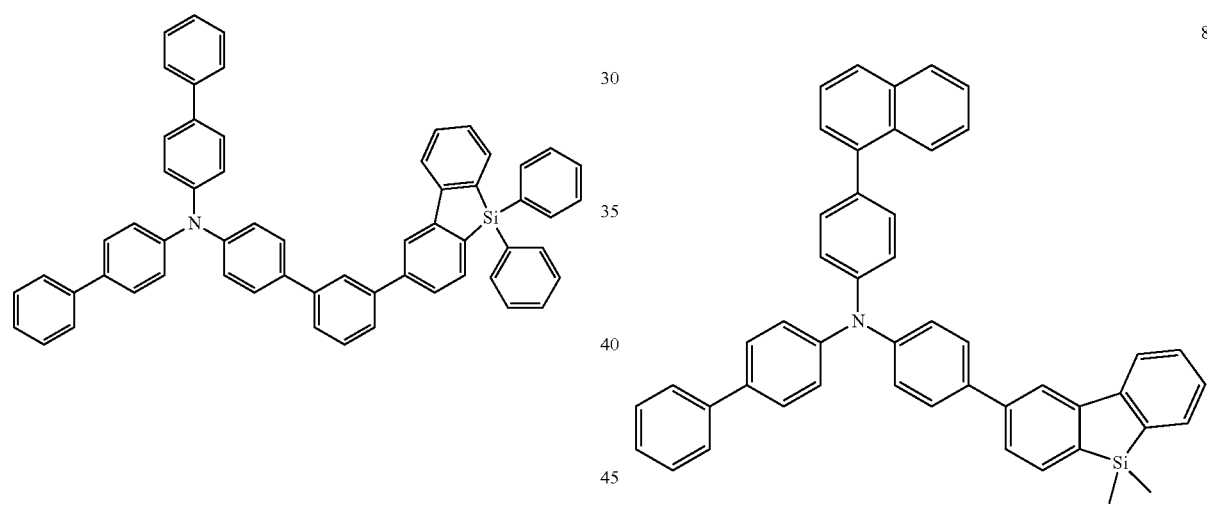
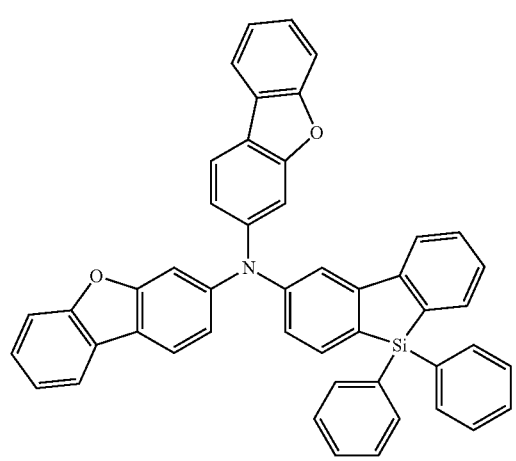
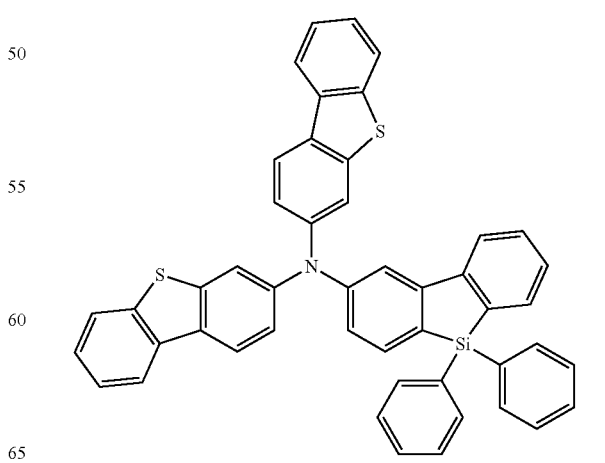

10
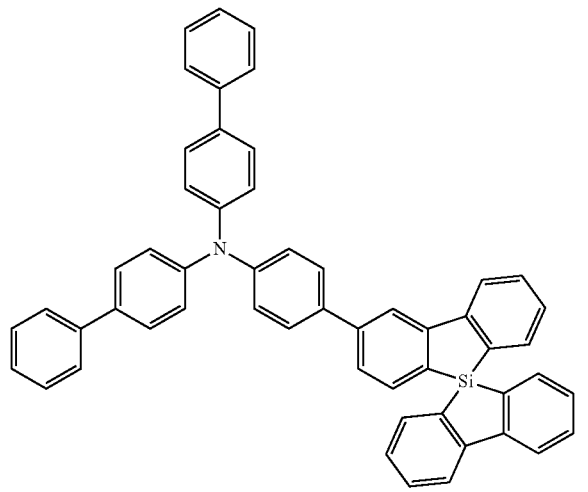
11
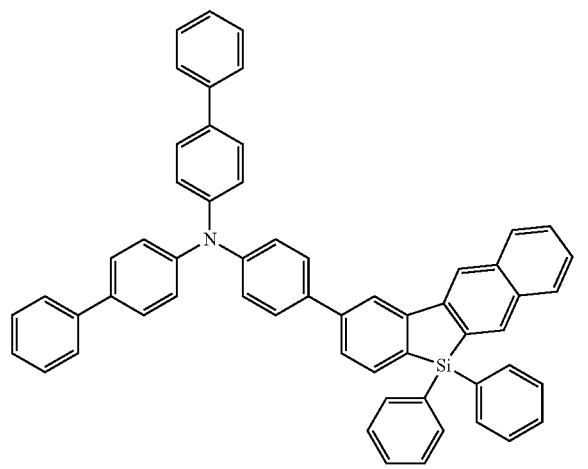
12
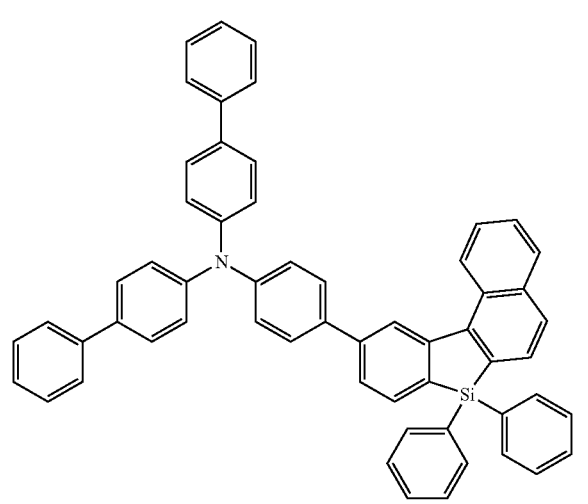
13
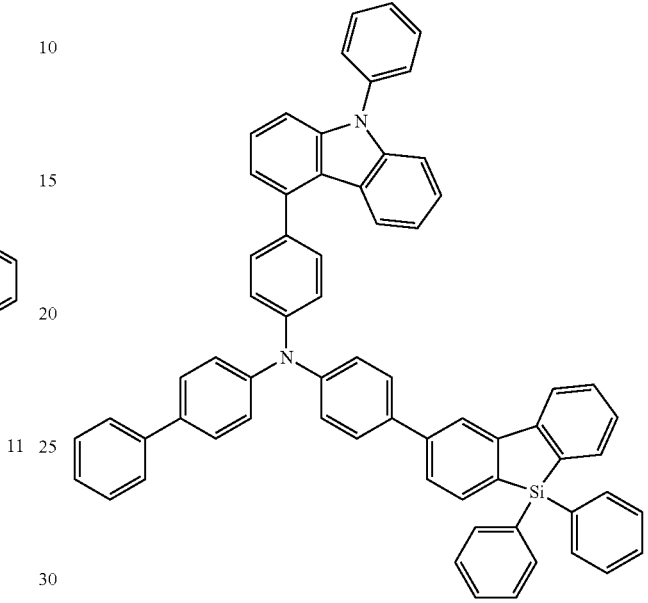
14
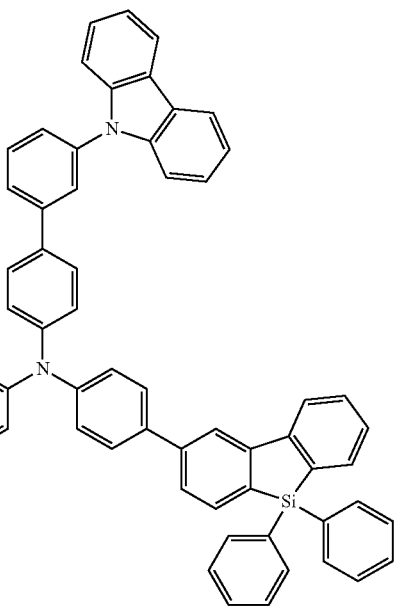

15
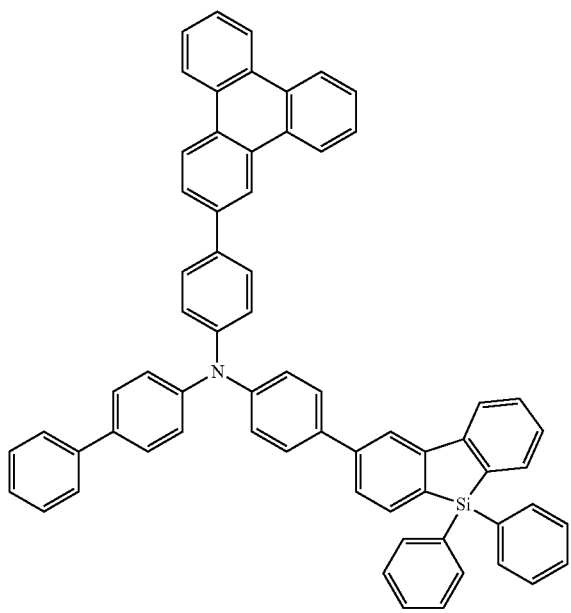
16
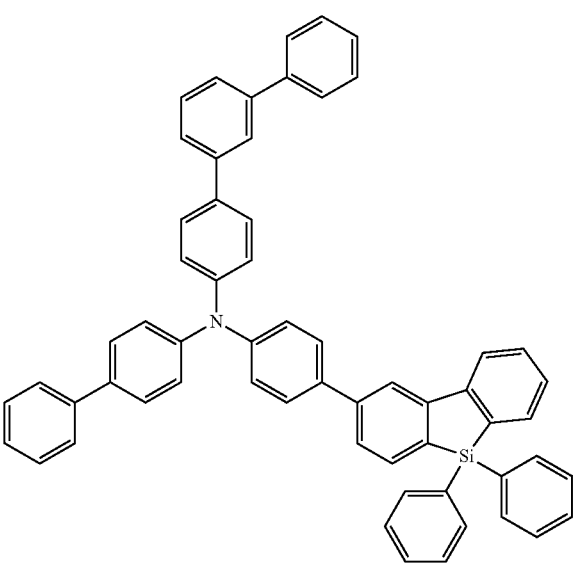
17
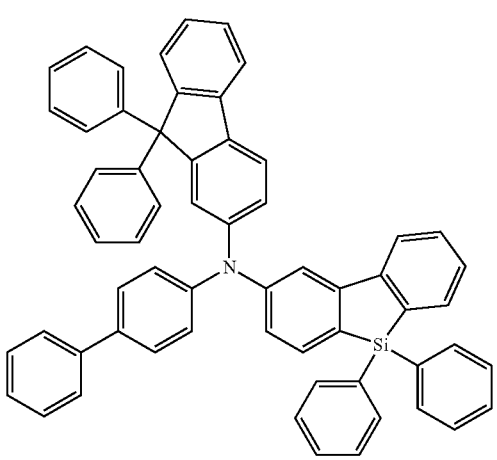
18
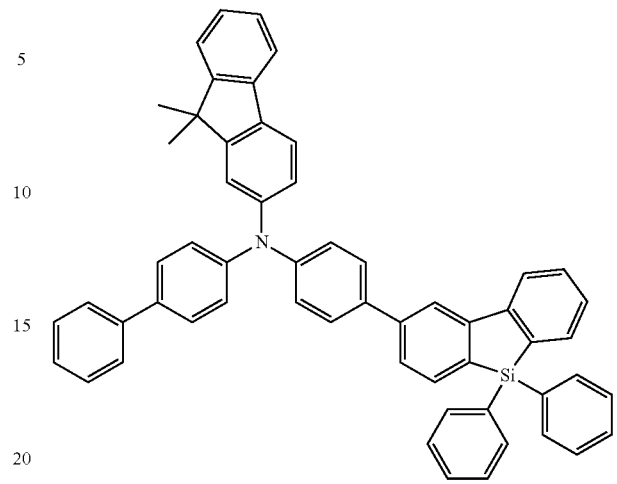
19
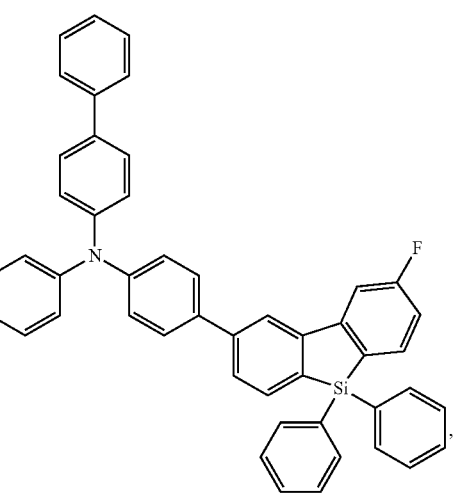
20

Formula 4
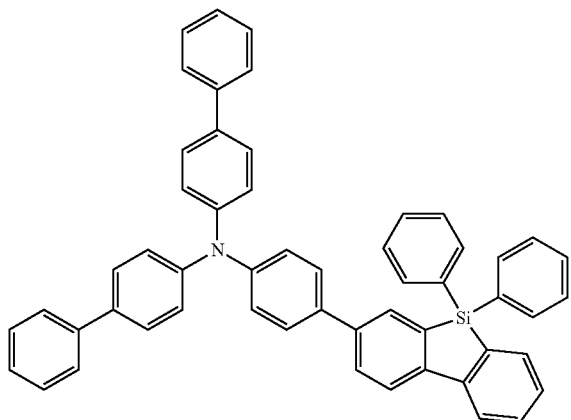
1
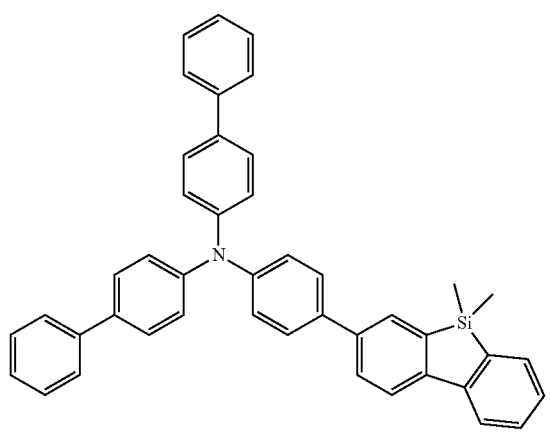
2
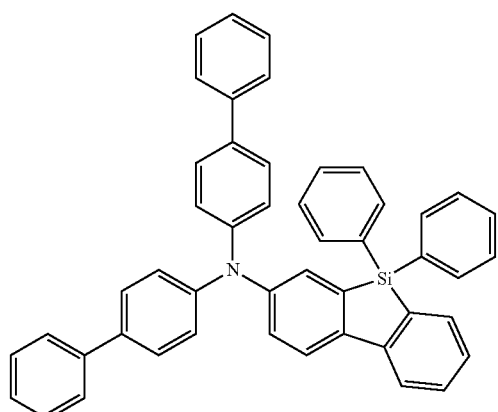
3
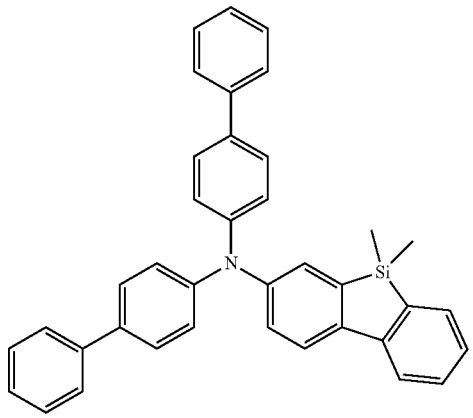
4
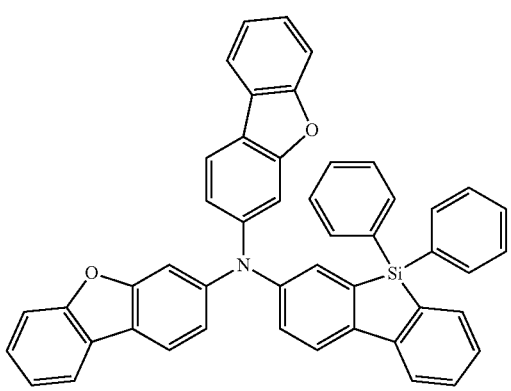
5
6

7
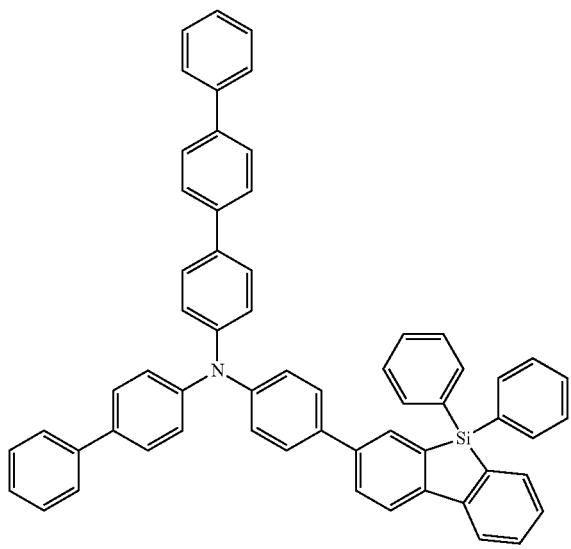
8
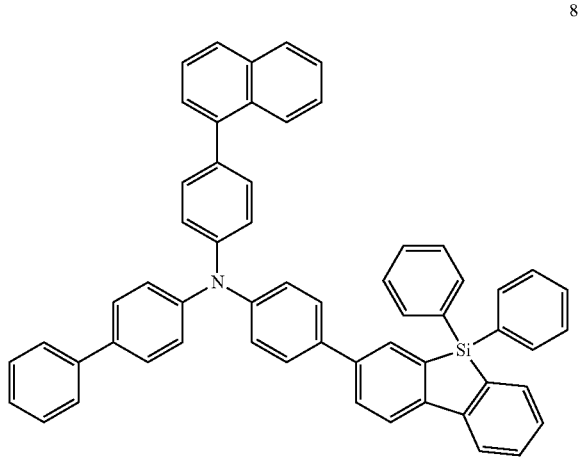
9
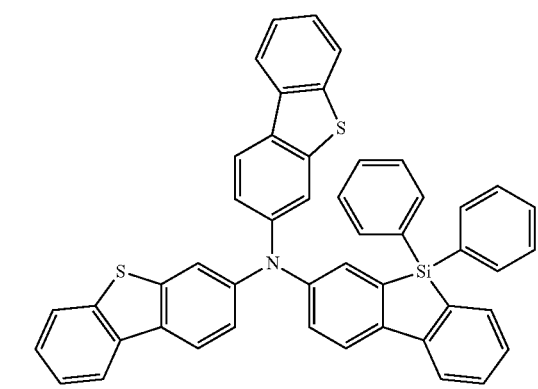
10
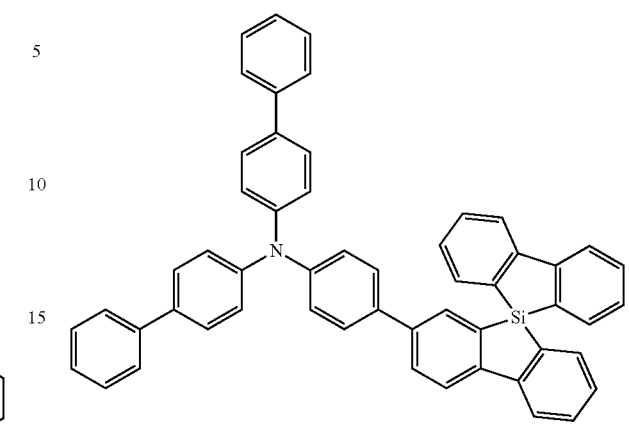
11
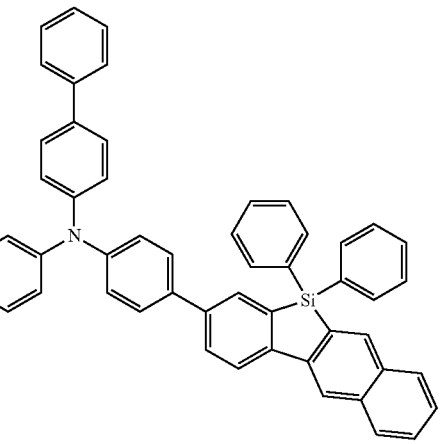
12
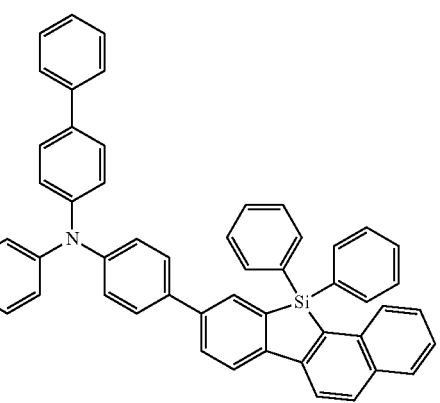

75
-continued
13
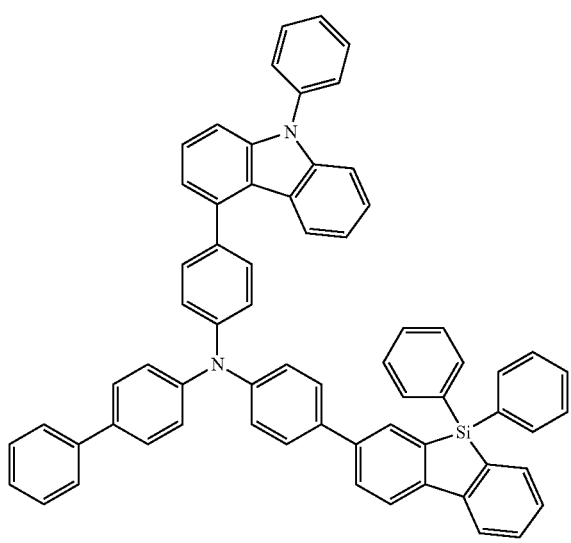
14
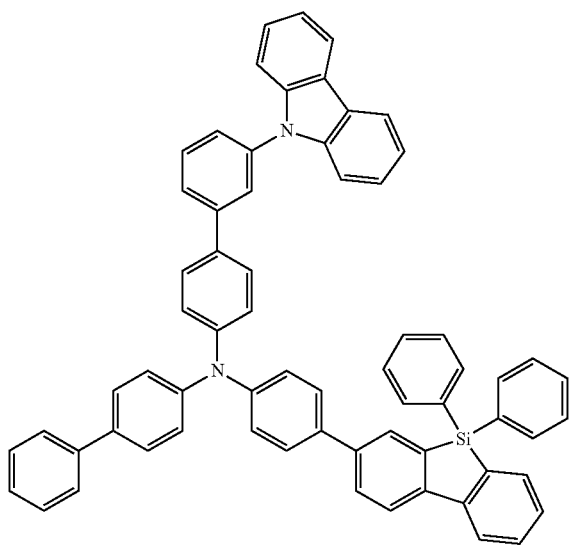
76
-continued
15
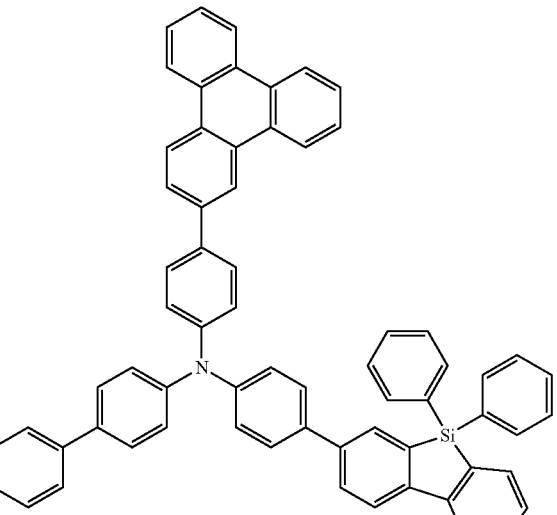
16
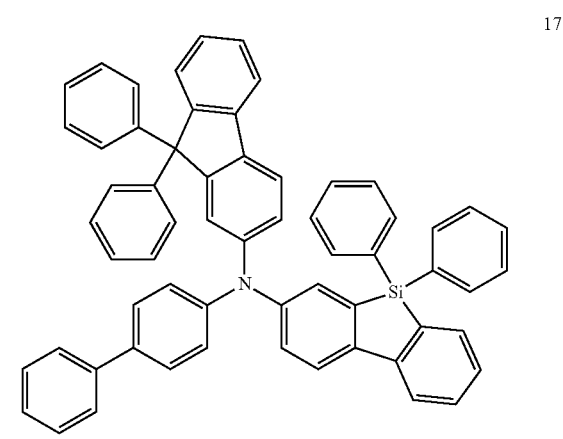
17

-continued

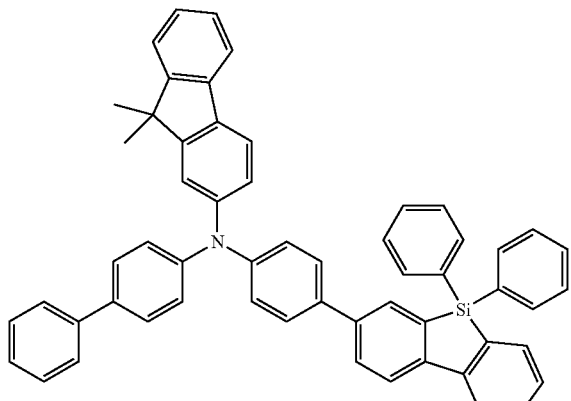

18

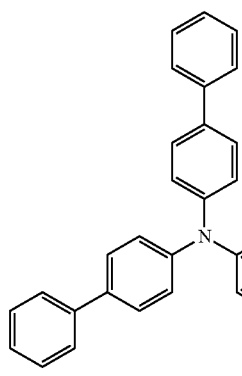

19

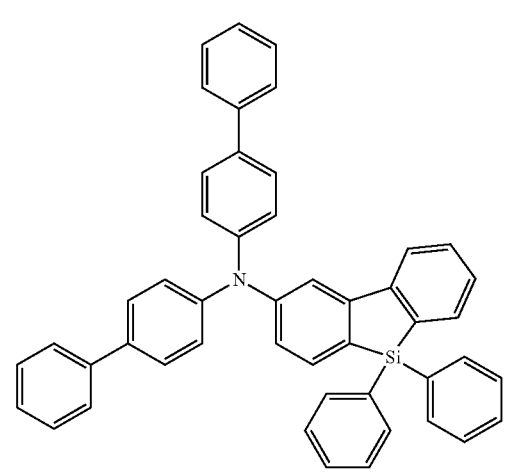

20

Formula 2

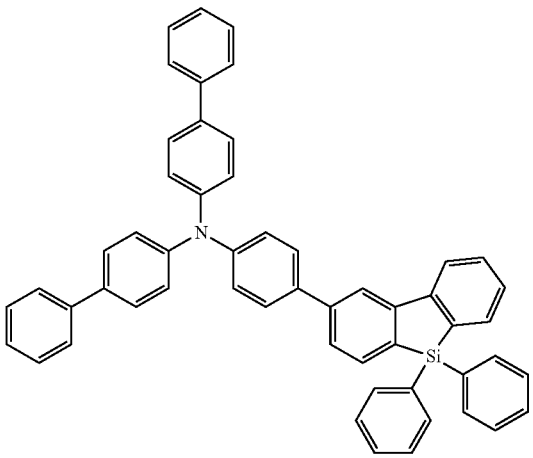

1

2

3

2. An organic electroluminescent device, comprising:
an anode;
a hole injection layer on the anode;
a hole transport layer on the hole injection layer; and
an emission layer on the hole transport layer;
wherein at least one layer selected from the hole injection layer, the hole transport layer, and the emission layer includes a monoamine derivative selected from the group of compounds represented by Formula 2 and Formula 4;

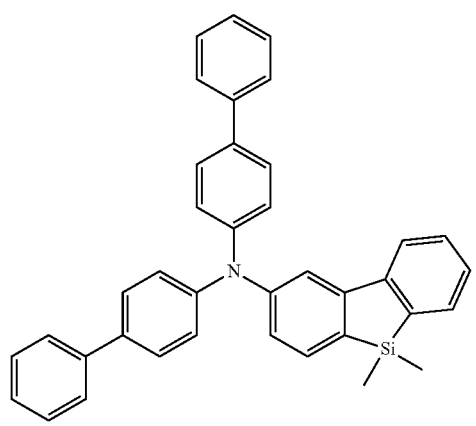
4
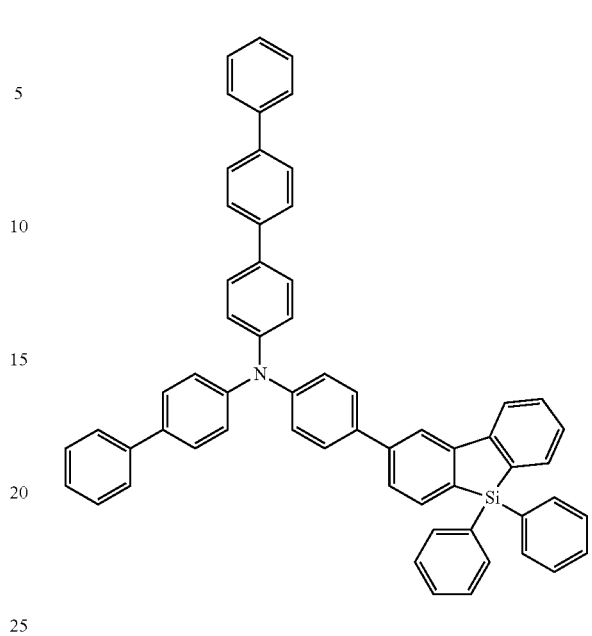
7
5
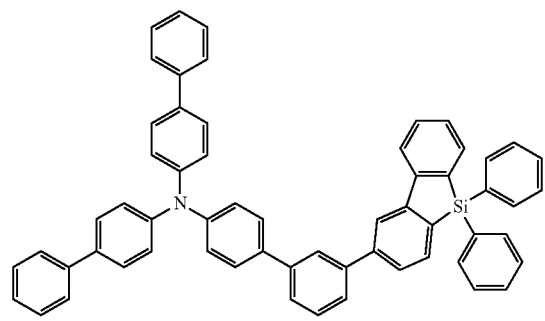
5
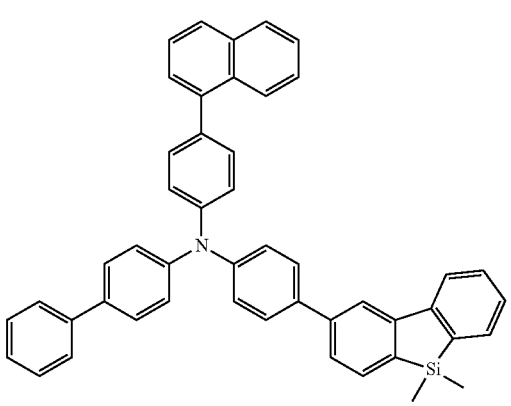
8
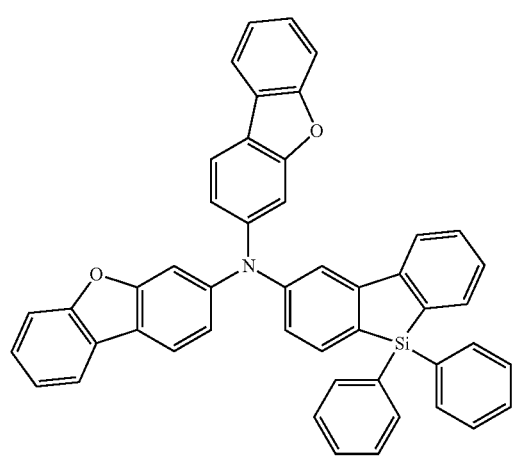
6
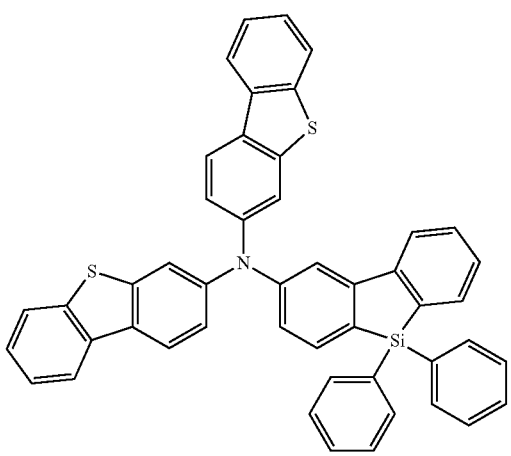
9

10
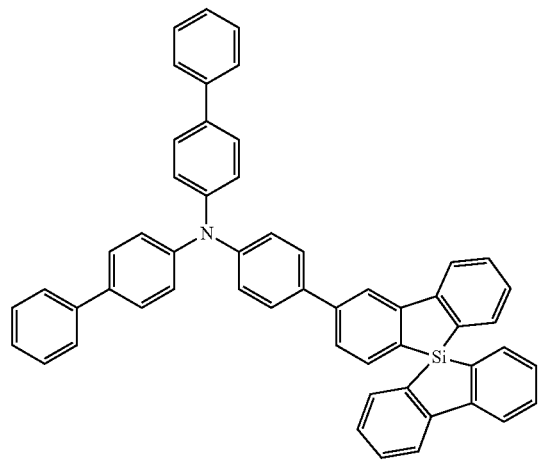
11
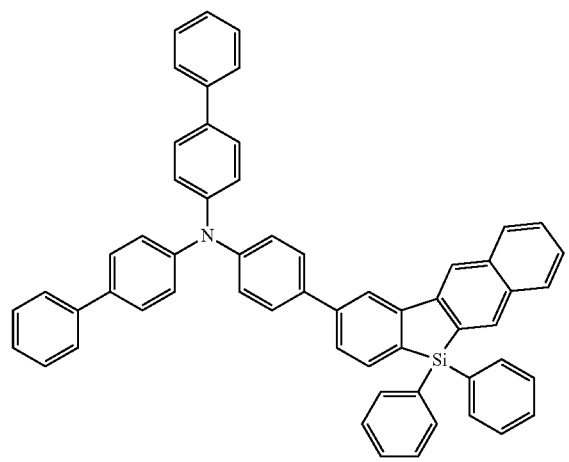
12
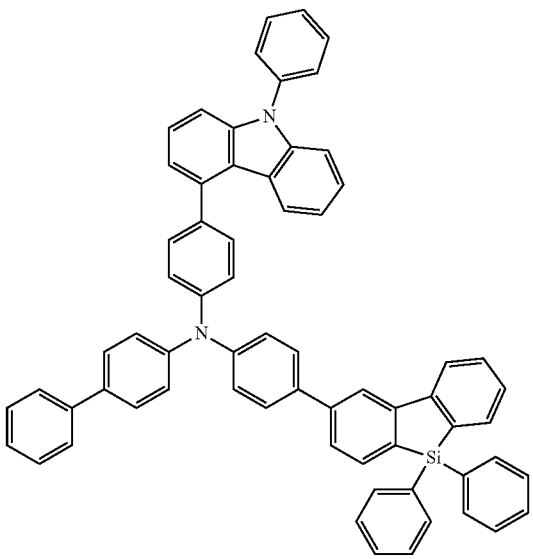
13
14
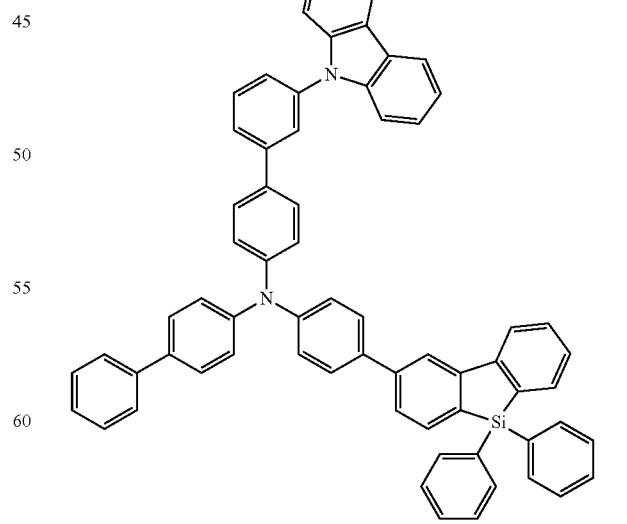

15
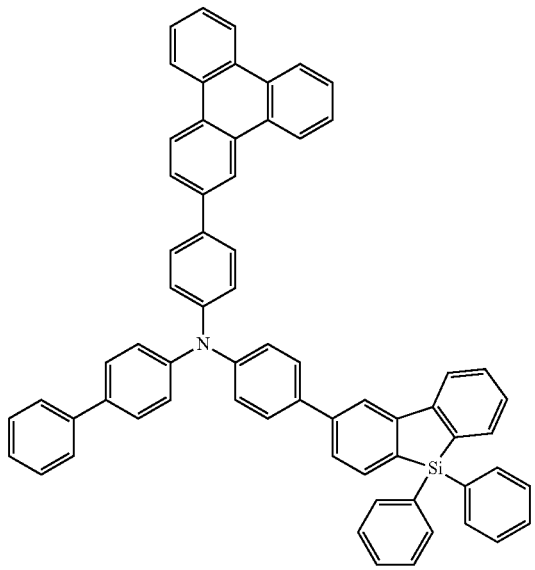
16
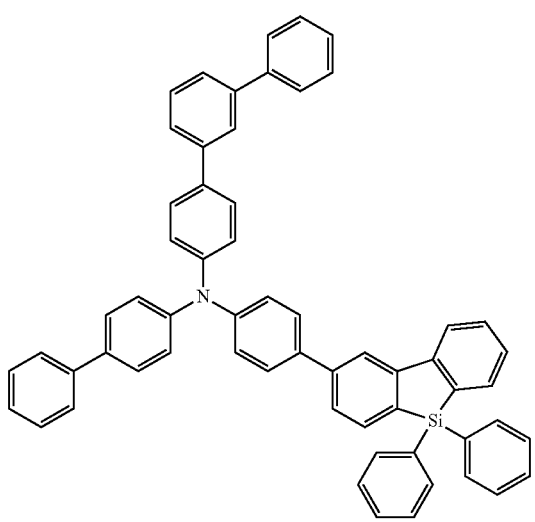
17
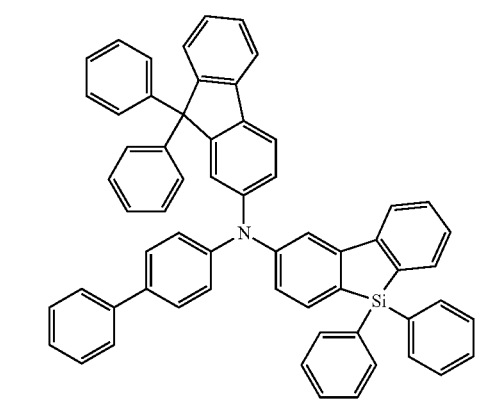
18
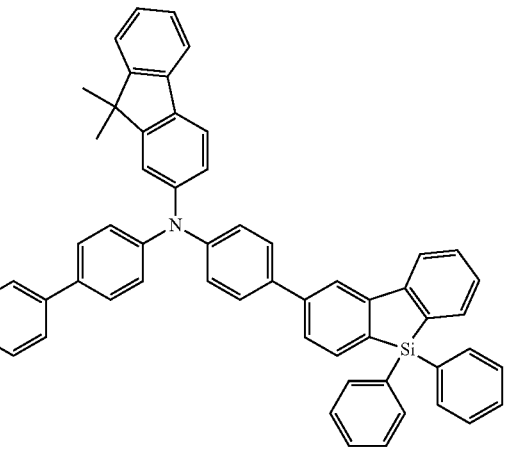
19
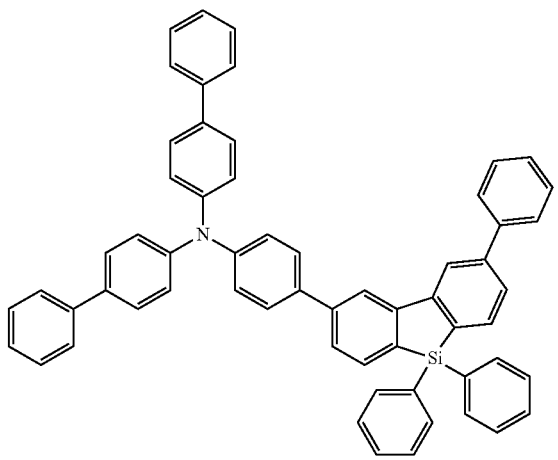
20
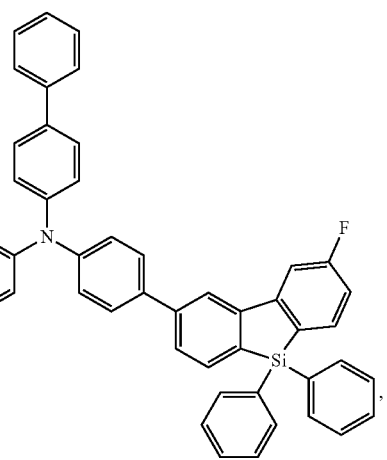

Formula 4
1
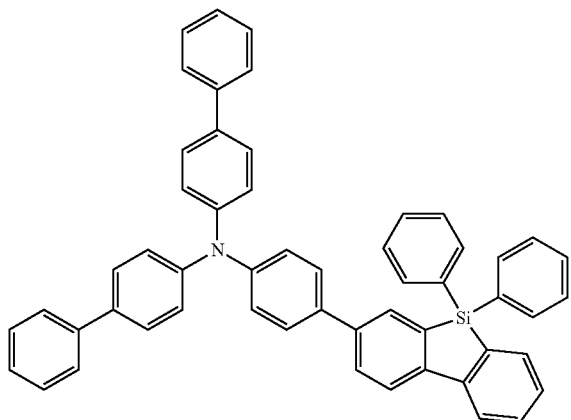
2
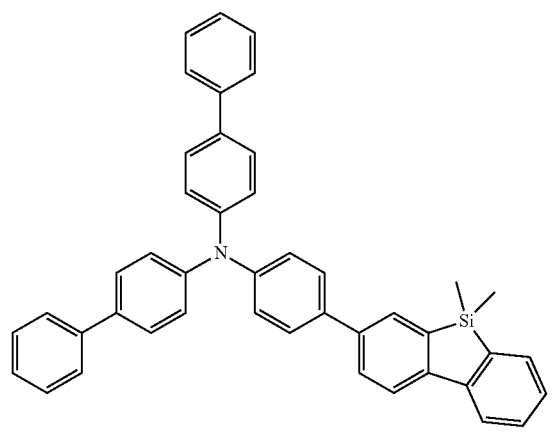
3
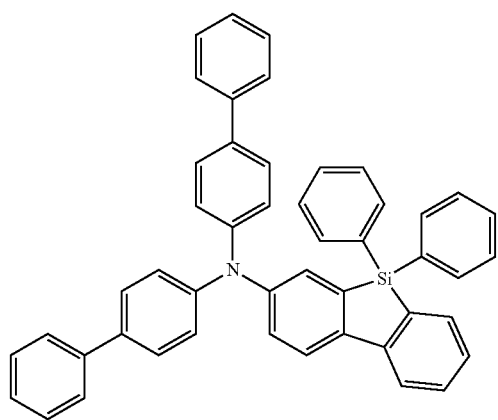
4
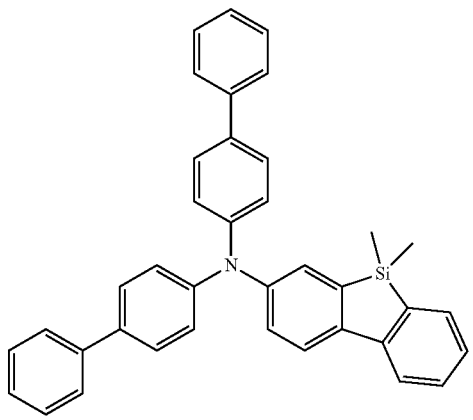
5
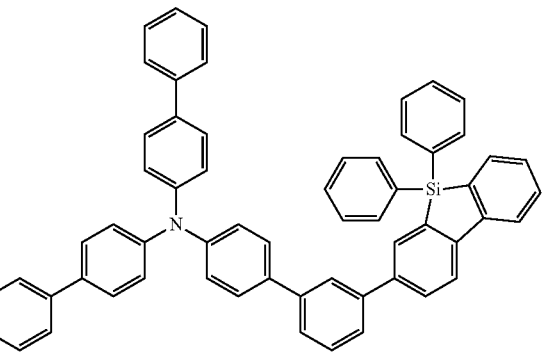
6
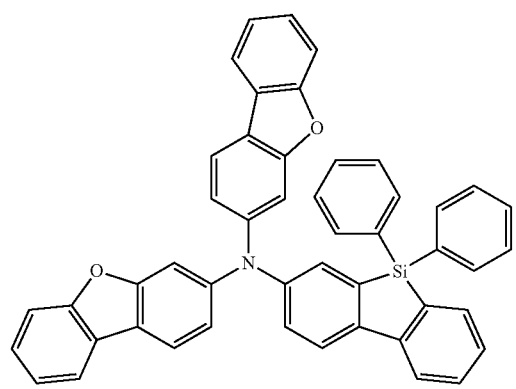

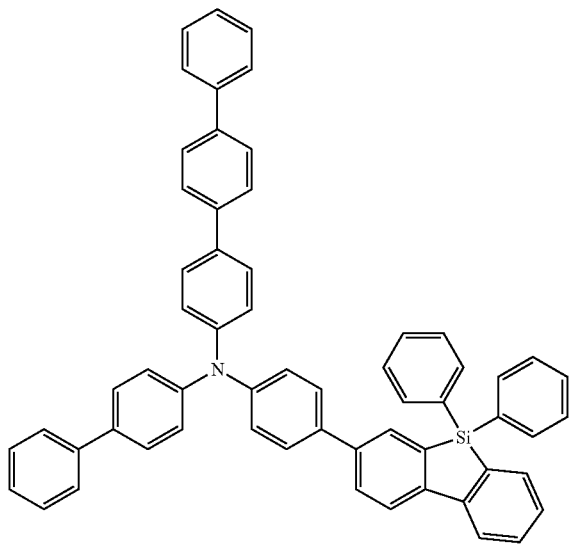
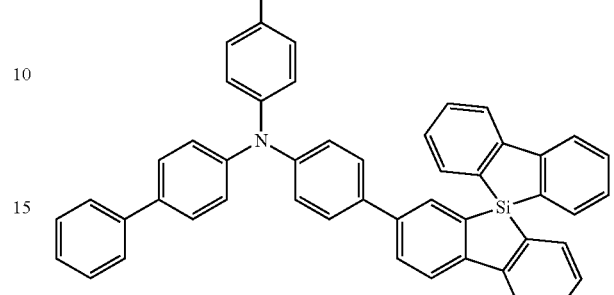
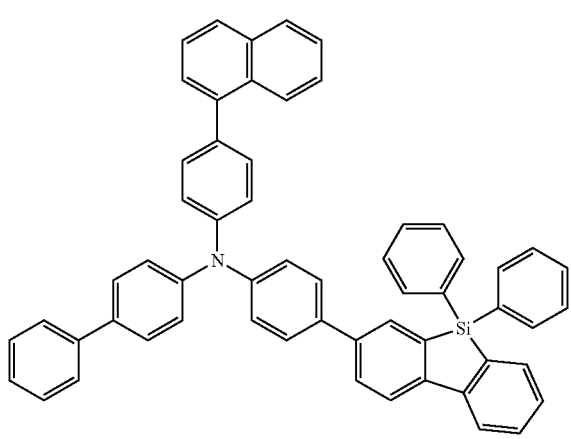
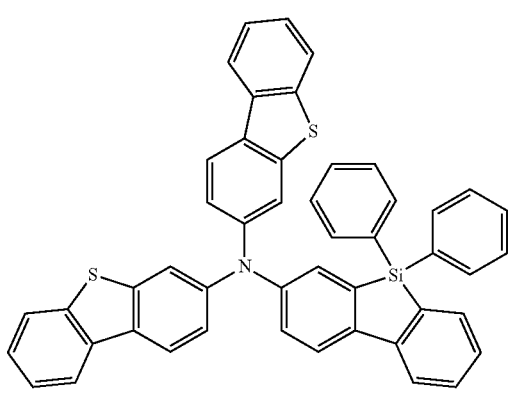
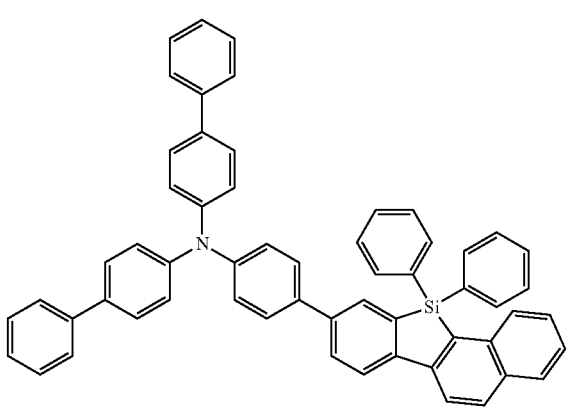

-continued
13
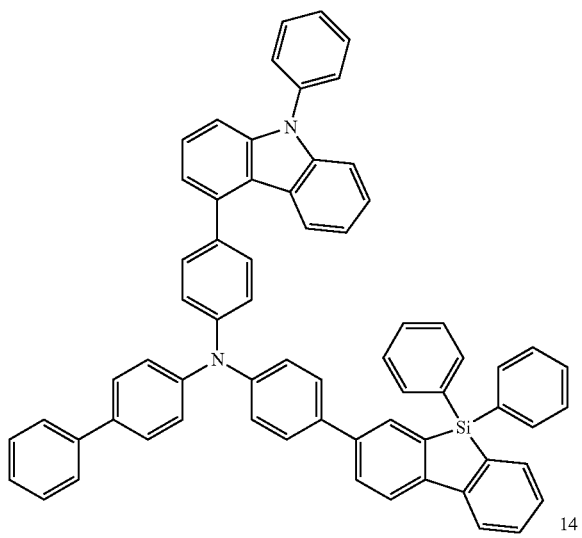
14
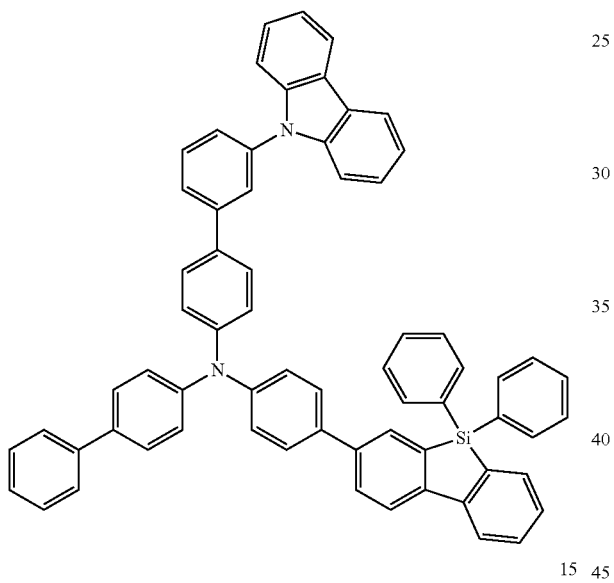
15
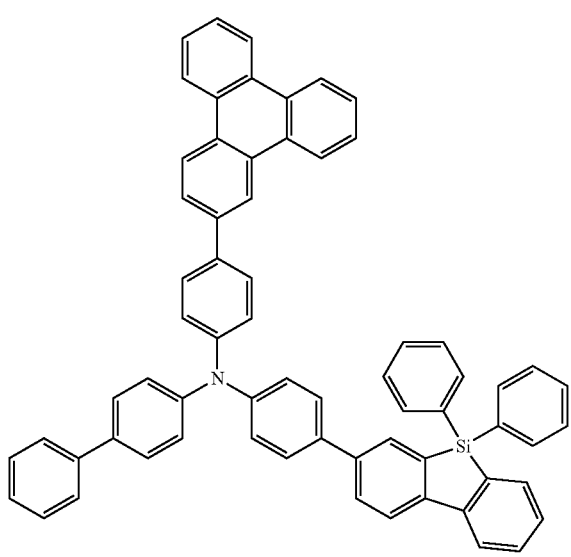
-continued
16
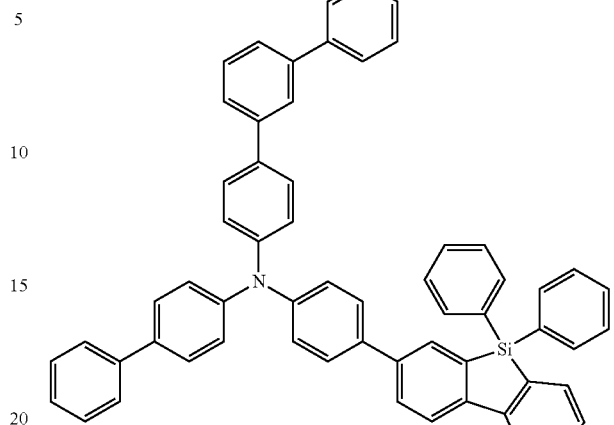
17
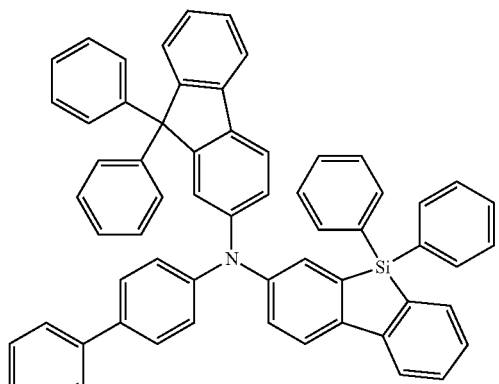
18
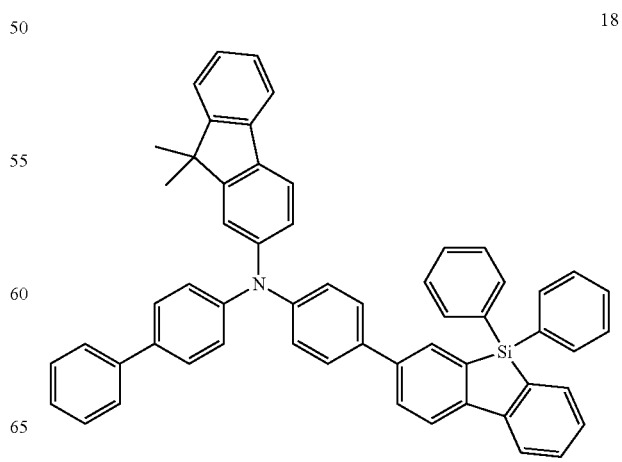

-continued
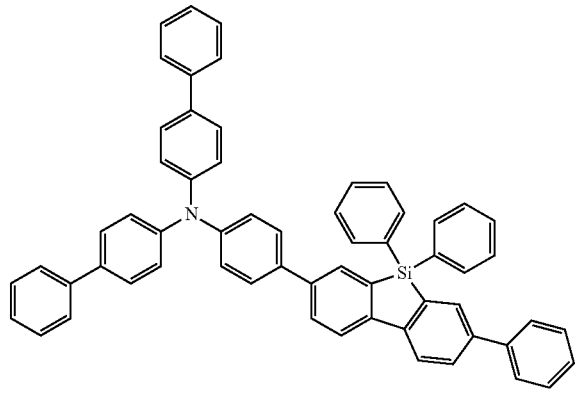
-continued
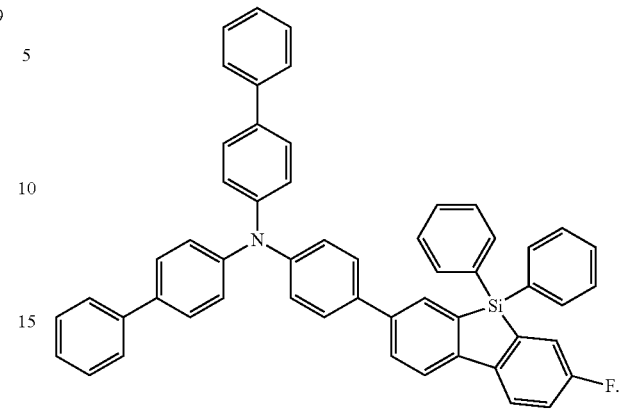
* * * * *